United States Patent
Forsell

(10) Patent No.: US 10,226,372 B2
(45) Date of Patent: Mar. 12, 2019

(54) OBESITY TREATMENT

(76) Inventor: Peter Forsell, Bouveret (CH)

( * ) Notice: Subject to any disclaimer, the term of this patent is extended or adjusted under 35 U.S.C. 154(b) by 657 days.

(21) Appl. No.: 13/146,387

(22) PCT Filed: Jan. 29, 2010

(86) PCT No.: PCT/SE2010/050101
§ 371 (c)(1),
(2), (4) Date: Oct. 11, 2011

(87) PCT Pub. No.: WO2010/087774
PCT Pub. Date: Aug. 5, 2010

(65) Prior Publication Data
US 2012/0029550 A1    Feb. 2, 2012

Related U.S. Application Data

(60) Provisional application No. 61/213,813, filed on Jul. 17, 2009.

(30) Foreign Application Priority Data

Jan. 29, 2009   (WO) ................. PCT/SE2009/000047
Jul. 17, 2009   (SE) ...................................... 0901007
Oct. 12, 2009   (WO) ................. PCT/SE2009/000452
Oct. 12, 2009   (WO) ................. PCT/SE2009/051156

(51) Int. Cl.
*A61F 2/04*    (2013.01)
*A61F 5/00*    (2006.01)
(Continued)

(52) U.S. Cl.
CPC ................ *A61F 5/003* (2013.01); *A61B 1/04* (2013.01); *A61B 1/2736* (2013.01);
(Continued)

(58) Field of Classification Search
CPC ........ A61F 2/04; A61F 5/0033; A61F 5/0036; A61F 5/004; A61F 5/0046; A61F 5/0069; A61F 5/0073; A61F 5/0083; A61F 5/0086; A61F 5/0089; A61F 5/0009; A61F 5/0013; A61F 5/0026; A61F 5/003; A61F 5/005;
(Continued)

(56) References Cited

U.S. PATENT DOCUMENTS 2,574,158 A * 11/1951 Sullivan .................... A63F 9/12
                                                                273/160
6,579,301 B1 * 6/2003 Bales et al. .................... 606/191
(Continued)

FOREIGN PATENT DOCUMENTS

WO    WO 0158391        8/2001
WO    2007136735 A2    11/2007
(Continued)

OTHER PUBLICATIONS

International Search Report for PCT/SE2010/050101, dated May 5, 2010.

*Primary Examiner* — Diane Yabut

(57) ABSTRACT

An apparatus for treating obesity comprises a volume filling device formed by at least two segments and is provided and following implantation, the device is placed resting against the stomach wall of the patient to reduce the inner volume of the stomach, thereby affecting the patients appetite.

24 Claims, 51 Drawing Sheets

(51) Int. Cl.

| | | |
|---|---|---|
| *A61B 17/04* | (2006.01) | |
| *A61B 17/068* | (2006.01) | |
| *A61B 17/08* | (2006.01) | |
| *A61B 1/273* | (2006.01) | |
| *A61B 1/04* | (2006.01) | |
| *A61B 1/313* | (2006.01) | |
| *A61B 17/064* | (2006.01) | |
| *A61B 17/32* | (2006.01) | |
| *A61B 17/34* | (2006.01) | |
| *A61N 1/36* | (2006.01) | |
| *A61B 17/00* | (2006.01) | |
| *A61B 17/30* | (2006.01) | |

(52) U.S. Cl.
CPC ...... *A61B 1/3132* (2013.01); *A61B 17/00234* (2013.01); *A61B 17/0469* (2013.01); *A61B 17/064* (2013.01); *A61B 17/068* (2013.01); *A61B 17/08* (2013.01); *A61B 17/30* (2013.01); *A61B 17/320016* (2013.01); *A61B 17/3423* (2013.01); *A61B 17/3474* (2013.01); *A61F 2/04* (2013.01); *A61F 5/004* (2013.01); *A61F 5/005* (2013.01); *A61F 5/0013* (2013.01); *A61F 5/0026* (2013.01); *A61F 5/0033* (2013.01); *A61F 5/0036* (2013.01); *A61F 5/0043* (2013.01); *A61F 5/0046* (2013.01); *A61F 5/0069* (2013.01); *A61F 5/0073* (2013.01); *A61F 5/0079* (2013.01); *A61F 5/0086* (2013.01); *A61F 5/0089* (2013.01); *A61N 1/36007* (2013.01); *A61B 17/0682* (2013.01); *A61B 2017/00278* (2013.01); *A61B 2017/00561* (2013.01); *A61B 2017/00818* (2013.01); *A61B 2017/00827* (2013.01); *A61B 2017/081* (2013.01); *A61B 2017/306* (2013.01); *A61B 2017/308* (2013.01); *A61F 5/0076* (2013.01); *A61F 2002/044* (2013.01); *A61F 2002/045* (2013.01); *A61F 2005/002* (2013.01); *A61F 2005/0016* (2013.01); *A61F 2005/0023* (2013.01); *A61F 2250/0001* (2013.01); *A61F 2250/0004* (2013.01)

(58) Field of Classification Search
CPC .... A61F 5/0053; A61F 5/0056; A61F 5/0059; A61F 5/0063; A61F 5/0066; A61F 5/0076; A61F 5/0079; A61B 17/00; A61B 17/12136; A61B 17/12145; A61B 17/12159; A61B 17/12163; A61B 17/12172; A61B 17/12186; A61B 17/1219; A61B 17/3415
USPC ............................... 606/153, 191, 192, 195; 623/23.64–23.68; 128/898
See application file for complete search history.

(56) References Cited

U.S. PATENT DOCUMENTS

| | | | |
|---|---|---|---|
| 7,502,649 B2* | 3/2009 | Ben-Haim et al. | 607/40 |
| 8,100,931 B2* | 1/2012 | Baker et al. | 606/191 |
| 2003/0021822 A1 | 1/2003 | Lloyd | |
| 2005/0245957 A1 | 11/2005 | Starkebaum et al. | |
| 2005/0261712 A1* | 11/2005 | Balbierz et al. | 606/153 |
| 2005/0267596 A1 | 12/2005 | Chen et al. | |
| 2005/0283235 A1* | 12/2005 | Kugler | A61B 17/12009 623/14.13 |
| 2007/0104755 A1 | 5/2007 | Sterling et al. | |
| 2007/0250090 A1* | 10/2007 | Makower et al. | 606/157 |
| 2008/0051823 A1* | 2/2008 | Makower et al. | 606/192 |
| 2010/0249825 A1* | 9/2010 | Nihalani | A61B 17/12099 606/198 |

FOREIGN PATENT DOCUMENTS

| | | |
|---|---|---|
| WO | WO 2008/016776 | 2/2008 |
| WO | WO 2009/096865 | 8/2009 |

* cited by examiner

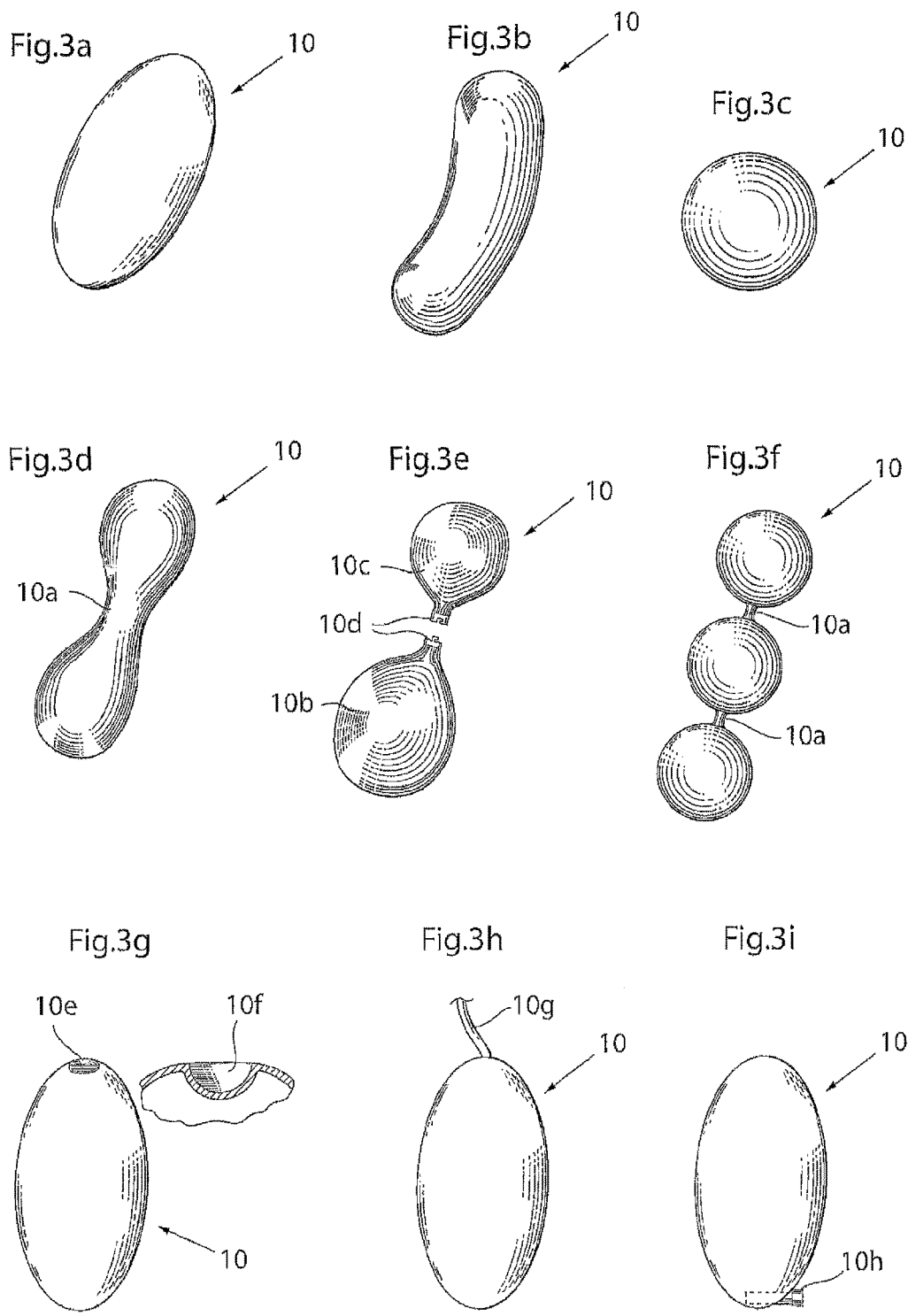

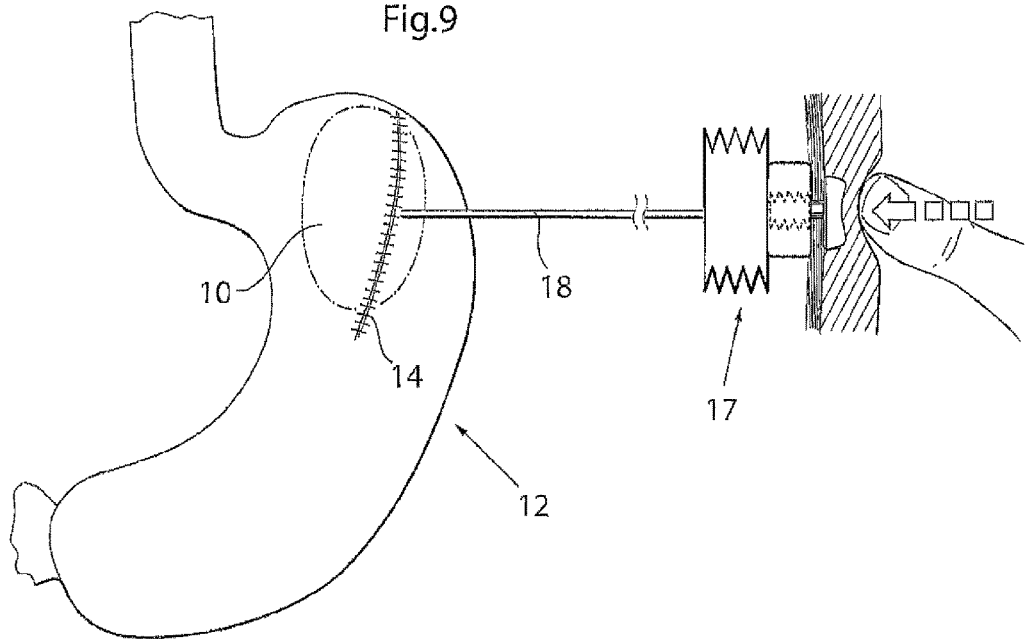
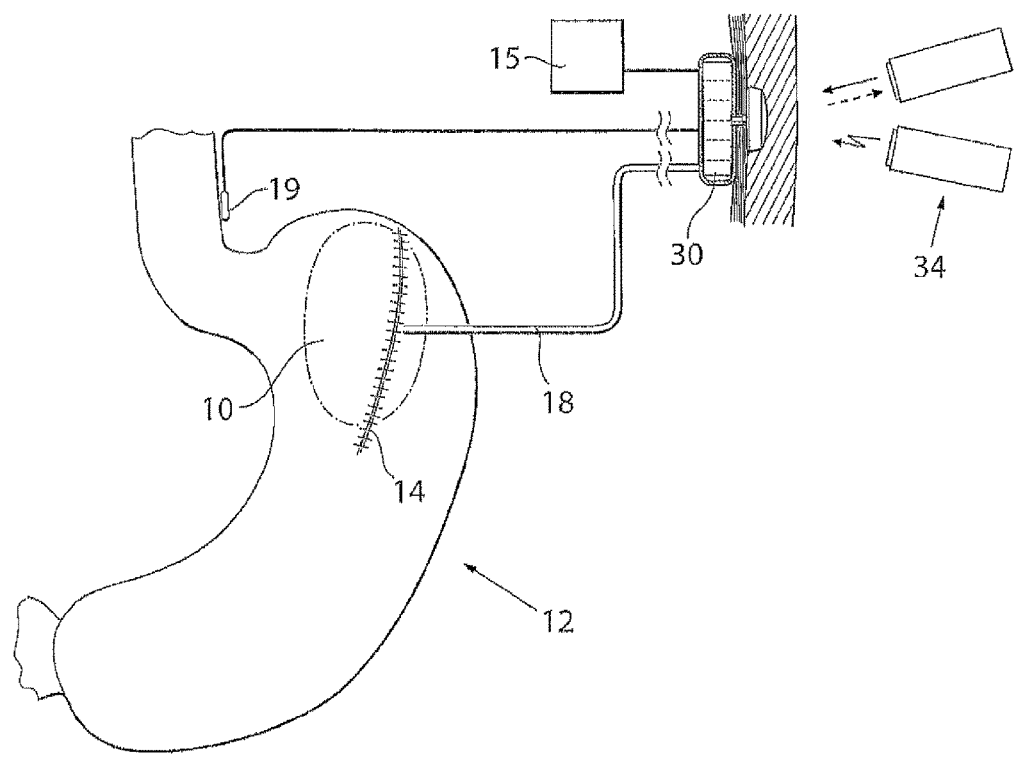

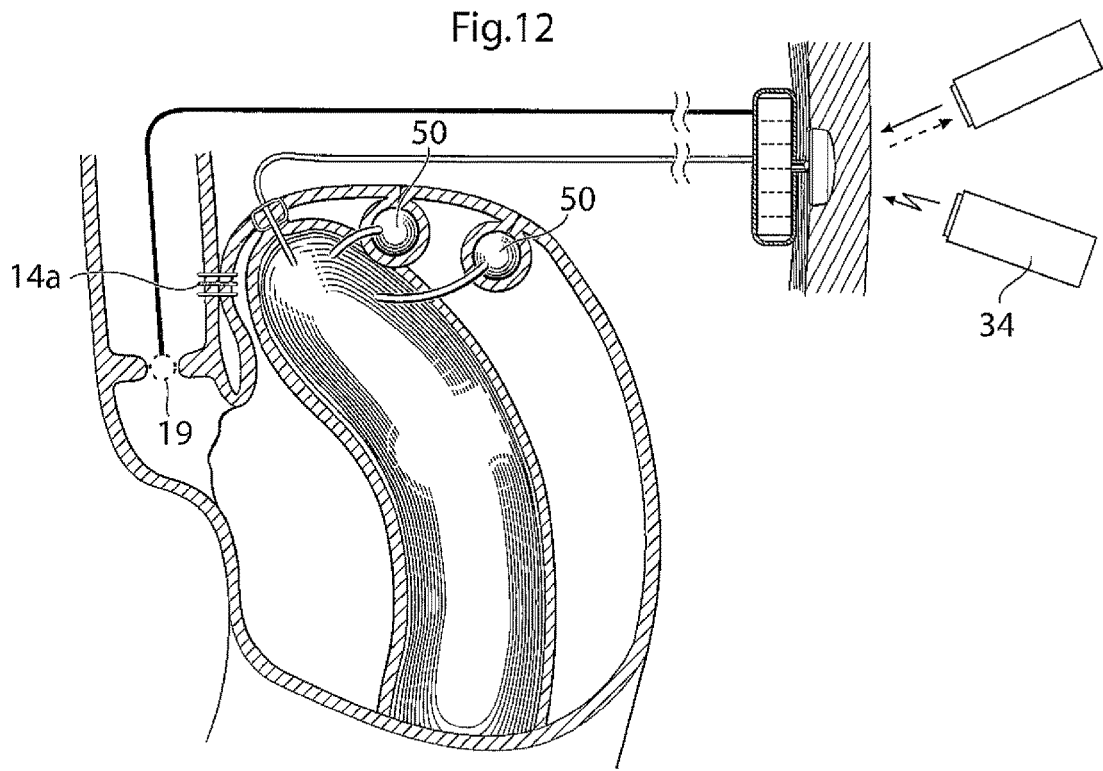

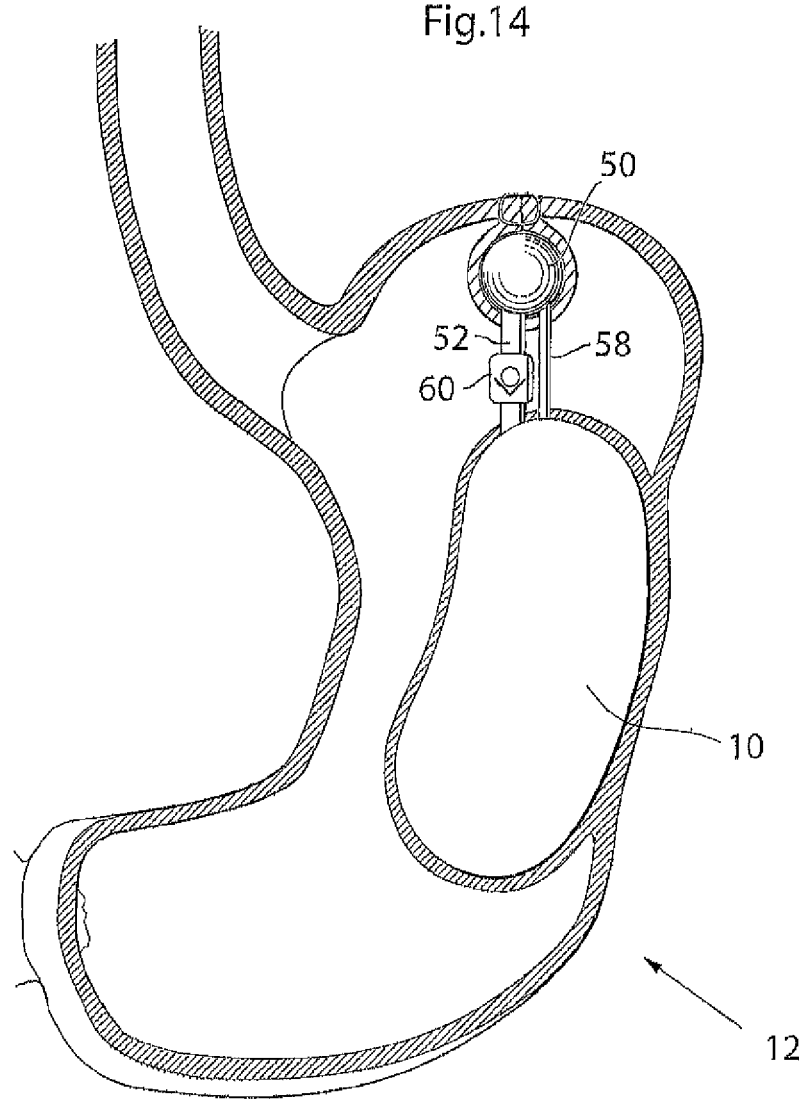

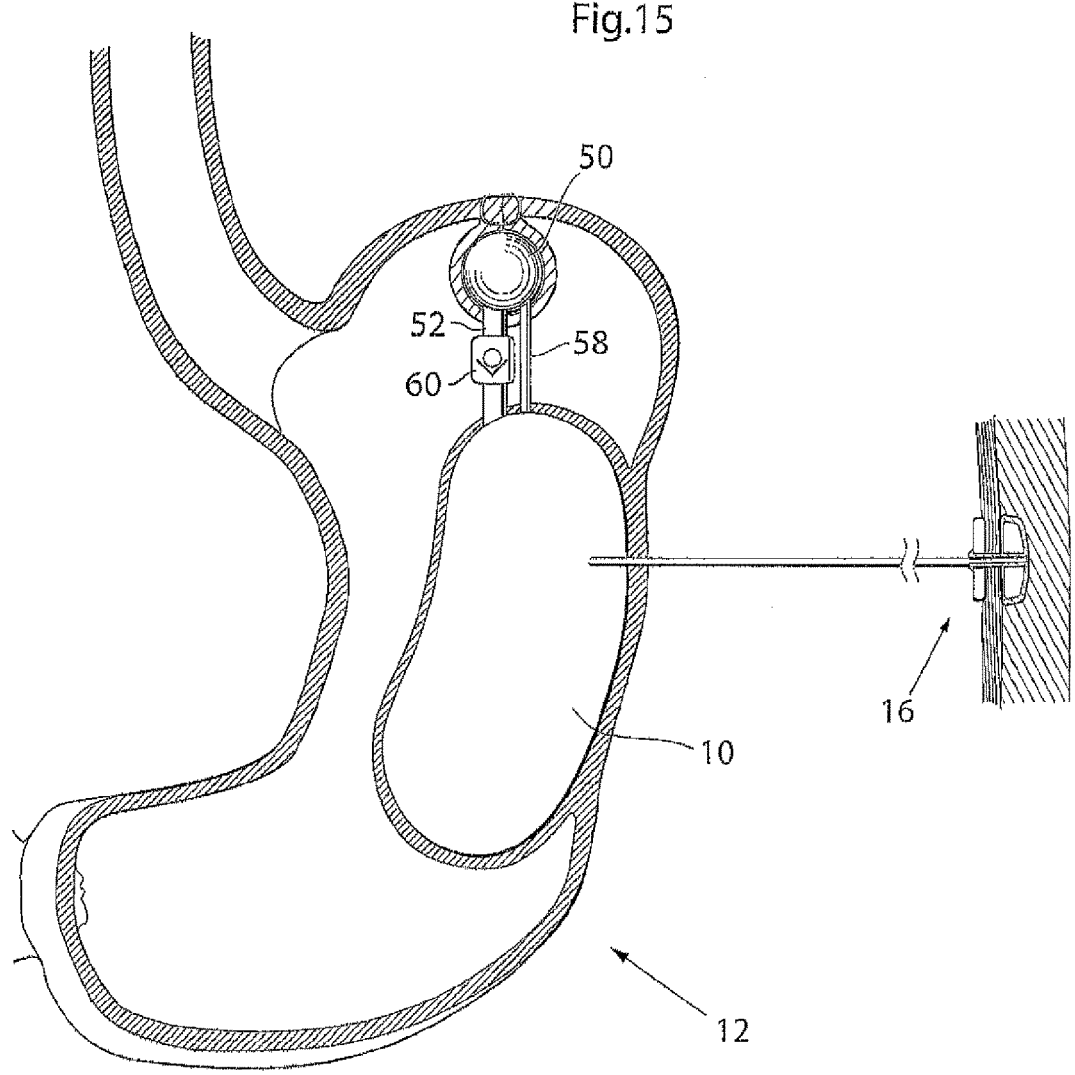

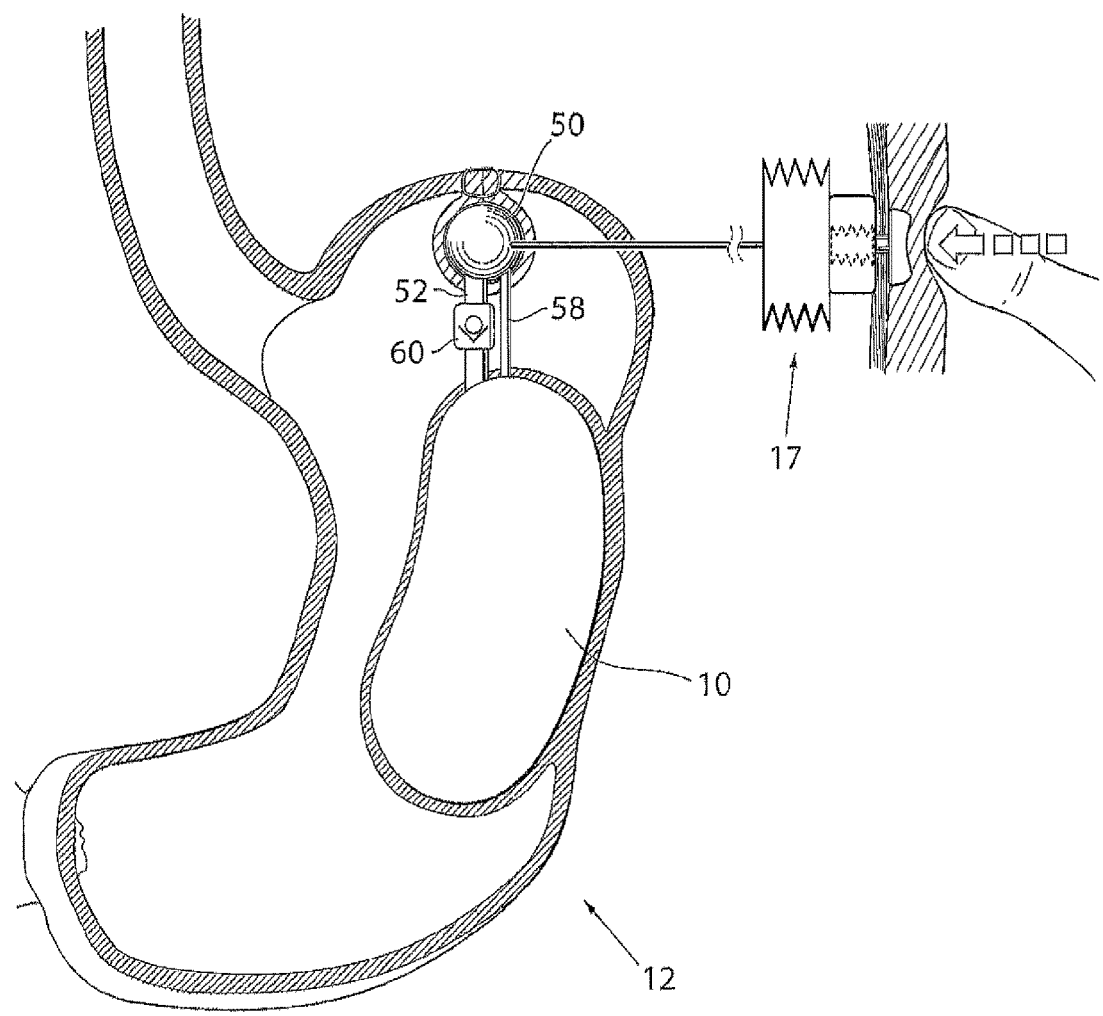

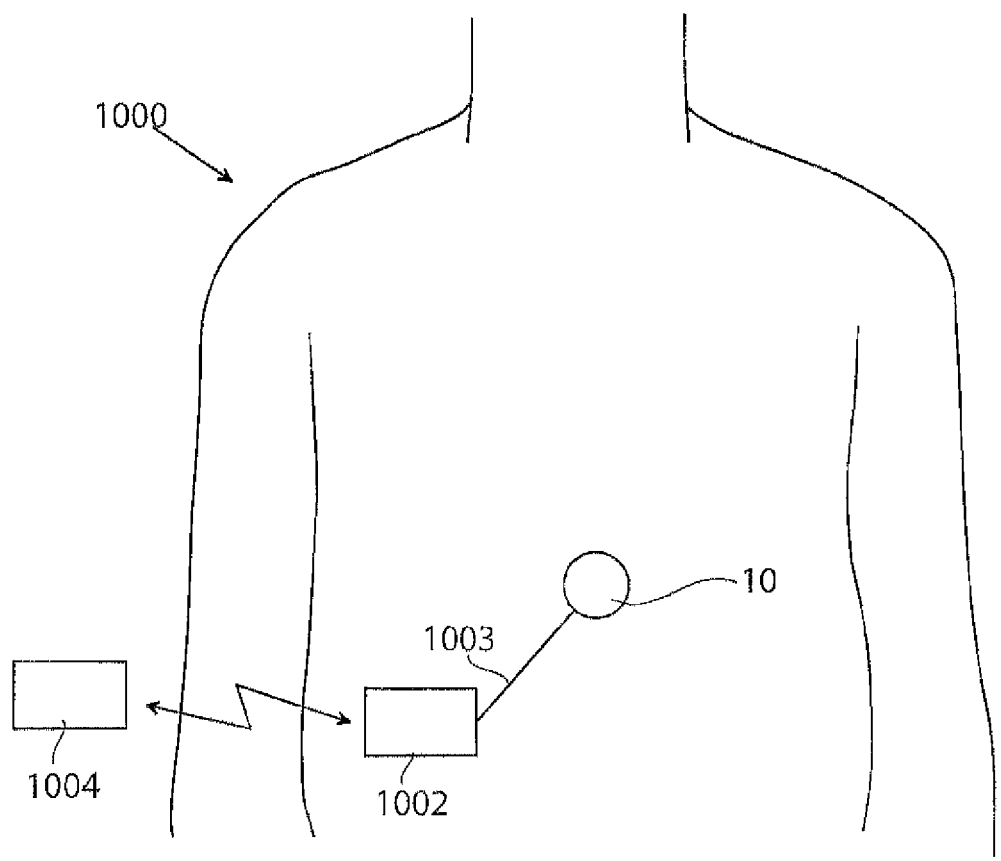

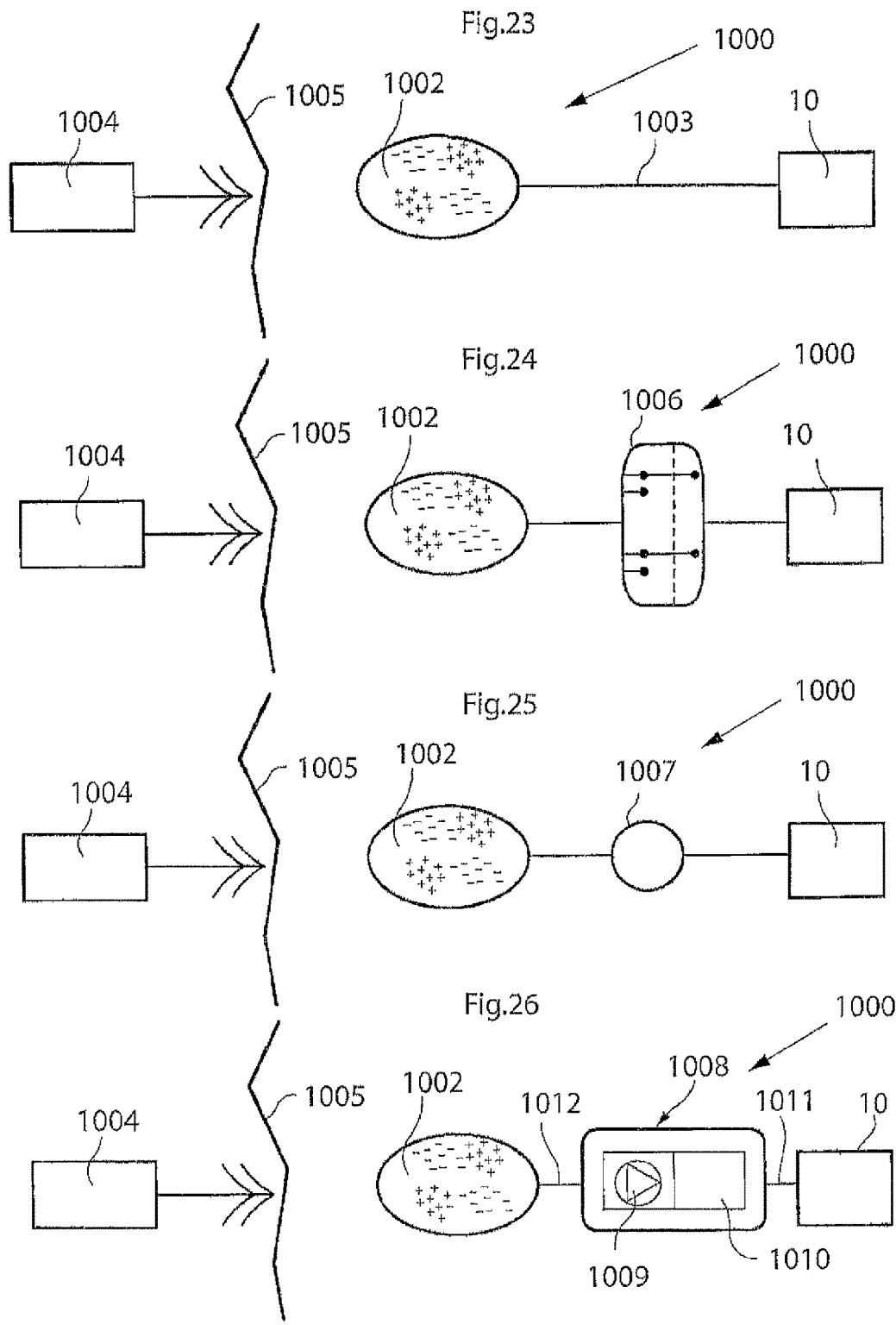

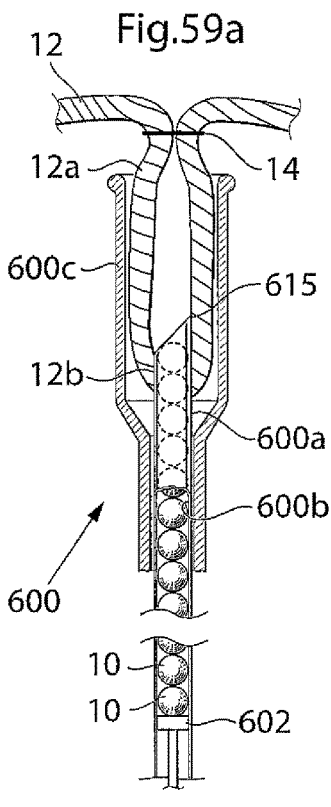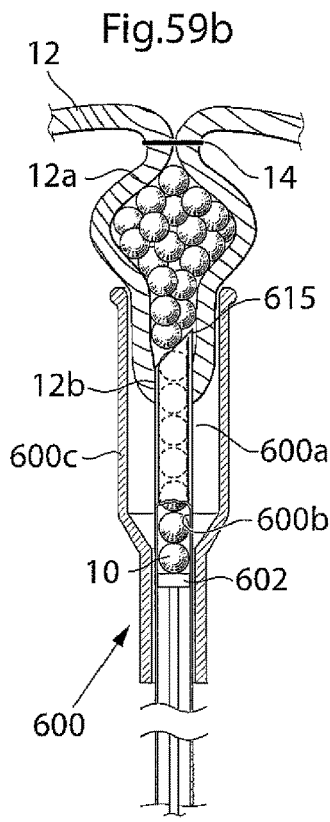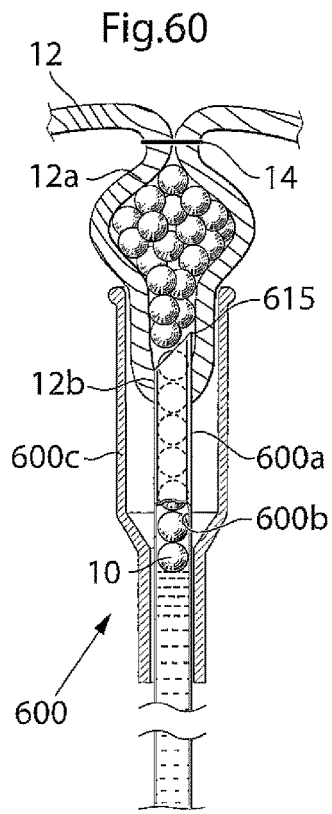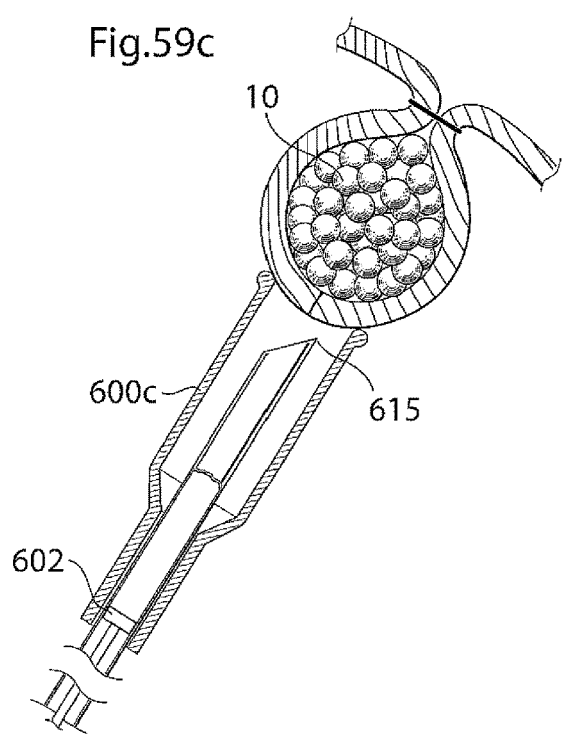

OBESITY TREATMENT

This application is the U.S. national phase of International Application No. PCT/SE2010/050101, filed 29 Jan. 2010, which designated the U.S. and claims priority to International Application Nos. PCT/SE2009/000047, filed 29 Jan. 2009; PCT/SE2009/000452, filed 12 Oct. 2009; and PCT/SE2009/051156, filed 12 Oct. 2009, and to Swedish application No. 0901007-5, filed 17 Jul. 2009; and claims the benefit of U.S. Provisional Application No. 61/213,813, filed 17 Jul. 2009, the entire contents of each of which are hereby incorporated by reference.

TECHNICAL FIELD

The present invention relates to an apparatus, a system, and a method for treating obesity.

BACKGROUND ART

Obesity has been treated by gastric banding a band placed around the stomach to create a stoma, a restricted opening, to restrict the flow of food down to below the band. There has also been tried to use electrical stimulation of the stomach wall to cause the patient to feel satiety.

When the stomach gets distended the patient gets a feeling that the stomach is full.

Another prior art way of treating obesity is to insert a balloon-like object into the stomach of the patient. In this way, the patient is given the feeling of satiety much more quickly when eating, preventing excessive intake of food. However, these prior art balloon-like objects are subject to stomach acids, leading to their destruction within a couple of months of use.

An example of a prior art inflatable gastric device for treating obesity is disclosed in U.S. Pat. No. 4,246,893 to Berson. In this document, it is disclosed an abdominal method wherein an inflatable balloon is surgically implanted in the abdominal cavity of the patient adjacent to the stomach. An adjusting port is provided subcutaneously and the balloon is subsequently inflated by means of inserting a hypodermic needle through the skin of the patient into the adjusting port and introducing a fluid under pressure into the port for passage into the balloon to distend the upper abdomen, compressing the stomach and thereby producing a sense of satiety.

SUMMARY OF INVENTION

The object of the present invention to provide obesity treatment apparatus, system and methods with improved long term properties.

This object and others are obtained by an apparatus described in the appended claims. In general terms, the present invention relates to an apparatus for treating obesity in a human or animal mammal patient comprising two or more volume filling device segments adapted to form an implantable volume filling device, preferably of a controlled size. The volume filling device is adapted to be at least substantially be invaginated by a stomach wall portion of a patient, wherein said volume filling device is adapted to be placed with the outer surface of the device resting against the stomach wall, such that the volume of the food cavity is reduced in size by a volume substantially exceeding the volume of the volume filling device, when the volume filling device is invaginated in the stomach wall. The volume filling device is adapted to disassemble into its volume filling device segments if the device leaves its implanted invaginated stomach position and inadvertently penetrates the stomach wall to become located inside the stomach including penetrating the stomach wall to retain a position inside the stomach, wherein said volume filling device segments are adapted to separately pass through the food, thereby reducing risk for causing obstruction/ileus in the patients intestine. Preferably, the volume filling device has a maximum circumference of at least 15 millimeters, and more preferably of at least 30 millimeters. Preferably, the volume filling device segments has at least part of an outer surface including a biocompatible material. By invaginating a volume filling device by the stomach wall on the outside thereof this device is protected from the stomach acids and will thus remain functioning for a very long time.

According to one alternative, the volume filling device is adapted to be placed inside the stomach with the outer surface of the volume filling device resting against the inside of the stomach wall, such that the volume of the food cavity is reduced in size by a volume exceeding the volume of the volume filling device. The volume filling device is preferably adapted to be placed inside the stomach with a gastroscope.

According to another alternative, the volume filling device is adapted to be placed on the outside of the stomach wall with the outer surface of the volume filling device resting against the outside of the stomach wall, such that the volume of the food cavity is reduced in size by a volume substantially exceeding the volume of the volume filling device. Preferably, the volume filling device is adapted to be completely invaginated by the stomach wall of the patient and to be placed outside the stomach wall via a gastroscopic instrument.

To this end the volume filling device segments may comprise an attachment device adapted to co-operate with a gripping instrument. Suitably, the volume filling device is adapted to be non-invasively adjustable postoperatively.

The volume filling device preferably is adapted to disassemble into its segments if it leaves its placed with the outer surface of the device resting against the stomach wall, i.e. its implanted at last partially invaginated position. The segments are preferably adapted to separately pass through the food passage way, thereby reducing risk of causing obstruction/ileus in the patient's intestine. The volume filling device segments can be adapted to pass through a trocar, for assembly and implantation of said volume filling device into the abdominal cavity. The volume filling device segments can have a flexible outer shape adapted to pass through a trocar. The volume filling device segments can be adapted to have a shape allowing them to be assembled into or form the volume filling device when implanted. In embodiment, at least one of the volume filling device segments have flexible outer surface. In one embodiment, at least one of the volume filling device segments comprises a rigid outer surface. In one embodiment, at least one of the volume filling device segments is hollow with a flexible outer surface. In one embodiment at least one of the volume filling device segments comprises an enclosure wall defining a chamber. At least one of the volume filling device segments can be adapted to be filled with at least one of a fluid, a foam, a gel or a fluid that hardens to a solid material. In one embodiment the volume filling device segments comprises a homogenous and/or solid material, for example a solid body. In one embodiment at least one of said segments comprises a flexible, non-elastic material. In one embodiment at least of said segments comprises a inflatable chamber and at least one tube connected thereto for supplementation of fluid to the chamber. It is preferred that the volume filling device segments are adapted to temporary be holding their assembled position, preferably by the invaginated stomach wall, or alternatively by an adhesive.

For its assembly, the volume filling device is provided with at least one assembly element that sufficiently fits with at least one assembly element of another segment, so the segments by fitting assembly elements can be assembled into the implantable volume filling device. Preferably, the segments for this purpose comprise a core part and a plurality of outer parts, and preferably, the at least one assembly element is selected among sufficiently fitting flanges and slits. The core part is adapted to receive and assemble the outer elements into an implantable volume filling device, and preferably the core part has assembly slits adapted to receive corresponding assembly flanges of the outer parts when assembling the volume filling device. In one embodiment the slits are distributed around the outer peripheral area of the core part. The outer parts are then provided with flanges sufficiently matching the slits to assemble the device. In another embodiment, the at least one assembly element immobilizes each of the volume filling device segments to a core part along a first plane, and wherein movement, and wherein the volume filling device segments and the core part further comprises a second assembly element, which following the assembly of said segments and core part; immobilize each segment and core part along a second plane in an angle to said first plane. For example, the first plane and the second plane can be substantially perpendicular. The second assembly element comprises mating elements, preferably with matching protrusions and recesses provided on the volume filling device segments and the core part, while the at least one assembly element further comprises protrusions and recesses. Preferably, the at least one assembly element comprises an assembly slit in the core part and an assembly flange in a segment, and wherein a mating element comprises a protrusion in said slit and a recess in said flange; or alternatively, the at least one assembly element comprises an assembly flange in the core part and an assembly slit in a segment, and wherein the a mating element comprises a protrusion in said slit and a recess in said flange.

In one particular embodiment, the apparatus preferably further comprises a guiding device, operable for assembling the volume filling device segments to an implantable volume filling device. Preferably, the guiding device is an operation wire operably connected to the segments.

The operation wire can be made of a material that is biodegradable in contact with the body fluid in the abdominal cavity so as to facilitate disassembly of the volume filling device into its segments. In order to assist with assembly procedure, each segment can be provided with at least one assembly element that sufficiently fits with at least one assembly element of another segment, so the segments by fitting assembly elements can be assembled into or form the implantable volume filling device. In one embodiment the segments comprise a core part and a plurality of outer parts and in one embodiment wherein the assembly elements are selected among sufficiently fitting flanges and slits. The core part preferably is adapted to receive and assemble the outer elements into an implantable volume filling device. In one embodiment the core part has assembly slits adapted to receive corresponding assembly flanges of the outer parts when assembling the volume filling device. Preferably the slits are distributed around the outer peripheral area of the core part. The slits and flanges may be designed to have loose fit adapted keep the segments together as a volume filling device at its implanted located, but assist with disassemble the device if it inadvertently leaves such a position, for example to the stomach cavity. In such event the degradation of the guiding device will also assist with disassembling the volume filling device into segments which are designed not cause any obstructions or in any other form damage the patient.

In order to assemble the segments, the operation wire is connected to the core part and to the outer parts so the outer parts can be sequentially assembled to the core part so as to assemble the volume filling device. For this purpose, the operation wire preferably is connected to the assembly flanges of the outer part and preferably, the core part is provided with at least one operation channel for receiving the operation wire. Preferably, each outer part is connected to two operation channels by the operation wire. In one embodiment, a first operation channel has a first orifice in an end surface of the core part and second orifice in a first slit of the core part, so when displacing the operation wire received in said first operation channel in a direction from said end surface, a first outer part is assembled to said core part. A second operation channel has two orifices in a second slit of the core part, so when displacing the operation wire connected to the first operation cannel in a directed from the end surface, a second outer part is assembled to said core part. Preferably, the guiding wire protrudes from the first channel orifice so it can be operated on with an instrument to displace the guiding wire and a first outer element so its assembly flange fits with its designated first assembly slit on the core element, and in a predetermined sequence in the same manner displacing the remaining outer elements so as to assemble the implantable volume filling device. The segments can comprise three or more outer parts assembled to designated slits of the core part with the guiding wire through operation channels having orifices in each designated slit of said core part. In one embodiment the volume filling device comprises one core part and four outer parts. However other ways of designing the segments within the present concept is feasible according to the skilled person. The so assembled volume filling device can retain a generally spherical form, but as will be described later other shapes and additional function elements are made part of the present invention.

The apparatus may comprise a fixation device, suitably two or more fixation devices, adapted to be involved in the fixation of the volume filling device to the stomach wall. The volume filling device including at least one of its segments may comprise a holding device adapted to be held by an instrument, suitably two or more holding devices, to simplify the implantation of the device.

At least a part of the volume filling device may be made of a material which is not destructible by stomach acid. The volume filling device may be destructible by acids, for example hydrochloric acid.

In an embodiment, the volume filling device including at least one of its segments is inflatable to an expanded state and comprises an enclosure wall defining a chamber, wherein the volume filling device is inflated with a gel or fluid supplied into the chamber. At least one tube may be connected to the volume filling device for supplying gel or fluid to the chamber. An injection port connectable with the tube may be provided. Alternatively, the volume filling member may be provided with an inlet port for a fluid or a gel connectable to a gastroscopic instrument, wherein the inlet port comprises a fluid connection adapted to interconnect the inflatable device and the gastroscopic instrument.

The volume filling device may include a homogenous material, such as gel having a shore value of less than 15. The device may also be a solid body.

The volume filling device including at least one of its segments may comprise a rigid, elastic or flexible outer surface. Where the outer surface is rigid, it is rigid enough to maintain non-deformed when subject to forces created by stomach movements. The volume filling device may comprise a flexible non-elastic material.

In accordance with a first general design of the volume filling device, the device has a maximum circumference as seen in a plane perpendicular to an axis through the device. The circumferences of the device as seen in other planes perpendicular to said axis are equal to the maximum circumference or decrease as seen along said axis in the direction from the maximum circumference. For example, the device may be substantially egg shaped, spherically shaped, or substantially shaped like an egg with an indented middle section or like a bent egg.

In accordance with a second general design of the device, the circumference of the device as seen in a plane perpendicular to an axis through the device increases and decreases at least two times as the plane is displaced along said axis, or decreases and increases at least one time as the plane is displaced along said axis. For example, the device may be substantially shaped like a kidney.

The volume filling device in yet another embodiment has a circumference as seen in a plane perpendicular to an axis through the body, and wherein the circumference constantly increases or remains constant when moving along said axis from a first end point of said axis to a intermediate point with a maximum, and the circumference constantly decreases or remains constant when moving from said intermediate point to a second end point of said axis.

The volume filling device in yet another embodiment has a circumference as seen in a plane perpendicular to an axis through the body, and wherein the circumference constantly increases or remains constant when moving along said axis from a first end point of said axis to a first intermediate point with a first maximum, the circumference constantly decreases or remains constant when moving from said first intermediate point to a second intermediate point with a first minimum, the circumference constantly increases or remains constant when moving along said axis from said second intermediate point of said axis to a third intermediate point with a second maximum, and the circumference constantly decreases or remains constant when moving from said third intermediate point to a second end point of said axis.

More embodiments are described below:

The volume filling device and/or one or more of the volume filling device segments may have an elongated, rounded, bent and/or curved shape.

The volume filling device has a circumference of at least 30, 50, 80 120, 150, 180 or 220 mm.

The volume filling device has a volume in the range of 0.0001 to 0.001 $m^3$, or 0.00001 to 0.001 $m^3$, or 0.00001 to 0.0002 $m^3$. The volume of the volume filling device has in yet another embodiment a volume of less than 0.0002 $m^3$.

The volume filling device may comprise at least two interconnectable portions adapted to be placed inside the stomach as separate portions.

The volume filling device including at least one of its segments may comprise an elastic material, a bio-compatible material and/or silicone.

Suitably, the volume filling device is provided with at least one layer. For example, a metal layer, a Parylene layer, a polytetrafluoroethylene layer or a polyurethane layer. The layers may comprise multiple layers in any order. Suitably, one of the layers may be made of made of metal, silicon or PTFE. The volume filling device may comprise an outer surface layer of silicone, polyurethane, Teflon®, or polytetrafluoroethane, metal, Parylene, PTFE or a combination thereof. The volume filling device may comprise an inner surface layer of silicone, polyurethane, Teflon®, or polytetrafluorethylene, metal, Parylene, PTFE or a combination thereof. Other combinations include an inner surface layer of polytetrafluoroethylene and an outer layer of silicone, an inner surface layer of polytetrafluoroethylene, an intermediate layer of silicone, and an outer layer of Parylene, an inner surface layer of polyurethane and an outer layer of silicone, and an inner surface layer of polyurethane, an intermediate layer of silicone, and an outer layer of Parylene.

The volume filling device including at least one of its segments may comprise a fluid adapted to be transformed into solid state or fixed form. Such a fluid may be liquid polyurethane or isotonic. The fluid may comprises large molecules, such as iodine molecules, to prevent diffusion.

The volume filling device may have a maximum circumference of at least 50 millimeters, preferably at least 80 millimeters. Suitably, the volume filling device is deformable to a maximum diameter, so as to be insertable into a laparoscopic trocar.

Preferably, the volume filling device is adapted to be kept in place by stomach-to-stomach sutures or staples to invaginate the device in the stomach wall. Advantageously, the volume filling device has varying circumference to better be kept in place invaginated in the stomach wall of the patient. The stomach-to-stomach sutures or staples may be provided with fixation portions exhibiting a structure adapted to be in contact with the stomach wall to promote growth in of human tissue to secure long term placement of the volume filling device attached to the stomach wall. The structure may comprise a net like structure.

In embodiment of the invention, the apparatus comprises a stretching device placed outside the stomach wall and adapted to stretch a portion of the stomach wall, thereby affecting the patient's appetite. Where the volume filling device including at least one of its segments is inflatable, the apparatus may comprise a fluid connection interconnecting the stretching device and the volume filling device.

In an embodiment, the apparatus comprises at least one operable stretching device implantable in an obese patient and adapted to stretch a portion of the patient's stomach wall and an operation device for operating the stretching device when implanted to stretch the stomach wall portion such that satiety is created.

In an embodiment, the apparatus comprises at least one operable stretching device implantable in the patient and adapted to stretch a portion of the patient's stomach wall, and an implantable control unit for automatically controlling the operable stretching device, when the control unit and stretching device are implanted, to stretch the stomach wall portion in connection with the patient eating such that satiety is created.

In an embodiment, the apparatus comprises at least one operable stretching device implantable in an obese patient and adapted to stretch a portion of the patient's stomach wall, wherein said stretching device comprising an expandable stretching reservoir and an operation device for operating the stretching device when implanted to stretch the stomach wall portion, wherein the volume filling device is inflatable and in fluid connection with said stretching reservoir, wherein said operation device comprises a pump for pumping fluid between said main reservoir and said stretching reservoir to stretch said stomach wall portion such that satiety is created. A control device may be provided for controlling said stretching device including said pump. The control device may comprise a wireless remote control adapted to control the stretching device from the outside of the patient's body, or an implantable control unit for controlling said stretching device. Alternatively, the control device may comprise a subcutaneously placed switch or reservoir adapted to control the stretching device from the outside of the patient's body. A sensor or sensing device to be implanted in the patient body may be provided, wherein the implantable control unit is adapted to control the stretching device from the inside of the patient's body using information from said a sensor or sensing device, adapted to sense, director indirect, the food intake of the patient.

In an embodiment, the volume filling device comprises a main volume filling reservoir, a stretching device comprising at least one operable stretching device implantable in an obese patient and adapted to stretch a portion of the patient's stomach wall, wherein said stretching device comprising an expandable reservoir, adapted to be invaginated in the stomach wall at the upper part of the stomach, higher up than the inflatable main volume filling device when the patient is standing, wherein the volume filling device is inflatable and in fluid connection with said stretching reservoir, wherein normal contractions of the stomach wall, related to food intake, cause fluid to flow from said invaginated main volume filling reservoir lower placed onto the stomach wall adapted to cause said stretching reservoir to stretch said stomach wall portion such that satiety is created. The fluid connection between the main volume filling device reservoir and the stretching reservoir comprises a non-return valve. The fluid connection between the main volume filling device reservoir and the stretching reservoir comprises a release function adapted to release the volume in the stretching reservoir back to the main volume filling device reservoir. Said release function may comprise a fluid return connection of a substantially smaller area than said fluid connection, to slowly release back fluid to said main volume filling device reservoir from the stretching reservoir to release said stretching of the stomach wall portion. A further manual control device comprising a subcutaneously placed reservoir adapted to control the stretching device from the outside of the patient's body may be provided to further affect the stretching device to stretch the stomach wall portion.

In an embodiment, the a main volume filling device reservoir adapted to be inflatable may be provided, wherein the volume filling device further comprises an expandable structure, adapted to expand, when the device is invaginated in the stomach wall, wherein said structure comprising a bellow adapted to take into account the fibrosis surrounding the device when implanted, such that the movement of the bellow is substantially un-affected of said fibrosis.

In an embodiment, the apparatus comprises a stretching device comprising at least one operable stretching device implantable in an obese patient and adapted to stretch a portion of the patient's stomach wall and wherein the stretching device comprising a expandable structure, adapted to expand and stretch the stomach wall portion, when the device is invaginated in the stomach wall, wherein said structure comprising a special bellow adapted to take into account the fibrosis surrounding the device when implanted, such that the movement of the bellow is substantially un-affected of said fibrosis. An operation device for operating the stretching device may be provided to stretch the stomach wall portion such that satiety is created. The apparatus may comprise an implantable control unit for automatically controlling the operable stretching device, when the control unit and stretching device are implanted, to stretch the stomach wall portion in connection with the patient eating such that satiety is created.

In an embodiment, the apparatus comprises a stretching device comprising at least one operable stretching device implantable in an obese patient and adapted to stretch a portion of the patient's stomach wall such that satiety is created. The control device may comprise a wireless remote control adapted to control the stretching device from the outside of the patient's body or an implantable control unit for controlling said stretching device. Alternatively, said control device may comprise a subcutaneously placed switch or reservoir adapted to control the stretching device from the outside of the patient's body. A sensor or sensing device adapted to be implanted in the patient body may be provided, wherein the implantable control unit is adapted to control the stretching device from the inside of the patient's body using information from said sensor or sensing device, adapted to sense, direct or indirect, the food intake of the patient.

In an embodiment, the apparatus further comprises a stretching device comprising three or more mechanical parts engaged with different parts of the stomach wall, one part each, wherein said engagement includes suturing or stapling to the stomach wall or invaginating the mechanical parts in the stomach wall part with stomach to stomach sutures, wherein the three or more mechanical parts are adapted to move in relation to each other adapted to stretch three different wall portions, the stretching device further adapted to having said wall portions stretched independently from each other both regarding force used for stretching the stomach wall portion as well as, time periods the stretching is applied, and when the stretching is applied.

In an embodiment, the apparatus further comprises a stretching device comprising two or more hydraulic parts engaged with different parts of the stomach wall, one part each, wherein said engagement includes suturing or stapling to hydraulic part to the stomach wall or invaginating the hydraulic parts in the stomach wall part, with stomach to stomach sutures, wherein the two or more hydraulic parts are adapted to move in relation to each other adapted to stretch three different wall portions, the stretching device further adapted to having said wall portions stretched independently from each other both regarding force used for stretching the stomach wall portion as well as, time periods the stretching is applied, and when the stretching is applied.

In an embodiment, the apparatus further comprises a stretching device is engaged with a part of the stomach wall, including suturing or stapling the stretching device to the stomach wall or invaginating the stretching device in the stomach wall part, with stomach to stomach sutures, wherein the stretching device is further adapted to stretch a stomach wall portion controlling force used for stretching the stomach wall portion as well as, time periods the stretching is applied, and when the stretching is applied.

In an embodiment, the apparatus further comprises a stretching device comprising two parts engaged with different parts of the stomach wall, one part each, wherein said engagement includes suturing or stapling the parts to the stomach wall or invaginating the parts in the stomach wall part, with stomach to stomach sutures, wherein the stretching device further adapted to have different wall portions stretched independently from each other controlling force used for stretching the stomach wall portion as well as, time periods the stretching is applied, and when the stretching is applied.

In an embodiment, the apparatus is further adapted to treat reflux disease. To this end, it further comprises an implantable volume filling device adapted to be at least partly invaginated by the patient's stomach fundus wall and having an outer surface that includes a biocompatible material, wherein a substantial part of the outer surface of the volume filling device is adapted to rest against the stomach wall without injuring the latter in a position between the patient's diaphragm and at least a portion of the lower part of the invaginated stomach fundus wall, such that movement of the cardiac notch of the patient's stomach towards the patient's diaphragm is restricted, when the volume filling device is invaginated, to thereby prevent the cardia from sliding through the patient's diaphragm opening into the patient's thorax, so as to maintain the supporting pressure against the patients cardia sphincter muscle exerted from the patient's abdomen, the volume filling device having a size of at least 125 mm$^3$ and a circumference of at least 15 mm.

In another embodiment, the apparatus is further adapted to treat reflux disease. To this end, it further comprises an implantable volume filling device having an outer surface including a biocompatible material, wherein the movement restriction device is adapted to rest with at least a part of its outer surface against the patient's stomach fundus wall, in a position between the patient's diaphragm and the fundus wall, such that movement of the cardiac notch of the patient's stomach towards the patient's diaphragm is restricted, when the movement restriction device is implanted in the patient, to thereby prevent the cardia from sliding through the patient's diaphragm opening into the patients thorax, so as to maintain the supporting pressure against the patients cardia sphincter muscle exerted from the patient's abdomen, wherein the volume filling device having a size of at least 125 mm3 and a circumference of at least 15 mm, and an fixation device adapted to secure the volume filling device in said position, when the volume filling device is implanted.

In another embodiment, the apparatus is further adapted to treat reflux disease. To this end, it further comprises an implantable movement restriction device adapted to be at least partly invaginated by the patient's stomach fundus wall and having an outer surface that includes a biocompatible material, wherein a substantial part of the outer surface of the movement restriction device is adapted to rest against the stomach wall without injuring the latter in a position between the patient's diaphragm and at least a portion of the lower part of the invaginated stomach fundus wall, such that movement of the cardiac notch of the patient's stomach towards the patient's diaphragm is restricted, when the movement restriction device is invaginated, to thereby prevent the cardia from sliding through the patient's diaphragm opening into the patient's thorax, so as to maintain the supporting pressure against the patient's cardia sphincter muscle exerted from the patient's abdomen, the movement restriction device having a size of at least 125 mm3 and a circumference of at least 15 mm, further comprising a stretching device comprising at least one operable stretching device implantable in the obese patient and adapted to stretch a portion of the patient's stomach wall such that satiety is created.

In another embodiment, the apparatus is further adapted to treat reflux disease. To this end, it further comprises an implantable movement restriction device having an outer surface including a biocompatible material, wherein the movement restriction device is adapted to rest with at least a part of its outer surface against the patient's stomach fundus wall, in a position between the patient's diaphragm and the fundus wall, such that movement of the cardiac notch of the patients stomach towards the patient's diaphragm is restricted, when the movement restriction device is implanted in the patient, to thereby prevent the cardia from sliding through the patient's diaphragm opening into the patients thorax, so as to maintain the supporting pressure against the patient's cardia sphincter muscle exerted from the patient's abdomen, wherein the movement restriction device having a size of at least 125 mm$^3$ and a circumference of at least 15 mm, and a fixation device adapted to secure the movement restriction device in said position, when the movement restriction device is implanted, further comprising a stretching device comprising at least one operable stretching device implantable in the obese patient and adapted to stretch a portion of the patients stomach wall such that satiety is created.

In an embodiment, the apparatus further comprises an external control unit for controlling the volume filling device from the outside of the patient's body. The external control unit may comprise a wireless remote control adapted to control the device from the outside of the patient's body. Alternatively, the external control unit may comprise a subcutaneously placed switch or reservoir adapted to control the device from the outside of the patient's body.

In an embodiment, the apparatus further comprises a sensor or sensing device adapted to be implanted in the patient body, wherein the implantable control unit is adapted to control the device from the inside of the patient's body using information from said a sensor or sensing device, adapted to sense, direct or indirect, the food intake of the patient.

In accordance with another aspect of the present invention, there is provided an apparatus for treating obesity of an obese patient having a stomach with a food cavity, the apparatus comprising at least one volume filling device adapted to be at least substantially invaginated by a stomach wall portion of the patient and having an outer surface that includes a biocompatible material, wherein the volume filling device is adapted to be placed inside the stomach with the outer surface of the volume filling device resting against the inside of the stomach wall, such that the volume of the food cavity is reduced in size by a volume substantially exceeding the volume of the volume filling device, the volume filling device having a maximum circumference of at least 30 millimeters.

In a preferred embodiment, the apparatus comprises at least one switch implantable in the patient for manually and non-invasively controlling the volume filling device.

In another preferred embodiment, the apparatus comprises a wireless remote control for non-invasively controlling the volume filling device.

In a preferred embodiment, the apparatus comprises a hydraulic operation device for operating volume filling device.

In one embodiment, the apparatus comprises comprising a motor or a pump for operating the volume filling device.

In one embodiment the apparatus comprises an adjustment device for adjusting the size and/or shape of the volume filling device including at least one of its segments. The size of the volume filling device can be hydraulically adjustable and the adjustment device comprises a hydraulic fluid reservoir that, when implanted in the patient, is connected to at least one of the volume filling device segments, and wherein the size of the volume filling device is non-invasively regulated by moving hydraulic fluid from the reservoir to at least one volume filling device segment, thereby adjusting the size of at least one segment of the volume filling device. The apparatus can further comprise hydraulic regulation device comprising at least one chamber that, when implanted in the patient, is invaginated in the patient's stomach wall with the volume filling devices and in being connection therewith, and wherein the amount of hydraulic fluid contained in at least one of the volume filling device segments is non-invasively regulated by distributing fluid between the hydraulic reservoir and the at least one chamber. Preferably, the at least one chamber, when implanted in the patient, is filled with the hydraulic fluid using a pump in the reservoir so as to stretch the fundus wall to create satiety in the patient. The adjustment device can further comprise a reverse servo comprising three adjustable reservoirs with hydraulic fluid, wherein a small volume of fluid in a first reservoir placed subcutaneously, being part of a first closed system including a second reservoir, is compressed with a high force per area unit for moving a small volume of hydraulic fluid, and wherein the second reservoir affects a larger volume of hydraulic fluid in a third reservoir, the third reservoir being part of a second closed system having larger volume than said first reservoir, thereby creating a movement of a larger total volume of hydraulic fluid with less force per area unit. The apparatus of the discussed embodiment can comprise a wireless remote control, wherein the volume filling device, when implanted in the patient, is non-invasively regulated by the wireless remote control. The apparatus of the discussed embodiment can further comprise an energy source that powers the adjustable volume filling device when implanted in a patient. The energy source preferably comprises an internal energy source implantable in the patient. The energy source can also comprise an external energy source transmitting wireless energy. The internal energy source, when implanted in the patient can be chargeable by the wireless energy transmitted by the external energy source. The wireless remote control can comprise at least one external signal transmitter and receiver, further comprising an internal signal receiver and transmitter implantable in the patient for receiving signals transmitted by the external signal transmitter and sending feedback signals back to the remote control. The wireless control signal can comprise an electric or magnetic field, or a combined electric and magnetic field.

In one embodiment, the apparatus comprises a wireless energy transmitter for non-invasively energizing any part of the apparatus in need of energy supplementation. The energy transmitter preferably transmits energy by at least one wireless energy signal. Preferably, the wireless energy comprises a wave signal or a field, or the wireless energy signal can comprise an electric or magnetic field, or a combined electric and magnetic field. The wave signal preferably is selected from the group consisting of: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. The apparatus of this embodiment can further comprise an implantable accumulator and an energy transforming device transforming wireless energy to electric energy, wherein the electric energy is used at least partly to charge the accumulator or to run any energy consuming part of the apparatus direct from the energy transforming device.

In one embodiment, the apparatus comprises a sensor sensing a parameter, a functional parameter or a physical parameter of the patient. The functional parameter is correlated to a wireless transfer of energy for charging an internal energy source implantable in the patient. The apparatus can further comprise a feedback device that, when implanted in the patient, sends feedback information from inside the patient's body to the outside thereof, the feedback information being related to the functional parameter. The apparatus can also comprise an implantable internal control unit for controlling the volume filling device in response to the sensor sensing the functional parameter. The sensor for sensing the physical parameter is a pressure sensor or a motility sensor. An implantable internal control unit can control o the volume filling device of the apparatus in response to the sensor sensing the physical parameter.

In one embodiment, the apparatus comprises an operation device for operating the volume filling device in order to control its size and/or shape. For this purpose, the operation device can comprise a motor or a pump.

In one embodiment of the apparatus, the volume filling device is adapted to further receive wireless energy, wherein the wireless energy is used to power the operation device to create kinetic energy for the operation of the volume filling device. The wireless energy can for example be used to directly power the operation device to create kinetic energy for the operation of the volume filling device, as the wireless energy is being transmitted by the energy transmission device. The volume filling device may also be adapted to receive energy from an energy transforming device directly during wireless energy transfer or from an energy accumulator, being rechargeable by the wireless energy and energy transforming device. The wireless energy, preferably comprises a wave signal that is selected from the group consisting of: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. The wireless energy signal can also comprise an electric or magnetic field, or a combined electric and magnetic field.

In one embodiment of the apparatus it further comprises implantable electrical components including at least one voltage level guard, or at least one constant current guard.

In one embodiment of the apparatus, at least one of the volume filling device segments has at least one flat surface. Preferably, the volume filling device segments has the shape of a polyhedron, preferably one of the following shapes: tetrahedron, hexahedron, octahedron, dodecahedron and icosahedrons.

In one embodiment of the apparatus, a friction enhancing material is provided. This increases the friction between adjacent volume filling device segments, thereby stabilizing the volume filling device. This friction enhancing material is preferably a glue or an adhesive. Alternatively, at least one of the volume filling device segments has a surface with a rugged texture.

In one embodiment of the apparatus, at least one of the volume filling device segments has spherical shape. Alternatively, it has at least one flat surface.

In an alternative embodiment, the apparatus comprises a fluid for reducing the friction between adjacent volume filling device segments. The volume filling device can thereby more easily adapt its shape to the movements of the patient's body.

The apparatus may in one embodiment comprise a friction reducing material on the outer surface of the volume filing device segments. This friction reducing material may be a fluid reducing the friction between adjacent volume filling device segments.

The apparatus may comprise an expandable second volume filling device segment for enclosing two or more first volume filling device segments different from the second volume filling device segment, wherein the second volume filling device segment and the first volume filling device segments together form the volume filling device. In one alternative, the second volume filling device segment comprises a friction reducing material on an inner surface thereof, the friction reducing material being in contact with the first volume filling device segments, when implanted.

The second volume filling device segment may be adapted to be filled with a fluid to allow mutual movement between adjacent first volume filling device segments so that the shape of the volume filling device adapts to stomach wall movements, when said volume filling device is invaginated in a stomach wall. It is then preferred that at least a wall portion of the second volume filling device segment is flexible or stretchable.

The fluid provided in the volume filling device may be isotonic or hypertonic.

The volume filling device segments may be adapted to be inserted into a pouch formed by part of a stomach wall of the patient. The volume filling device segments may be adapted to be filled, directly or indirectly, into the pouch formed by part of a stomach wall of the patient via a tubular instrument.

In one embodiment, the volume filling device comprises a solidifying liquid.

This liquid or fluid may be supplied to the pouch by means of a conduit.

In one embodiment, the plurality of volume filling device segments are adapted to be interconnected to form the volume filling device, after said plurality of volume filling device segments have been inserted into a human or artificial pouch.

The apparatus, wherein the volume filling device segments adapted to be assembled to an implantable volume filling device.

The volume filling device segments are preferably adapted to form an implantable volume filling device of a controlled size. In general terms any applicable feature or embodiment or part of embodiment or method described herein are, when applicable, valid for both the volume filling device as well as for the volume filling device segments.

An operational method to be combined in any way using any apparatus, part of apparatus or system or part of system or any claimed embodiment described anywhere in this document.

A method or part of method to be used in any combination and using any apparatus or part of apparatus or any feature in any combination where the following method steps is applicable, wherein said method may comprise one or more of the following operational method steps:
introducing an instrument into the throat,
passing down the esophagus,
placing an anvil or unit for delivery of fixating members in the esophagus between the cardia and the diaphragm level, for engaging in the fixation of the esophagus to the stomach tissue,
passing down the esophagus and additionally further down into the stomach,
filling the stomach with gas to expand the stomach,
sucking fluid from the stomach,
looking at a guiding vision when said instrument comprising a camera,
engaging the instrument with the stomach,
creating and suturing at least one pouch of the stomach wall,
filling said at least one pouch with a fluid and/or volume filling device or two or more volume filling devices,
deliver a plurality of volume filling devices into said pouch created in the stomach tissue through a tubular member,
passing through the stomach wall with said instrument,
passing through the stomach wall with said instrument for the placement of
a volume filling device on the outside of the stomach wall,
passing through the stomach wall with said instrument for the placement of a tube allowing placement of a subcutaneous injection port,
placing an subcutaneous injection port,
suturing or stapling the stomach wall from the inside thereof to the esophagus,
suturing or stapling the stomach wall to stomach wall from the inside of the stomach,
engaging the instrument with the esophagus,
suturing or stapling one layer of stomach tissue to one layer of esophageal tissue,
suturing or stapling two layers of stomach tissue to one layer of esophageal tissue,
suturing or stapling three layers of stomach tissue to one layer of esophageal tissue,
suturing or stapling four layers of stomach tissue to one layer of esophageal tissue,
suturing or stapling one or more layers of stomach tissue to two or more positions on the esophageal tissue, the esophagus having an esophagus center axis, the esophagus further having an inner and outer substantially cylindrical surface extending radially in relation to the esophagus center axis and wherein the stomach tissue is attached to esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis,
delivering fixating members by a unit placed on said instrument,
penetrating at least one layer of stomach tissue and one layer of esophagus tissue with said fixating members,
placing said fixating members above the gastro-esophageal junction for creating a tunnel between the esophagus and stomach above said junction,
placing an esophagus part in the esophagus and a stomach part in the stomach,
placing the fixating member substantially between the stomach and esophagus part,
inserting said instrument into the main stomach cavity through the cardia and adapted to direct the instrument in cranial direction to reach a position of said unit above said junction,
allowing the tunnel a substantially unrestricted contraction and release of the cardia closing sphincter muscle placed in said junction, when such a tunnel has been created.

A method or part of method to be used in any combination and using any apparatus or part of apparatus or any feature in any combination where the following method steps is applicable, wherein said method comprises one or more of the following operational method steps:
cutting the skin of a patient
creating an opening in the abdominal wall of the patient Introducing said instrument into the abdominal cavity through said opening in the abdominal wall,
engaging the instrument with the stomach,
pulling down into the stomach wall for creating at least one pre-shaped pouch of the stomach wall,
clamping the stomach wall for creating at least one pre-shaped pouch of the stomach wall,
suturing or stapling at least one pouch in the stomach wall,
filling said at least one pouch with a fluid and/or volume filling device or two or more volume filling devices,
deliver a plurality of volume filling devices into said pouch created in the stomach tissue through a tubular member,
passing through the stomach wall into the stomach with said instrument,
passing through the stomach wall with said instrument for the placement of a volume filling device on the inside of the stomach wall,
passing through the stomach wall with said instrument for suturing the stomach wall to the esophagus wall,
placing a volume filling device on the outside of the stomach wall,
invaginating said volume filling device in the stomach wall
placing a subcutaneous injection port,
suturing or stapling the stomach wall to stomach wall from the outside of the stomach,
suturing or stapling the stomach wall to stomach wall from the outside of the stomach without penetrating the mucosa,
suturing or stapling two layers of stomach wall to one or two layers of stomach wall,
engaging the instrument with the esophagus,
clamping the on both sides of the esophagus for fixating one layer of esophageal wall to stomach tissue,
clamping the on both sides of the esophagus and the stomach fundus wall for fixating one layer of esophageal wall to one or two layers of stomach tissue,
introducing a tube or a gastroscopic instrument into the esophagus comprising an anvil member or a fixating delivery member involving in the fixation of the esophagus to the stomach,
coordinating the position of the anvil member or a fixating delivery member inside the esophagus to said instrument clamping around the esophagus,
suturing or stapling one layer of stomach tissue to one layer of esophageal tissue,
suturing or stapling two layers of stomach tissue to one layer of esophageal tissue,
suturing or stapling three layers of stomach tissue to one layer of esophageal tissue,
suturing or stapling four layers of stomach tissue to one layer of esophageal tissue,
stapling using staplers of different stapling depths at different positions in a stapler row,
stapling stomach to esophagus with one first stapler depth and stapling stomach to stomach with a second smaller stapler depth,
stapling a pouch with stomach to stomach sutures in a stapler row, further comprising stapling the esophagus with staplers of a larger depth included as a part of said stapler row,
suturing or stapling one or more layers of stomach tissue to two or more positions on the esophageal tissue, the esophagus having an esophagus center axis, the esophagus further having an inner and outer substantially cylindrical surface extending radially in relation to the esophagus center axis and wherein the stomach tissue is attached to esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis,
delivering fixating members by a unit placed on said instrument,
penetrating at least one layer of stomach tissue and one layer of esophagus tissue with said fixating members,
placing said fixating members above the gastro-esophageal junction for creating a tunnel between the esophagus and stomach above said junction,
allowing the tunnel a substantially unrestricted contraction and release of the cardia closing sphincter muscle placed in said junction, when such a tunnel has been created,
placing an esophagus part in the esophagus and a stomach part in the stomach via an introduction into the stomach cavity,
placing the fixating member substantially between the stomach and esophagus part,
inserting said instrument into the main stomach cavity below said junction and adapted to direct the instrument in cranial direction to reach a position of said unit above said junction,
operating a joint comprised in said instrument, for enabling said instrument to be inserted into the main stomach cavity bending said joint in a direction to reach a position of said part of the unit in the esophagus above said junction.

A method or part of method to be used in any combination and using any apparatus or part of apparatus or any feature in any combination where the following method steps is applicable, wherein said method comprises one or more of the following laparoscopic operational method steps:
cutting the skin of a patient
introducing a tube through the abdominal wall,
filling a fluid or gas into the abdominal cavity,
introducing two or more trocars into the abdominal cavity,
introducing a camera into the abdominal cavity through one of the trocars,
introducing said instrument into the abdominal cavity through a trocar,
engaging the instrument with the stomach,
pulling down into the stomach wall for creating at least one pre-shaped pouch of the stomach wall,
clamping the stomach wall for creating at least one pre-shaped pouch of the stomach wall,
suturing or stapling at least one pouch in the stomach wall,
filling said at least one pouch with a fluid and/or a volume filling device or two or more volume filling devices,
deliver a plurality of volume filling devices into said pouch created in the stomach tissue through a tubular member,
passing through the stomach wall into the stomach with said instrument,
passing through the stomach wall with said instrument for the placement of a volume filling device on the inside of the stomach wall,
passing through the stomach wall with said instrument for suturing the stomach wall to the esophagus wall, placing a volume filling device on the outside of the stomach wall,
invaginating said volume filling device in the stomach wall
placing a subcutaneous injection port,
suturing or stapling the stomach wall to stomach wall from the outside of the stomach,
suturing or stapling two layers of stomach wall to one or two layers of stomach wall,
suturing or stapling the stomach wall to stomach wall from the outside of the stomach without penetrating the mucosa,
engaging the instrument with the esophagus,
clamping the on both sides of the esophagus for fixating one layer of esophageal wall to stomach tissue,
clamping the on both sides of the esophagus and the stomach fundus wall for fixating one layer of esophageal wall to one or two layers of stomach tissue,
introducing a tube or a gastroscopic instrument into the esophagus comprising an anvil member or a fixating delivery member involving in the fixation of the esophagus to the stomach,
coordinating the position of the anvil member or a fixating delivery member inside the esophagus to said instrument clamping around the esophagus,
suturing or stapling one layer of stomach tissue to one layer of esophageal tissue,
suturing or stapling two layers of stomach tissue to one layer of esophageal tissue,
suturing or stapling three layers of stomach tissue to one layer of esophageal tissue,
suturing or stapling four layers of stomach tissue to one layer of esophageal tissue,
stapling using staplers of different stapling depths at different positions in a stapler row,
stapling stomach to esophagus with one first stapler depth and stapling stomach to stomach with a second smaller stapler depth,
stapling a pouch with stomach to stomach sutures in a stapler row, further comprising stapling the esophagus with staplers of a larger depth included as a part of said stapler row,
suturing or stapling one or more layers of stomach tissue to two or more positions on the esophageal tissue, the esophagus having an esophagus center axis, the esophagus further having an inner and outer substantially cylindrical surface extending radially in relation to the esophagus center axis and wherein the stomach tissue is attached to esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis,
delivering fixating members by a unit placed on said instrument,
penetrating at least one layer of stomach tissue and one layer of esophagus tissue with said fixating members,
placing said fixating members above the gastro-esophageal junction for creating a tunnel between the esophagus and stomach above said junction,
allowing the tunnel a substantially unrestricted contraction and release of the cardia closing sphincter muscle placed in said junction, when such a tunnel has been created,
placing an esophagus part in the esophagus and a stomach part in the stomach via an introduction into the stomach cavity,
placing the fixating member substantially between the stomach and esophagus part,
inserting said instrument into the main stomach cavity below said junction and adapted to direct the instrument in cranial direction to reach a position of said unit above said junction,
operating a joint comprised in said instrument, for enabling said instrument to be inserted into the main stomach cavity bending said joint in a direction to reach a position of said part of the unit in the esophagus above said junction.

Please note that any embodiment or part of embodiment as well as any method or part of method or any apparatus or part of apparatus or any feature or part of feature or any system or part of system or any figure or part of figure could be combined in any applicable way. All examples herein should be seen as part of the general description and therefore possible to combine in any way in general terms.

It is understood that a skilled person is in the position of combining steps, changing the order of steps, and combining elements of the different embodiments of the invention without inventive effort, and without departing from the scope of the invention as defined in the description and claims.

BRIEF DESCRIPTION OF DRAWINGS

The present invention will now be described in more detail by way of non-limiting examples and with reference to the accompanying drawings, in which:

FIG. 2b is a sectional view taken along line IIb-IIb of FIG. 2a.

FIGS. 3a-k, 3m, 3n, and 3p show different shapes and features of a volume filling device comprised in an apparatus according to the invention.

FIGS. 9 and 10 show embodiments wherein the volume filling device is adapted to be invaginated in the fundus region of the patient's stomach.

FIG. 12 show an embodiment wherein the volume filling device adapted also for treating reflux is combined with stretching devices for stretching part of the stomach fundus wall.

FIGS. 13-16 show alternative embodiments wherein a combination of a volume filling device and a stretching device is used.

FIG. 22 is an overall view of a patient with an implanted apparatus for treating obesity.

FIGS. 23-41 show various ways of powering an apparatus for treating obesity implanted in a human patient.

FIGS. 59a-c illustrate a preferred method of invaginating a plurality of volume filling device segments into a stomach wall using an instrument.

FIG. 60 illustrates an alternative instrument for invaginating a plurality of volume filling device segments.

DESCRIPTION OF EMBODIMENTS

Figure 1:
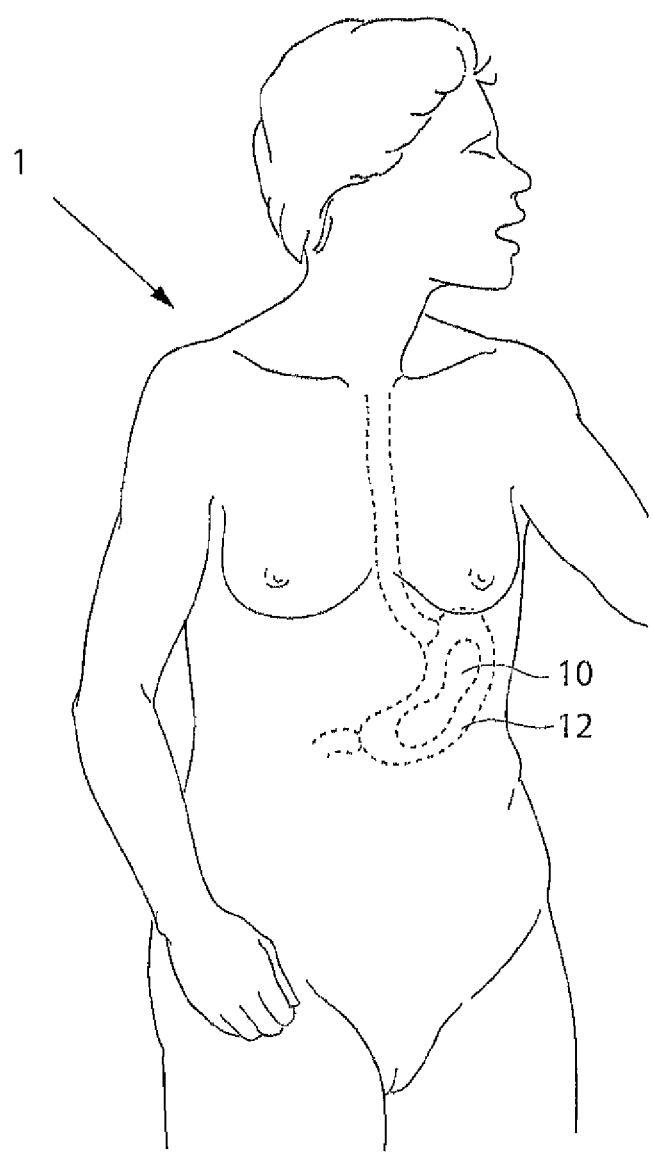
FIG. 1 is an overall view of a patient showing the outlines of the stomach.

Preferred embodiments of the invention will now be described in detail with reference to the drawing figures.

As used herein, the term "segment" should be construed broadly to define any of the parts into which something can be divided.

FIG. 1 shows a human patient 1, who is being treated for obesity. A volume filling device 10 is provided so that it reduces the inner volume of the stomach 12—the food cavity of the stomach, thereby affecting the patient's appetite. The function and the operation of this volume filling device will be described and explained in detail in the following description.

Figure 2A:
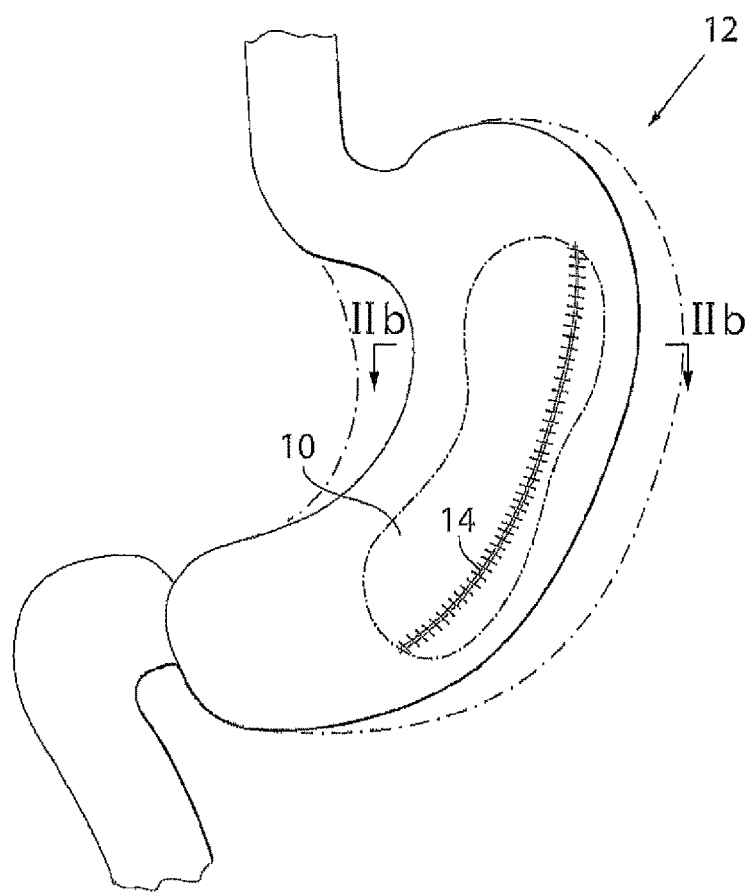
FIG. 2a is a view of a first embodiment of an apparatus for treating obesity implanted in a human patient.
Figure 2B:
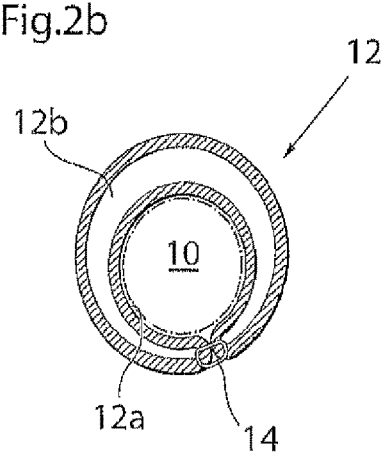

FIGS. 2a and 2b show in detail a first embodiment of an apparatus to treat obesity according to the invention, wherein FIG. 2a show a side view of the stomach while FIG. 2b is a sectional view taken along line IIb-IIb of FIG. 2a. The apparatus comprises a volume filling device 10 implanted in a human patient. More specifically, in the embodiment of FIG. 2a the volume filling device 10 is invaginated in the wall 12a of the patient's stomach 12 on the outside of the stomach wall. The body of the volume filling device 10 is elongated and shaped to rest against the wall 12a of the stomach 12 and further has an outer surface suitable to rest against this wall.

By invaginating the volume filling device 10 in part of the stomach wall, the size of the food cavity, generally designated 12b in FIG. 2b, will be reduced, resulting in a more rapid feeling of satiety after food intake.

The volume filling device 10 preferably comprises an elastic material, such as silicone. In this way, the volume filling device can adapt to the movements of the stomach, the degree of food intake etc.

By providing the volume filling device from a biocompatible material, the risk of the patient's body rejecting the implant is to a very large extent reduced.

The volume filling device 10 can be fixed to the wall 12a of the stomach 12 in a number of different ways. In the embodiment shown in FIG. 2b, the volume filling device 10 is invaginated in the stomach wall 12a. After invagination, a number of stomach-to-stomach sutures or staples 14 are applied to keep the invagination in the short term. This allows growth of human tissue, keeping the invagination in the long term.

The volume filling device 10 preferably has an essentially round shape to not damage the stomach wall. An example thereof is shown in FIG. 3a, wherein the volume filling device is essentially egg-shaped. In another preferred embodiment, the volume filling device is slightly bent, such as the embodiment shown in FIG. 3b. However, since the stomach wall is strong many different shapes, forms, and dimensions may be used. In one embodiment, the volume filling device has a diameter of about 40 millimeters and a length of about 120 millimeters, resulting in a volume that is about half the volume of the patient's stomach. However, it is preferred that the maximum circumference of the volume filling device is at least 30 millimeters, more preferably at least 50 millimeters, and even more preferably at least 80 millimeters.

It is not necessary that the volume filling device is elongated. In the embodiment shown in FIG. 3c, the volume filling device 10 is essentially spherical or ball-shaped. In order to fill out the stomach, two or more such volume filling devices may be combined to achieve the desired decrease of the food cavity of the patient's stomach.

It has been mentioned that the volume filling device is secured by the stomach-to-stomach sutures or staples. In order to further improve the fixation, the volume filling device may be provided with a waist portion having smaller diameter that the maximum diameter of the volume filling device. Such volume filling device having a waist portion 10a is shown in FIG. 3d.

The volume filling device 10 may consist of at least two inter-connectable portions so that each portion is easier to insert into the stomach and further through a hole in the stomach wall. Thus, FIG. 3e shows a volume filling device comprising two more or less spherical sub-parts 10b, 10c interconnected by a portion with which preferably has smaller diameter. The portion with smaller diameter may comprise an interconnection means with a reversible function allowing subsequent disconnection of the two interconnected sub-parts 10b, 10c. Such means may comprise a bayonet socket, a screw connection or the like, designated 10d in the figure. Alternatively, the portion with smaller diameter may comprise a fixed interconnection, such as resilient locking hooks provided on one of the sub-parts 10b, 10c and engaging the rim of a hole provided in the other one of the sub-parts 10b, 10c.

The configuration of the volume filling device 10 is not limited to one waist portion 10a. Thus, in FIG. 3f a volume filling device with two waist portions is shown.

In order to facilitate positioning of the volume filling device, an attachment means in the form of a handle or the like may be provided on the outer surface of the volume filling device. One example thereof is shown in FIG. 3g, wherein also a detail view of a handle 10e is shown. In a preferred embodiment, the attachment means is provide at an end portion of the volume filling device 10. In order to avoid protruding portion on the surface of the volume filling device 10, the handle 10e is provided flush with the outer surface of the volume filling device 10 and a recess 10f is arranged to allow a gripping tool or instrument (not shown in FIG. 3g) to achieve firm gripping around the handle 10e.

The volume filling device may comprise a tube for filling or emptying the volume filling device of a fluid or gel. By injecting fluid or gel into the volume filling device 10, the volume filling device is inflated to an inflated state, as will be described below. The size of the volume filling device can also be adjusted by moving fluid or gel therefrom to a different reservoir.

A volume filling device 10 adapted for this is shown in FIG. 3h. A tube 10g is fixedly attached to the volume filling device. This tube can be attached to a suitable instrument (not shown) or an injection port, which will be explained in detail below.

Instead of having a fixedly attached tube, the volume filling device 10 may comprise an inlet port 10h adapted for connection of a separate tube (not shown in this figure).

Figure 3J:
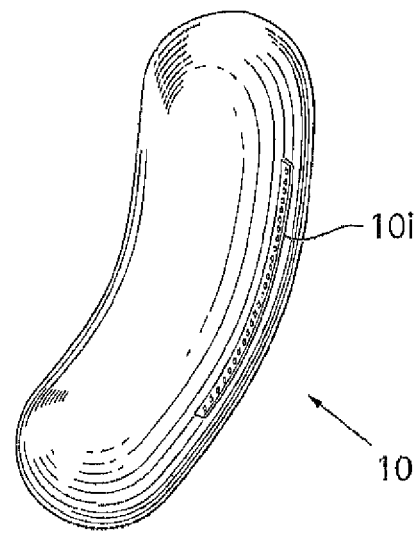

It is important that the implanted volume filling device is firmly kept in place in the stomach wall in which it is invaginated. To this end, the volume filling device can be provided with one or more through holes adapted for receiving sutures or staples used for fixation of the invagination. Such an embodiment is shown in FIG. 3j, where the volume filling device 10 is provided with a row of holes 10i provided on a protruding flange-like protrusion on the volume filling device. In this embodiment, the row of holes extends along the longitudinal axis of the volume filling device.

Figure 3K:
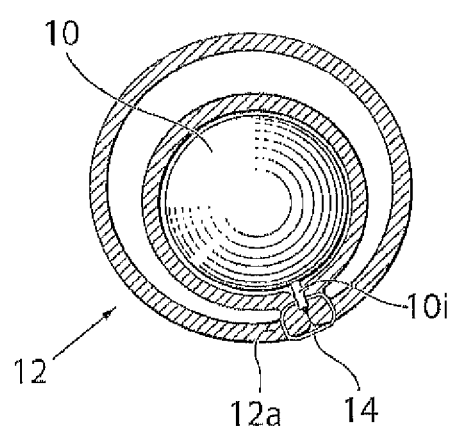

FIG. 3k illustrates how sutures 14 are provided so that they run through the stomach wall 12a and through the holes 10i. In this way, the volume filling device is fixed in place in the pouch created from the stomach wall and will thus be prevented from sliding.

Although a plurality of holes is illustrated in the FIG. 3j, it will be appreciated that one single hole is sufficient to obtain improved fixation of the volume filling device 10.

Figure 3M:
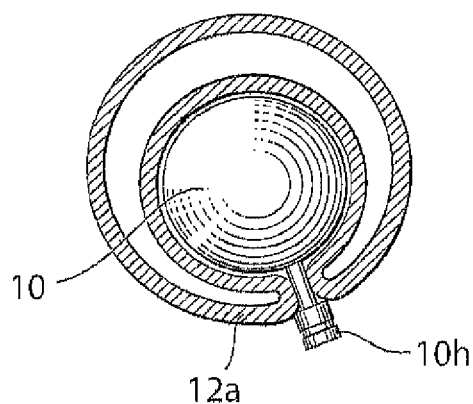

FIG. 3m illustrates a volume filling device provided with an inlet port 10h. The volume filling device is invaginated in the stomach wall and the inlet port 10h is available for connection to a tube or the like from the abdominal area of the patient.

Figure 3N:
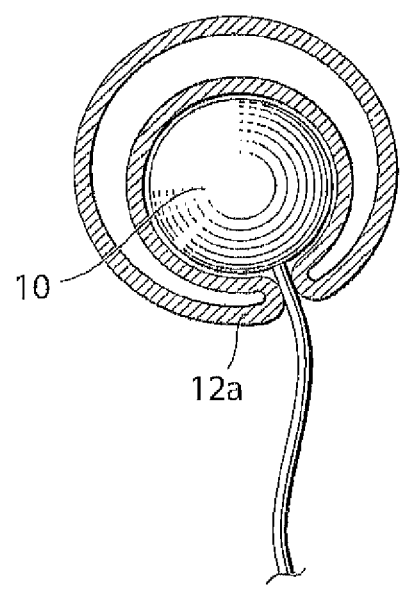

FIG. 3n illustrates an invaginated volume filling device wherein, instead of an inlet port, a fixed tube 100g extends into the abdominal area of the patient.

Figure 3P:
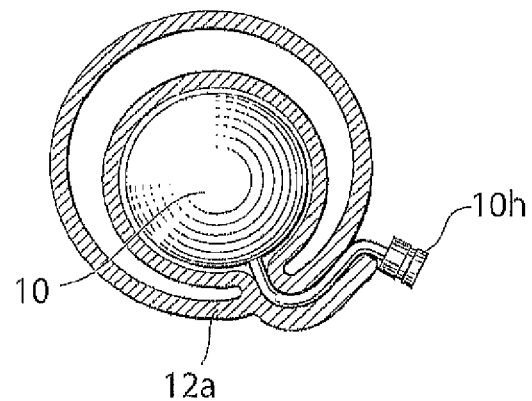

FIG. 3p is a figure similar to FIG. 3m but also illustrating tunneling of a connection tube 10g in the stomach wall between the inlet port 10h and the volume filling device 10.

It has been shown that the shape of the volume filling device can take many different forms. It will be appreciated that also the material of the volume filling device can vary. It is preferred that the volume filling device is provided with a coating, such as a Parylene, polytetrafluoroethylene (PTFE), or polyurethane coating, or a combination of such coatings, i.e., a multi-layer coating. This coating or multi-layer coating improves the properties of the volume filling device, such as its resistance to wear.

In one embodiment, the volume filling device comprises an inflatable device expandable to an expanded state. In this case, the inflatable device is provided with an inlet port for a fluid and is adapted to be connected to a gastroscopic instrument. This embodiment will now be described in detail with reference to FIGS. 4a-4d.

Figure 4A:
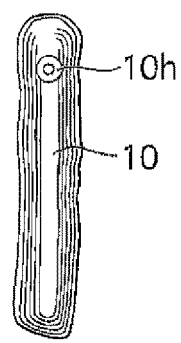
FIGS. 4a-d show a deflated inflatable volume filling device comprised in an apparatus according to the invention and an instrument for placing the volume filling device.

An inflatable volume filling device in its non-expanded state is shown in FIG. 4a. It is essentially a balloon-like, deflated device 10 having an inlet port 10h. In this state, the inflatable device has a diameter of a few millimeters at the most, allowing it to be inserted into the stomach through the esophagus of the patient by means of a gastroscopic, tube-like instrument 600, depicted in FIG. 4b. The instrument comprises an outer sleeve 600a and an inner sleeve 600b which can be displaced longitudinally relatively to the outer sleeve. The inner sleeve is provided with a cutter in the form of a cutting edge 615 at the distal end thereof. This cutting edge can be used for cutting a hole in the stomach wall, as will be explained in detail in the following.

Figure 4B:
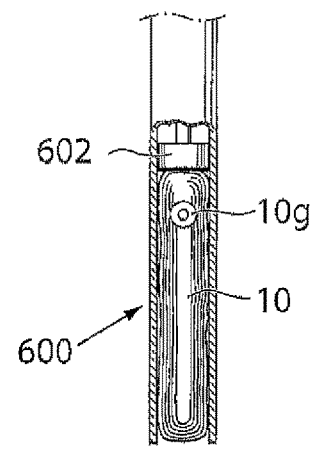
Figure 4C:
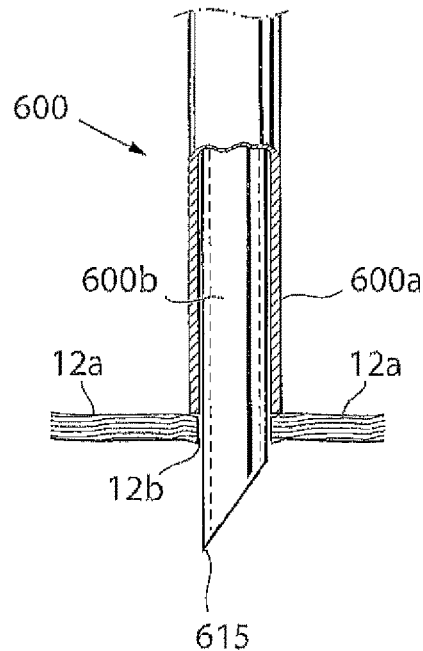
Figure 4D:
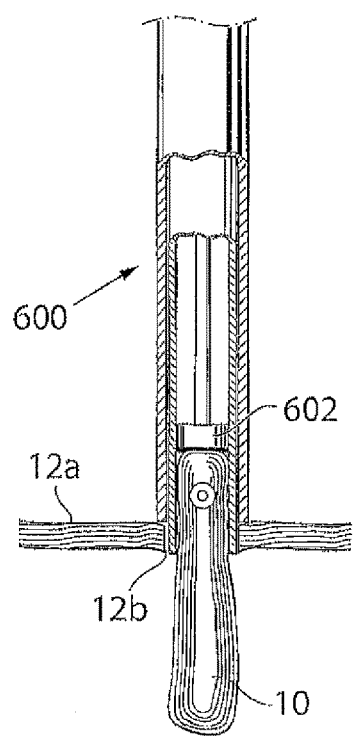

When the instrument reaches a stomach wall, see FIG. 4c, the inner sleeve is brought forward from its position in the outer sleeve and into contact with the stomach wall 12a. The cutting edge 615 of the inner sleeve then cuts a hole in the stomach wall so as to allow subsequent insertion of the volume filling device 10 into and through this hole, see FIG. 4d. In order to push the volume filling device through the hole, a piston 602 may be provided in the instrument. Thus, the instrument further comprises a piston 602 adapted for pushing a deflated volume filling device 10 out from a position in the inner sleeve, this position being shown in FIG. 4b, to a position outside of the inner sleeve, this being shown in FIG. 4d.

In order to protect the deflated volume filling device 10 from the cutting edge 615 of the inner sleeve, a further protective sleeve (not shown) can be provided around the volume filling device.

An intraluminar method of invaginating a volume filling device 10 on the outside of the stomach wall 12a will now be described with reference to FIGS. 5a-i. Initially, an instrument 600, preferably a gastroscopic instrument is inserted into the mouth of the patient, see FIG. 5a. The instrument comprises an injection device 601, 602 for injecting either fluid or a device into the stomach of the patient. The instrument 600 further comprises a control unit 606 adapted for controlling the operation of the instrument. To this end, the control unit 606 comprises one or more steering devices, in the embodiment shown in the figure in the form of two joysticks 603 and two control buttons 604. A display 605 is provided for displaying the image provided by an optical device for viewing inside the stomach, such as a camera (not shown) arranged at the outer end of the elongated member 607, see FIGS. 5e-i. The camera, which may comprise connecting electrical wires extending along the elongated member, may be assisted by a light source (not shown) placed distally on the elongated member for illuminating the inside of the stomach. The optical device may also comprise optical fibers placed along the elongated member and leading out from the patient's body for external viewing of the inside of the stomach.

Figure 5A:
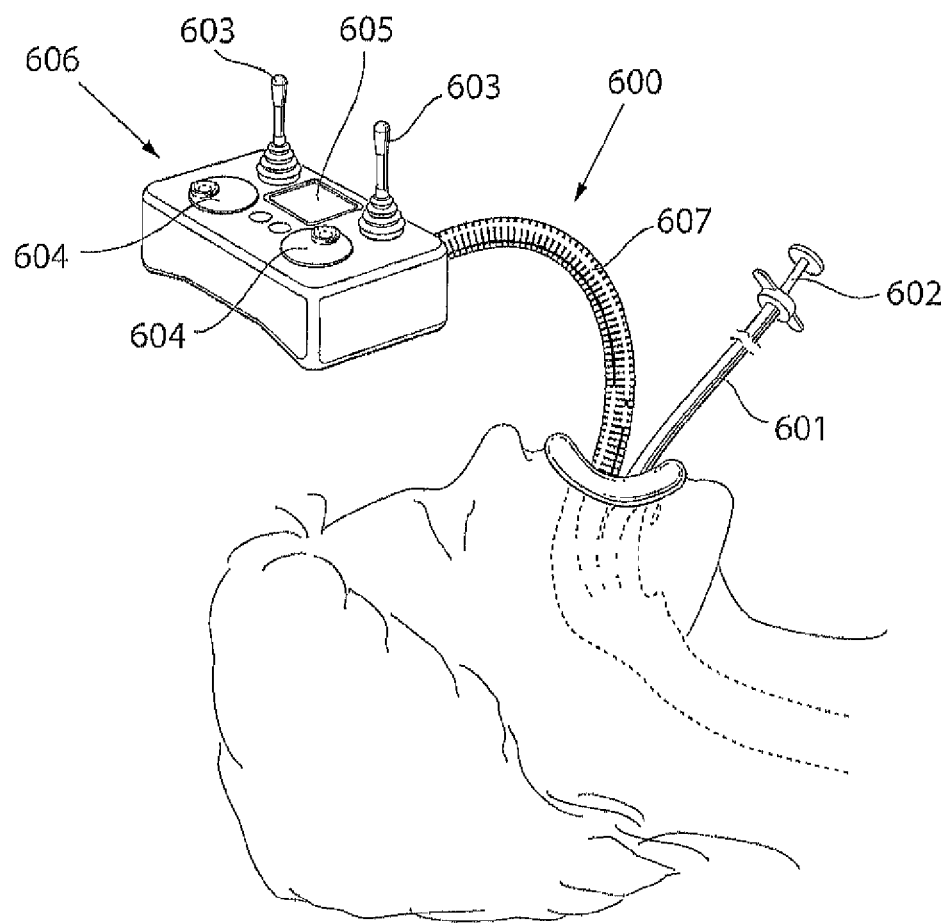
FIGS. 5a-i illustrate different steps of invaginating the inflatable device of FIG. 4a on the outside of a stomach wall of a patient.
Figure 5B:
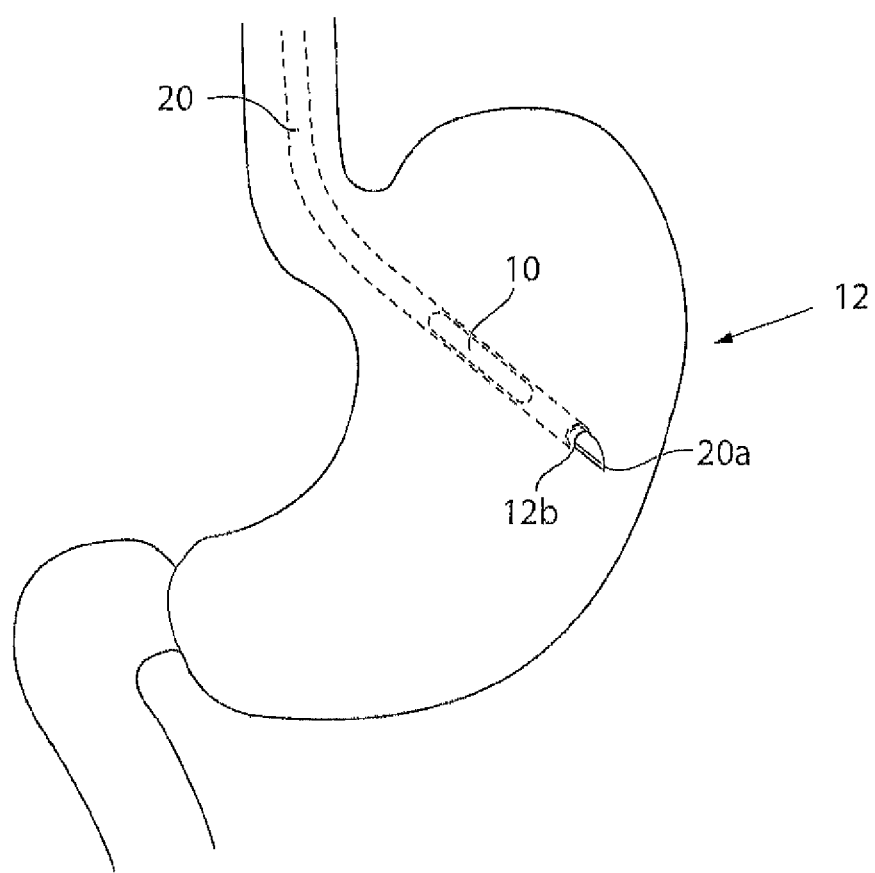

The instrument is further inserted into the esophagus and into the stomach of the patient, see FIG. 5b. By means of the instrument 600, a hole 12b is created in the wall of the stomach 12. To this end, the instrument is provided with one or more cutters 615 at the distal end thereof, for example in the way described above with reference to FIGS. 4a-d. These cutters can of course be designed in different ways, such as a toothed drum cutter rotating about the center axis of the tube-like instrument.

Figure 5C:
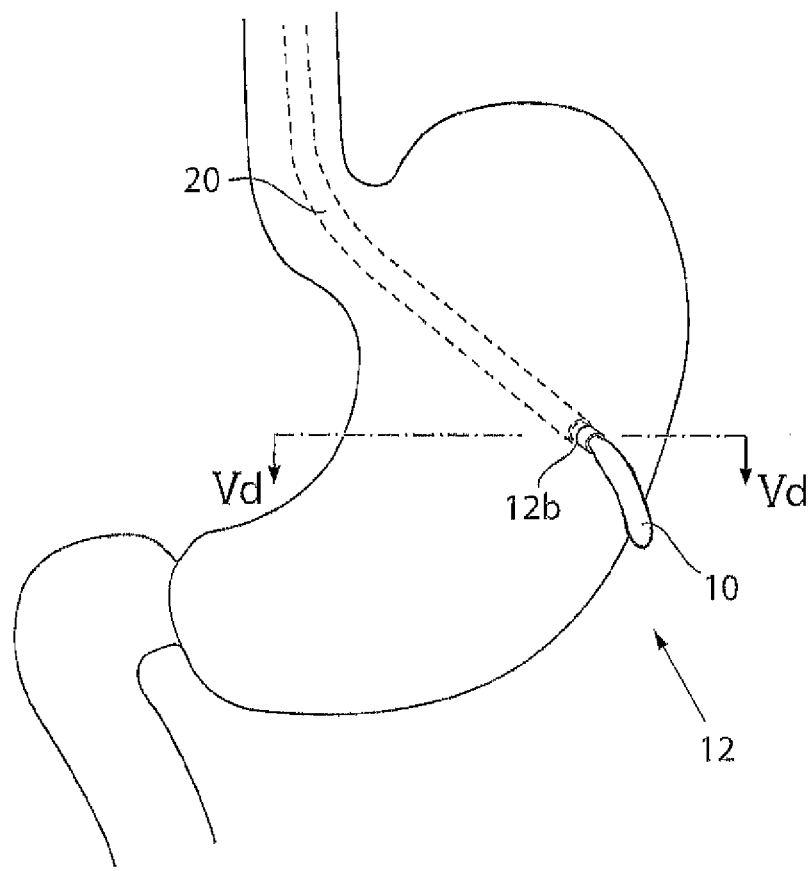
Figure 5D:
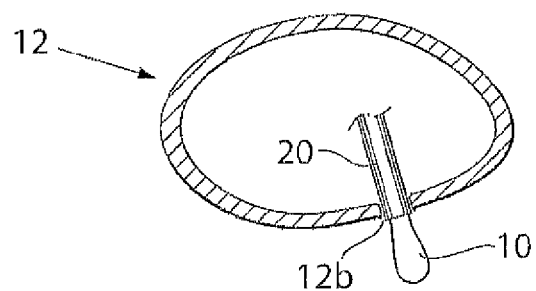
Figure 5E:
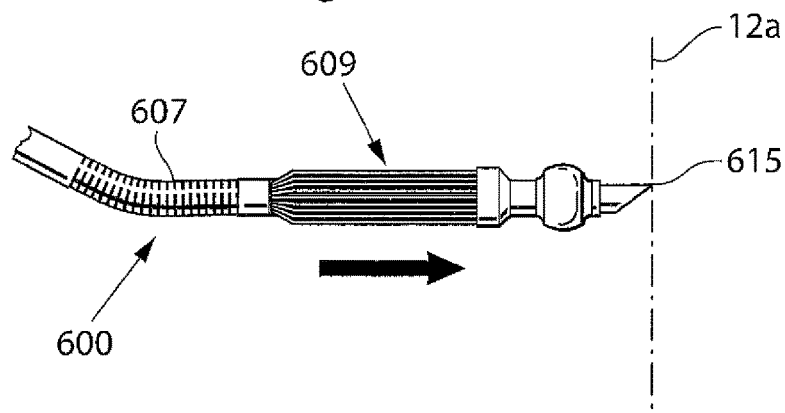
Figure 5F:
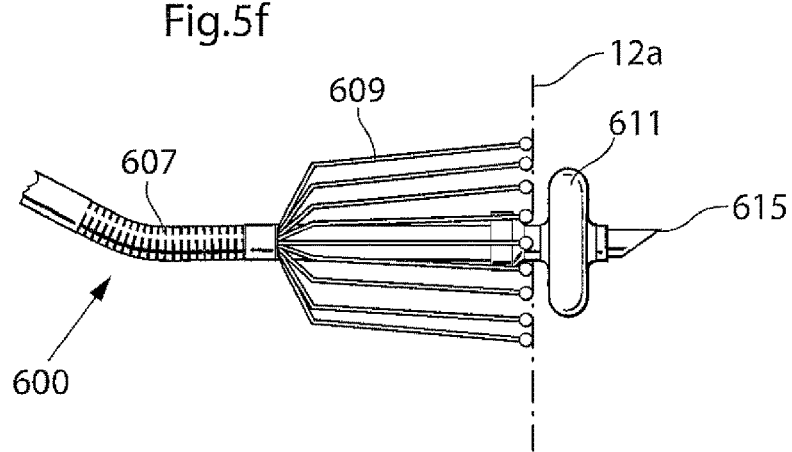

After cutting a hole in the stomach wall, the distal end of the instrument 600 is inserted into and through the hole 12b so that it ends up outside the stomach wall 12a. This is shown in FIG. 5c, showing a side view of the stomach 12, and FIG. 5d, which is a sectional view through the stomach of FIG. 5c taken along the lines Vd-Vd.

The instrument 600 is adapted to create a "pocket" or "pouch" on the outside of the stomach 12 around the hole 12b in the stomach wall. Such an instrument and the method of providing the pouch will now be described.

FIGS. 5e-i show a gastroscopic or laparoscopic instrument for invaginating a volume filling device 10 in the stomach wall 12a of the patient by creating a pouch of stomach wall 12a material in which the volume filling device is placed. The instrument, generally designated 600, and which may comprise the features described above with reference to FIGS. 4a-d, comprises an elongated member 607 having a proximal end and a distal end, the elongated member 607 having a diameter less than that of the patient's esophagus and being flexible such as to allow introduction of the flexible elongated member 607 with its distal end first through the patients throat, esophagus and into the stomach 12 to the stomach wall 12a.

The stomach penetration device or cutter 615 is provided on the elongated member 607 at the distal en thereof for penetrating the stomach wall 12a so as to create a hole in the stomach wall 12a, to allow introduction of the elongated member 607 through the hole. The stomach penetration device 615 could be adapted to be operable for retracting said stomach penetration device 615 after the stomach fundus wall 12a has been penetrated, for not further damaging tissue within the body. The instrument further comprises a special holding device 609 provided on the elongated member 607 on the proximal side to the penetration device 615.

The elongated member further comprises an expandable member 611 which is adapted to be expanded after the elongated member has penetrated the stomach wall 12a and thereby assist in the creation of a cavity or pouch adapted to hold the volume filling device 610. The expandable member 611 may comprise an inflatable circular balloon provided circumferentially around the distal end portion of the flexible elongated member 607.

The method steps when invaginating the volume filling device will now be described in detail. After the instrument 600 has been inserted into the stomach 12, the stomach penetration device 615 is placed into contact with the stomach wall 12a, see FIG. 5e. The stomach penetration device or cutter 615 is then brought to create the hole 12b in the stomach wall, whereafter at least the expandable member 611 is brought through the hole 12b in the stomach wall. The special holding device 609 is in this step brought to a holding state wherein it expands radially so as to form an essentially circular abutment surface to the stomach wall 12a, see FIG. 5f. In this way, the insertion of the stomach penetration device 615 and the expandable member 611 through the hole 12b in the stomach wall is limited to the position shown in FIG. 5f.

The expandable member 611 is then expanded. In the case the expandable member comprises a balloon or the like, air or other fluid is injected into it.

Figure 5G:
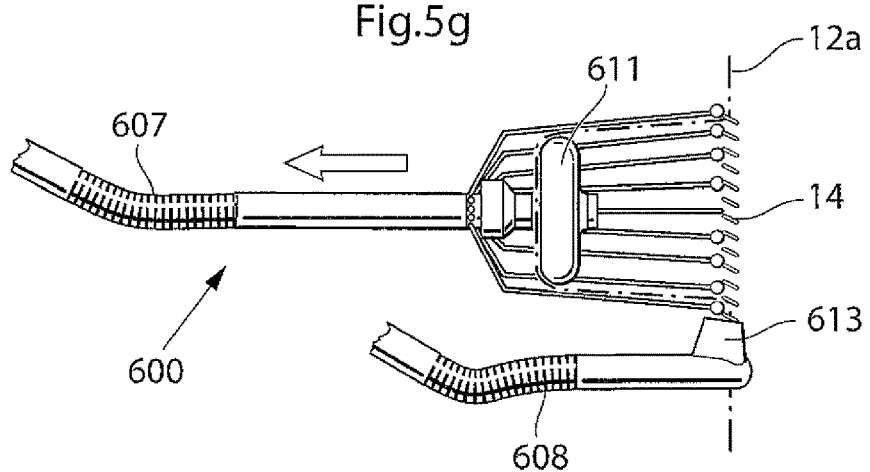

The part of the elongated member 607 comprising the expandable member 611 is then retracted in the proximal direction, as indicated by the arrow in FIG. 5g, thereby pulling the stomach wall 612 into a basket or cup like structure created by the special holding device 609.

A suturing or stapling device 608 is further provided, either as a device connected to the elongated member 607 or as a separate instrument. The suturing or stapling member comprises a suturing or stapling end 613 which is adapted to close the cavity or pouch by means of stomach to stomach sutures or staples 14.

Figure 5H:
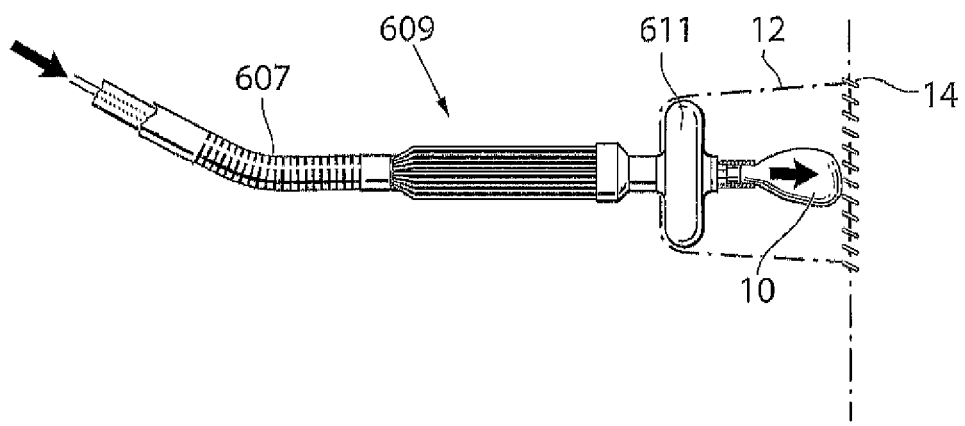
Figure 5I:
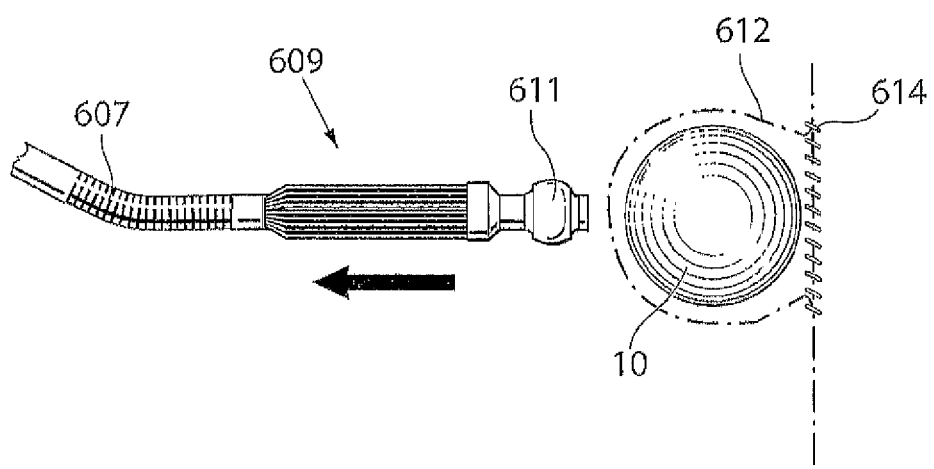

In a further step, illustrated in FIG. 5h, an inflatable volume filling device 10 is placed in its deflated state in the cup like structure. The volume filling device 10 is then inflated to its inflated or expanded state, see FIG. 5i. This inflation of the volume filling device 10 can be accomplished by injecting a fluid or a gel into the deflated volume filling device. It can also be accomplished by injecting a material which is allowed to cure, thereby forming a solid device 10. Thus, the volume filling device 10 shown in FIGS. 5h and 5i can illustrate either a balloon-like device which is subsequently filled with fluid or gel or alternatively a material which is simply injected into the cup like structure formed by the stomach wall 12a.

The fluid which is used to fill the volume filling device 10 could be any suitable fluid suitable to fill the inflatable device 10, such as a salt solution. In another embodiment, when this fluid is a fluid which is adapted to be transformed into solid state, the fluid could be liquid polyurethane.

In order to minimize or entirely eliminate leakage, the fluid is iso-tonic, i.e., it has the same osmolarity as human body fluids. Another way of preventing diffusion is to provide a fluid which comprises large molecules, such as iodine molecules.

The stomach-to-stomach sutures or staples are preferably provided with fixation portions exhibiting a structure, such as a netlike structure, adapted to be in contact with the stomach wall to promote growth in of human tissue to secure the long term placement of the volume filling device attached to the stomach wall.

After the inflatable device 10 has been inflated, partly or fully, the inlet port 10h (not shown in FIGS. 5h and 5i) of the volume filling device 10, is sealed and the instrument 600 is retracted from the hole 12b, which is subsequently closed in some suitable way, such as by means of the instrument 600. The instrument is then removed from the stomach 600 and the inflatable device 10 in its inflated or expanded state is invaginated by a stomach wall portion of the patient on the outside of the stomach wall. This reduces the inner volume of the stomach, thereby affecting the patient's appetite.

During one or more of the above described steps, the stomach may be inflated with gas, preferably by means of the gastroscopic instrument.

The volume filling device 10 described above with reference to FIGS. 5a-i has been described as an inflatable volume filling device. It will be appreciated that is also can be an elastic volume filling device with an elasticity allowing compression so as to be inserted into a gastroscopic instrument and which expands to an expanded state after leaving the instrument.

Figure 6A:
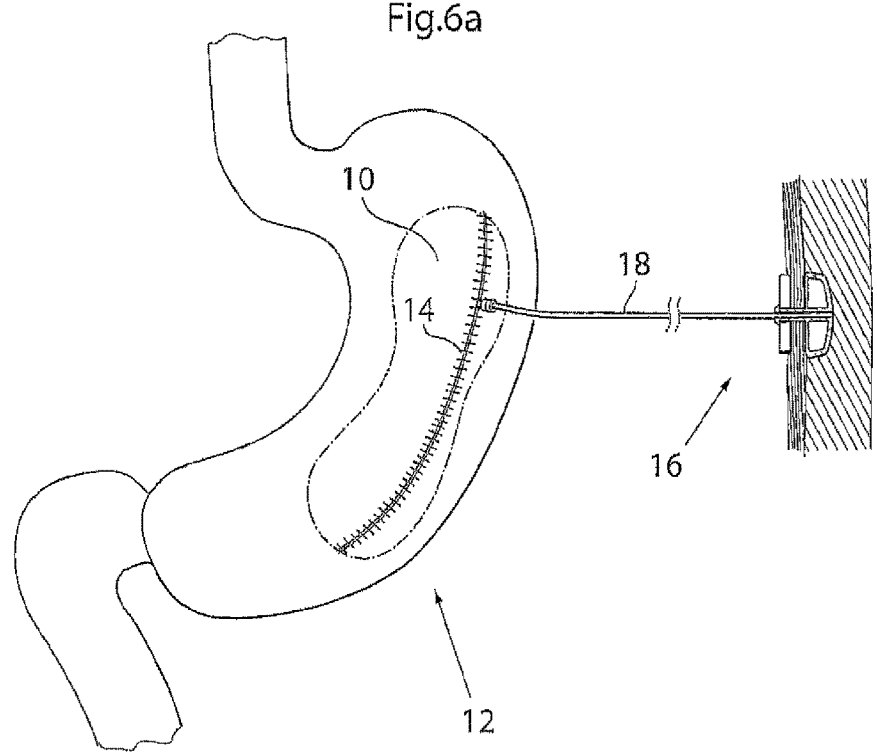
FIGS. 6a, 6b, 7, and 8 show alternative embodiments wherein the volume filling device is adapted to be non-invasively adjustable postoperatively.
Figure 6B:
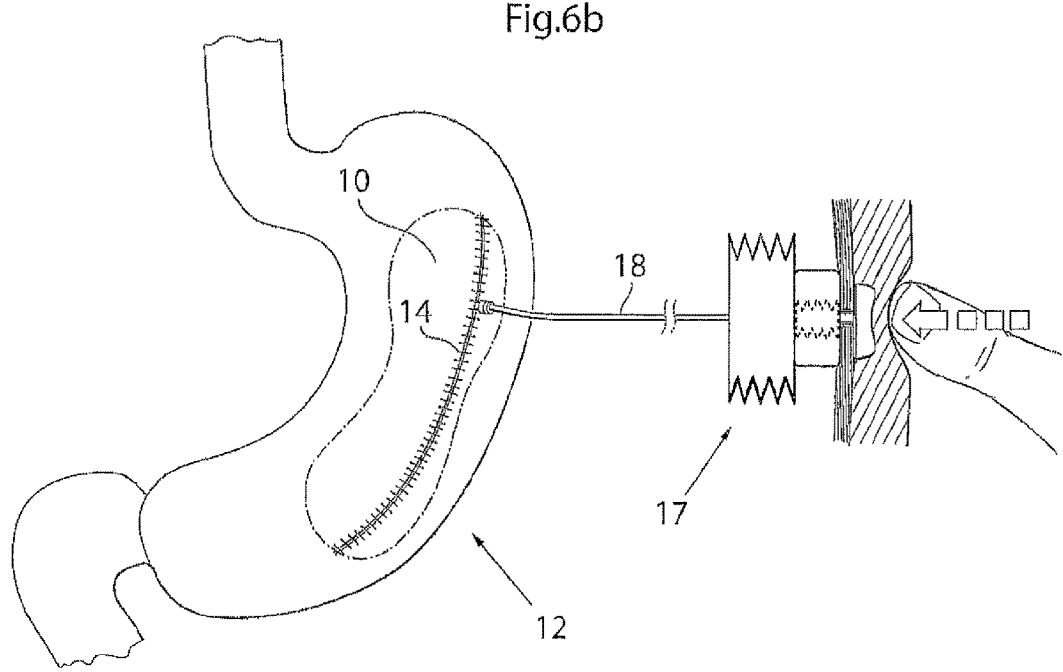

An alternative embodiment of an apparatus for treating obesity will now be described with reference to FIGS. 6a and 6b, showing a sectional view of a stomach in which a volume filling device is invaginated in the stomach wall on the outside thereof together with a system for regulating the size of the volume filling device. The volume filling device is an inflatable device as described above with reference to FIGS. 5a-h and thus comprises a fluid. The inflatable device 10 thus forms a fluid chamber, in which fluid is allowed to flow. The inflatable device thereby forms an expandable chamber that can change the volume it occupies in the stomach wall, thereby forming a hydraulically or pneumatically regulated inflatable device.

In FIG. 6a, an injection port 16 for fluids is connected to the inflatable volume filling device 10 by means of a conduit 18 in the form of a tube. The inflatable device 10 is thereby adapted to be regulated, preferably non-invasively, by moving liquid or air from the injection port 16 to the chamber formed by the inflatable device. By using a hypodermic needle or the like, the amount of fluid in the inflatable device 10 can thus be adjusted, thereby adjusting the size of the adjustable device. The injection port 16 can also be used simply for refilling the volume filling device 10.

The regulation reservoir 17 can be regulated in several ways. In an alternative embodiment, the regulation reservoir 17 is regulated by manually pressing a regulation reservoir. In other words, the regulation reservoir is regulated by moving a wall of the reservoir. It is then preferred that the regulation reservoir is placed subcutaneously and non-invasive regulation is thereby achieved.

A similar embodiment is shown in FIG. 6b. However, in this embodiment the injection port 16 has been replaced by an adjustable regulation reservoir 17 in fluid connecting with the volume filling device 10 via a tube 18. When the regulation reservoir 17 is pressed, the volume thereof decreases and hydraulic fluid is moved from the reservoir to the chamber formed by the inflatable device 10 via the conduit or tube 18, enlarging or expanding the inflatable device 10. In this way, the volume filling device is non-invasively adjustable postoperatively.

It will be appreciated that instead of hydraulic operation, pneumatic operation can be used, wherein air instead of hydraulic fluid is moved between the regulation reservoir and the chamber formed by the inflatable device 10. Preferable the regulation reservoir has a locking position to keep it in the desired position. If the patient compresses the reservoir it preferably stays compressed and releases after pressing again.

Any kind of hydraulic solution may be used for the inflatable device. The hydraulic solution may be driven by both mechanically and be powered with any motor or pump as well as manually.

Figure 7:
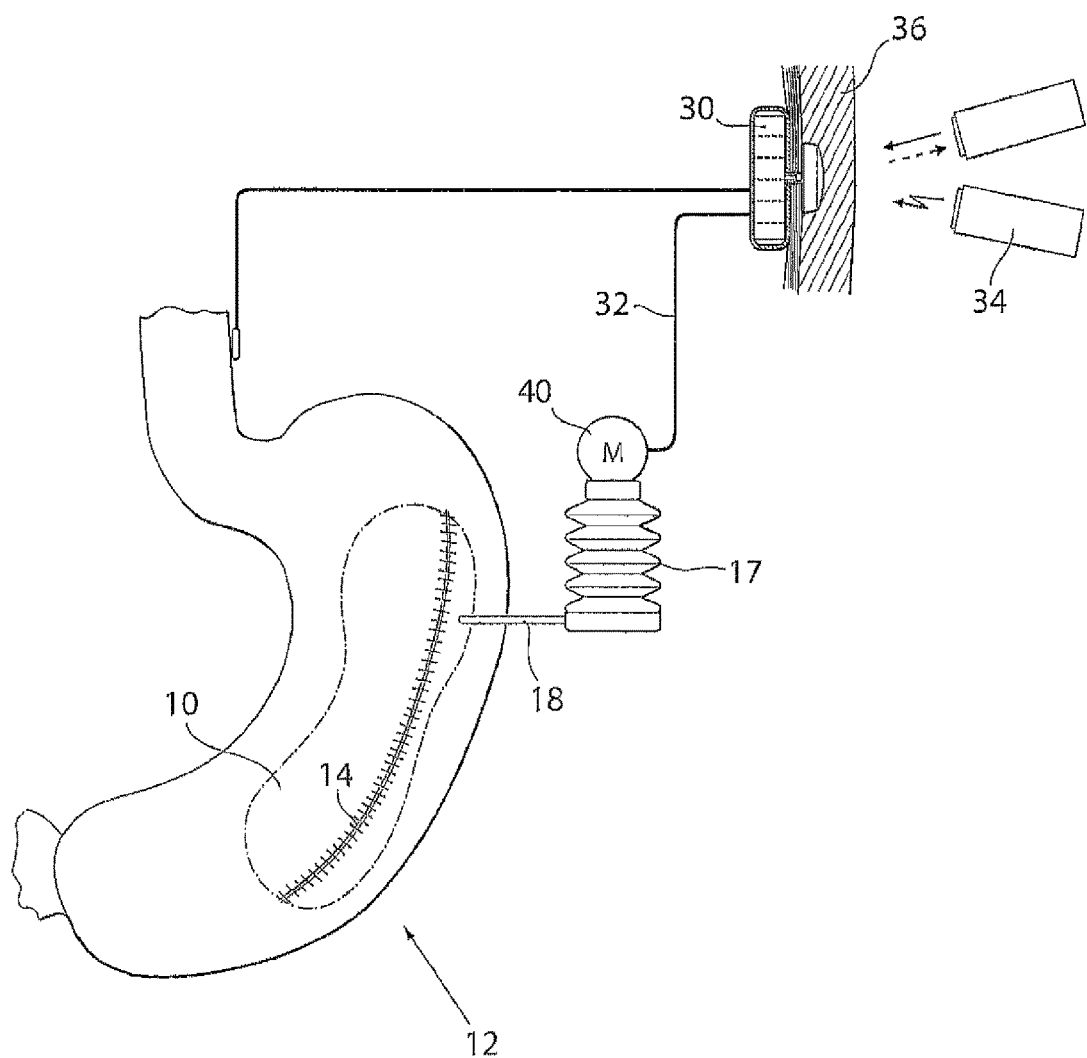

In another embodiment, shown in FIG. 7, a motor 40 is adapted to move a wall of the regulation reservoir 17. The powered regulation reservoir 17 is then preferably placed in the abdomen of the patient. In this embodiment, a wireless external remote control unit forming part of the external energy transmission device 34 can be provided to perform non-invasive regulation of the motor via an energy transforming device 30, which is adapted to supply an energy consuming operation device, in the present example the motor 40, with energy via a power supply line 32.

The remote control may comprise a wireless energy transmitter, whereby the non-invasive regulation is performed by the energy transmitter. When the regulation is performed by means of a remote control an internal power source for powering the regulating device is provided. The internal energy source can for example be a chargeable implanted battery or a capacitor or a device for receiving wireless energy transmitted from outside the body of the patient. Different ways of regulating the inflatable device 10 will be described below with reference to FIGS. 22-41.

Figure 8:
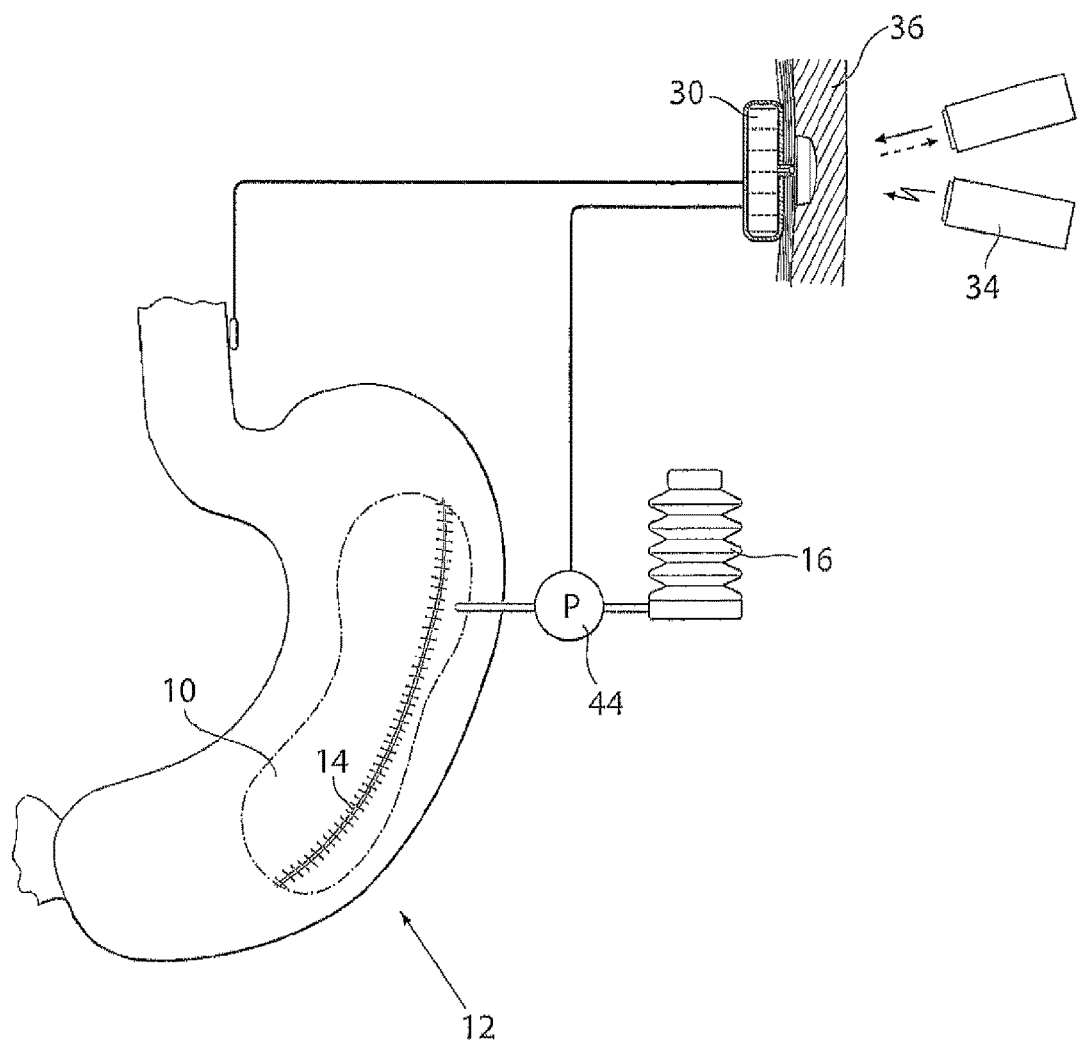

In yet an alternative embodiment, shown in FIG. 8, the apparatus for treating obesity comprises a pump 44, wherein the reservoir is regulated by the pump 44 pumping fluid or air from the reservoir to the chamber formed by the inflatable device. Different configurations of this pump will be described below with reference to FIGS. 22-41.

Yet an alternative embodiment of an apparatus for treating obesity will now be described with reference to FIG. 9, which shows a stomach 12 of a patient who is treated for obesity. This embodiment is similar to the one described above with reference to FIG. 7 and the apparatus comprises a volume filling device in the form of an inflatable device 10 which is invaginated in the wall 12a of the patient's stomach 12. However, in this case the invagination has been performed in the fundus, i.e., the upper portion of the stomach, where the number of receptors in the stomach wall is large, and the inflatable device functions as a stretching device for part of the stomach fundus wall.

A regulation reservoir 17 for fluids is connected to the inflatable device by means of a conduit 18 in the form of a tube. The inflatable device 10 is thereby adapted to be regulated, preferably non-invasively, by moving liquid or air from the regulation reservoir 17 to the chamber formed by the inflatable device 10. The regulation of the inflatable device 10 preferably comprises a reversed servo, i.e., a small volume is actuated for example by the patient's finger and this small volume is in connection with a larger volume, i.e., the regulation reservoir 17.

Thus, the inflatable device 10 is placed outside the stomach wall and is adapted to stretch a part of the stomach fundus wall, thereby affecting the patient's appetite. By enlarging the size of the stretching device, the stomach fundus wall 12a surrounding the inflatable stretching device 10 is stretched since the circumference of the inflatable stretching device 10 is increased. By this stretching, the receptors in the stomach wall indicate that the stomach is full, thereby creating a feeling of satiety to the patient. Correspondingly, when the stretching device 10 is contracted, the receptors indicate that the stomach is not full, thereby returning the feeling of hunger. It will be appreciated that this embodiment combines the effects of both reducing the volume of the stomach food cavity and stretching part of the stomach wall, thereby increasing the treatment effect.

The expansion and contraction of the stretching device 10 can be performed under direct control of the patient. Alternatively, the expansion and contraction can be performed according to a pre-programmed schedule.

In a preferred embodiments shown in FIG. 10, a sensor 19 is provided at a suitable position, such as at the esophagus. The volume filling device 10 in the form of the inflatable stretching device is similar to the one shown in FIG. 9. By providing one or more sensors, the apparatus for treating obesity can be automated in that the size of the volume filling device 10 in the form of the inflatable stretching device is adjusted depending on the amount of food entering the food cavity of the stomach. The fluid is thereby moved between the inflatable volume filling device 10 and a fluid reservoir 15.

Figure 11A:
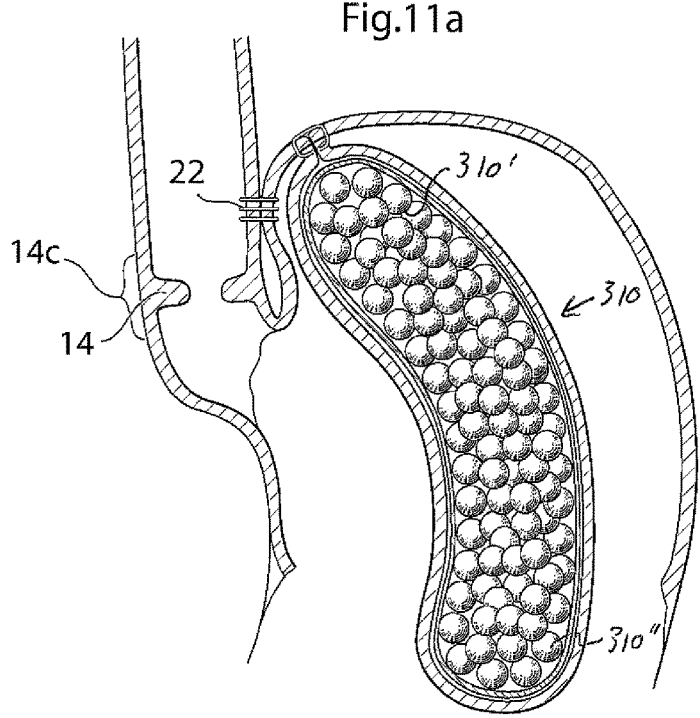
FIG. 11a shows an embodiment wherein the reflux treatment apparatus is also adaptable to treat obesity and comprises a plurality of movement restriction device segments.

The apparatus for treating obesity can have the additional functionality of treating reflux. An embodiment having this function is shown in FIG. 11a, wherein the volume filling device 10 is invaginated in the stomach wall close to and at least partially above the patient's cardia 26 when the patient is in a standing position and is fixed to a position above the cardia area 26 by a fixation, such as sutures or staples 14a. For example a direct or indirect fixation to the diaphragm muscle or other muscle tissue may be provided. As an alternative a direct or indirect fixation to the esophagus above and close to the angle of His can be provided. In this alternative embodiment, the volume filling device 10 rests in a position against stomach wall of the fundus when implanted and which also fills a volume above the cardia area 26 between the cardia and the diaphragm muscle so that the cardia is prevented from slipping up into the thorax cavity, whereby reflux disease is prevented.

In this preferred embodiment, the apparatus for treating both reflux disease and obesity comprises two or more movement restriction device segments adapted to form the movement restriction device 310. In this embodiment, there are a plurality of spherical movement restriction device segments in the form of small balls which are contained in a movement restriction device segment in the form of an outer layer or shell, which preferably is elastic or flexible. In this way, the outer layer can be inserted into the stomach as a separate part, which subsequently is filled with a plurality of small, preferably spherical or polyhedral movement restriction device segments. This method will be explained below with reference to FIGS. 59a-c.

By providing a movement restriction device 310 with a plurality of movement restriction device segments, the movement restriction device 310 easily adapts to the movement of the stomach into which it is invaginated.

Figure 11B:
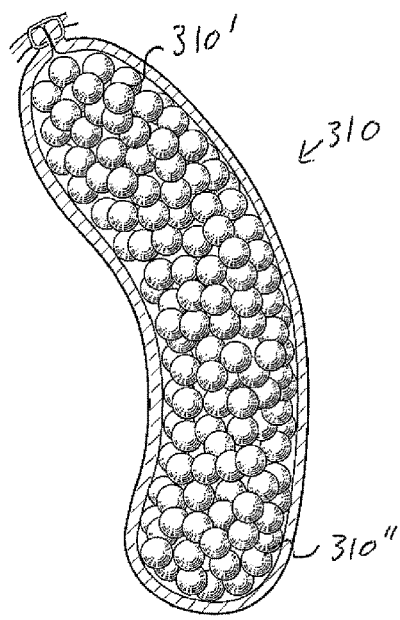
FIG. 11b shows an embodiment wherein the plurality of movement restriction device segments is provided in a pouch created by part of the stomach wall without any containing outer layer.

In an alternative embodiment, the small movement restriction device segments are inserted or injected into a pouch previously created by part of the stomach wall of the patient without any collecting outer layer or shell. This embodiment is illustrated in FIG. 11b and corresponds to the method described below with reference to FIG. 59a-c.

Figure 11C:
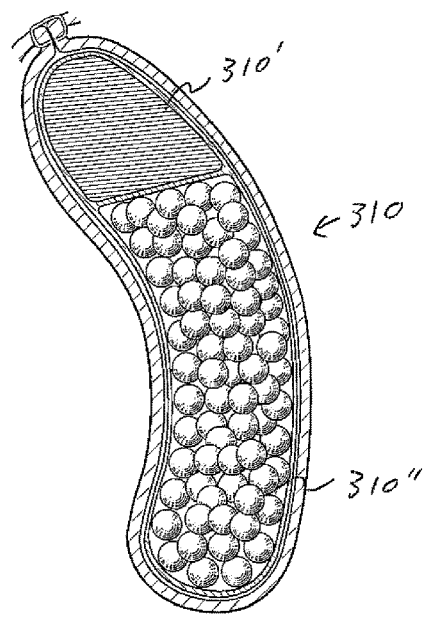
FIG. 11c shows an embodiment similar to the one shown in FIG. 49b but wherein proximal part of the combined reflux and obesity treatment apparatus has a different composition from the distal part the combined reflux and obesity treatment apparatus.

In order to provide a movement restriction device which is more stable in the proximal part 310', this part can be made of a different configuration from the distal part 310". Thus, in an embodiment shown in FIG. 11c, the proximal part 310', which is fixed to a position above the cardia area 14c, comprises a larger ball shaped part or segment, while the distal part 310" comprises a plurality of small movement restriction device segments. This embodiment combines the advantages of a stable proximal part 310' used for preventing reflux with a more adaptable distal part 310" used as a volume filling device for treating obesity. Generally, the proximal and distal parts can have different configurations and contents, independent of each other. This content can be a mixture of solid and fluid content, such as friction enhancing or reducing fluid.

Such a volume filling device 10 may be used for keeping electronics and/or an energy source and/or hydraulic fluid. Hydraulic fluid from that device may be distributed to several smaller inflatable device areas to vary the stretching area from time to time avoiding any possible more permanent stretching effect of the stomach wall. Even mechanically several stretching areas may be used.

In an alternative embodiment, which is shown in FIG. 12, the volume of an inflatable volume filling device 10 may be in fluid connection with one or more preferably smaller inflatable devices or chambers 50. These chambers are adapted to communicate with fluid or air being moved between the chambers.

Thus, the large chamber 10 is adapted to, with its main volume to be a volume filling device for reducing the size of the food cavity and for treating reflux disease and the one or several small chambers are adapted to function as the inflatable devices to treat obesity, wherein the main chamber is adapted to communicate with fluid or air to the small chambers causing a stretching effect in the stomach wall thereby further treating obesity.

In FIGS. 13-16, different embodiments embodying a combination of a volume filling device invaginated in the central or lower portion of the stomach and a stretching device invaginated in the upper portion or fundus of the patient's stomach. Thus, in FIG. 13 there is shown an adjustable volume filling device 10, which is invaginated in the stomach wall of a patient's stomach 12. Additionally, an adjustable stretching device 50 with the previously described function is invaginated in the stomach fundus wall of the patient. It is preferred that the volume filling device 10 is substantially larger than the stretching device 50.

The volume filling device 10 and the stretching device 50 are in fluid communication with each other via a fluid communication device comprising a first fluid tube 52, in which a pump 54 is provided. The pump 54 is under the control from an energy transforming device 30, which is adapted to supply the pump 54 with energy via a power supply line 56. The energy transforming device 30 is also connected to a sensor 19 provided in the esophagus of the patient so that food intake can be detected.

The volume filling device 10 and the stretching device 50 are also in fluid communication with each other via a second fluid tube 58, which preferably has a smaller cross-sectional area than the first fluid tube 52.

The operation of this arrangement is as follows. The volume filling device 10 functions as in the above described embodiments, i.e., it reduces the size of the food cavity of the patient's stomach 12. Additionally, when the stretching device 50 is enlarged by pumping fluid from the volume filling device 10 and to the stretching device 50 by means of the pump 54, the stomach fundus wall is stretched, creating a feeling of satiety for the patient. Thus, for example when food intake is detected by means of the sensor 19, fluid is automatically pumped into the stretching device 50 to increase the feeling of satiety and thereby limit the food intake.

When fluid has been injected into the stretching device 50, the internal pressure therein is higher than the internal pressure in the volume filling device 10. This difference in pressure will create a flow of fluid in the second, preferably narrower tube 58 from the stretching device 50 to the volume filling device 10. The flow rate will be determined by among other things the difference in pressure and the cross-sectional area of the second tube 58. It is preferred that the second tube is so dimensioned, that the pressures in the volume filling device 10 and the stretching device 50 will return to equilibrium after 3 hours after fluid has been injected into the stretching device 50 to create the feeling of satiety.

In this embodiment, the function of the second tube 58 is to allow fluid to return from the stretching device 50 to the volume filling device 10. It will be appreciated that this function also can be performed by the pump 54 in the first tube 52 and that the second tube 58 then can be omitted.

Figure 13:
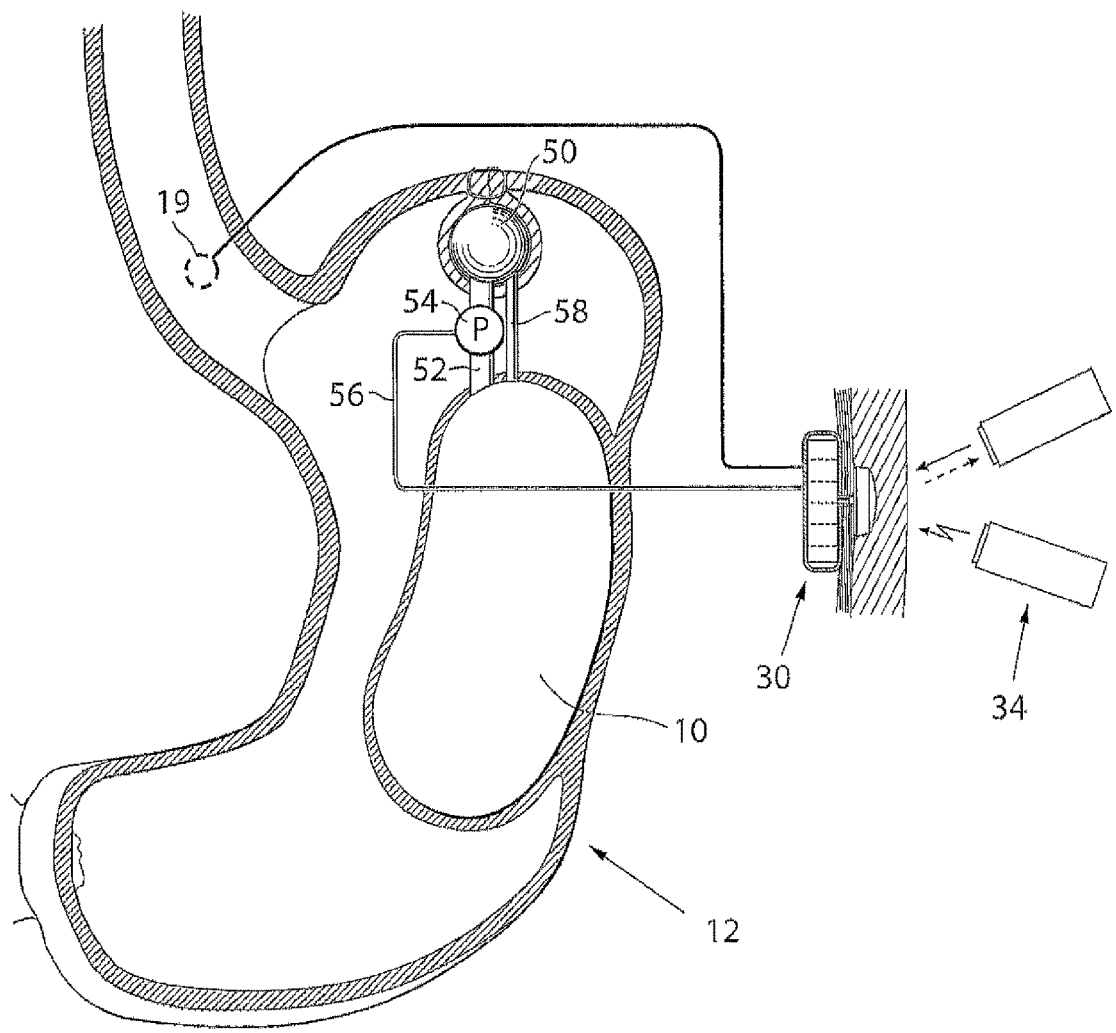

FIG. 14 illustrates an embodiment similar to the one illustrated in FIG. 13. Thus, there is provided an adjustable volume filling device 10, which is invaginated in the stomach wall of a patient's stomach 12. Additionally, an adjustable stretching device 50 with the previously described function is invaginated in the stomach fundus wall of the patient. It is preferred that the volume filling device 10 is substantially larger than the stretching device 50.

The volume filling device 10 and the stretching device 50 are in fluid communication with each other via a first fluid tube 52, and a second fluid tube, which preferably has a smaller cross-sectional area than the first tube. However, instead of a pump, there is provided a non-return valve 60 in the first fluid tube 52 instead of an energized pump. This non-return valve 60 allows fluid to flow in the direction form the volume filling device 10 and to the stretching device 10 but not vice verse. This means that this embodiment may be entirely non-energized. Instead, it operates according to the following principles.

When the food cavity of the stomach 12 is essentially empty, there is a state of equilibrium between the internal pressure of the volume filling device 10 and the stretching device 50. In this state, the stretching device is in a non-stretch state, i.e., it does not stretch a part of the stomach fundus wall and thus does not create a feeling of satiety.

When the patient starts to eat, food will enter the food cavity of the stomach 12. This will create increased pressure on the stomach wall in which the volume filling device 10 is invaginated and the internal pressure therein will increase. Also, the stomach wall muscles will begin to process the food in the food cavity by contraction, which also contributes to an increased internal pressure in the volume filling device 10.

Since the internal pressure in the stretching device 50 will remain essentially unchanged, because it is located in the upper part of the stomach 12 where no food is exerting a pressure on the stomach wall, a fluid flow will be created through the first and second fluid tubes 52, 58 in the direction from the volume filling device 10 and to the stretching device 50. This in turn will increase the volume of the stretching device 50, which, by stretching the stomach fundus wall, will provide a feeling of satiety to the patient.

A fluid flow from the stretching device 50 to the volume filling device 10 through the second tube 58 will return the pressure of these devices to equilibrium as described above with reference to FIG. 13.

FIG. 15 illustrates an embodiment, which is similar to the one shown in FIG. 14 but with the addition of an injection port 16, which is used for refilling the fluid system comprising the volume filling device 10 and the stretching device 50 or alternatively for actively adjusting the size thereof.

Similarly, FIG. 16 illustrates an embodiment wherein the stretching device 50 can be actively regulated by manually pressing an adjustment reservoir which is provided subcutaneously below the patient's skin, similar to the embodiment shown in FIG. 9. Thus, a regulation reservoir 17 for fluids is connected to the inflatable device by means of a conduit 18 in the form of a tube. The stretching device 50 is thereby adapted to be regulated, non-invasively, by moving liquid or air from the regulation reservoir 17 to the chamber formed by the inflatable device. The regulation of the stretching device 50 preferably comprises a reversed servo, i.e., a small volume is actuated for example by the patient's finger and this small volume is in connection with a larger volume.

Figure 17A:
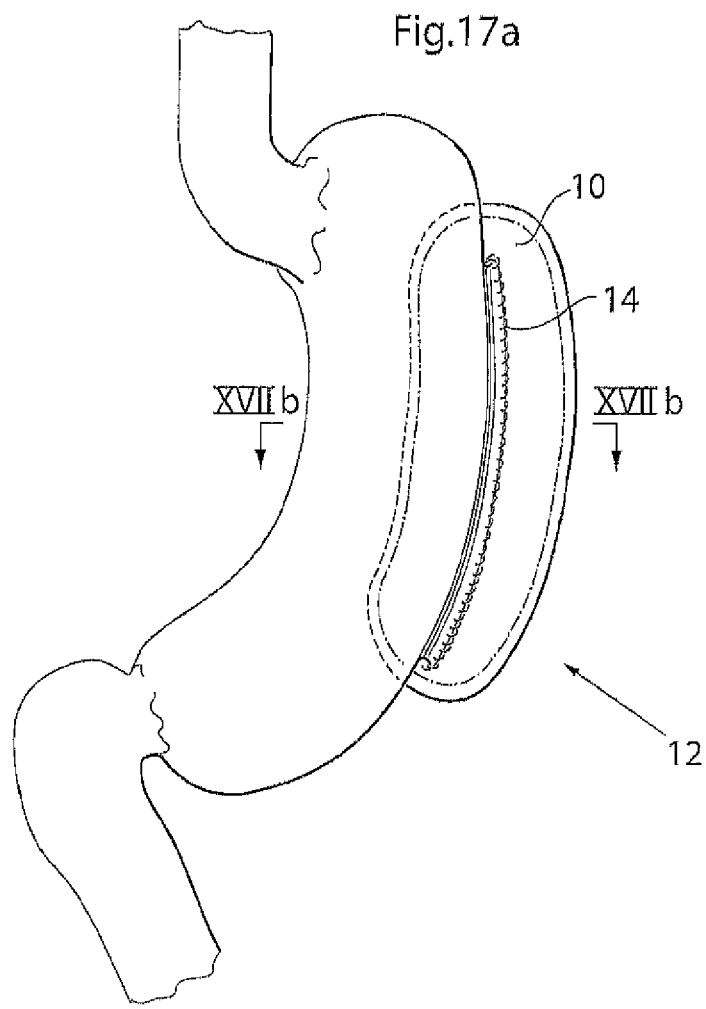
FIGS. 17a and 17b show an embodiment wherein the volume filling device is provided on the inside of the stomach wall.
Figure 17B:
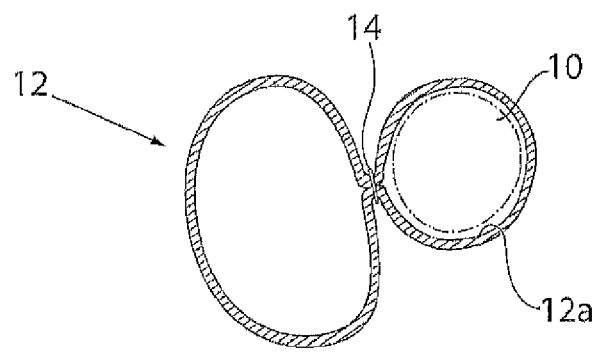

An alternative placement of the volume filling device 10 is shown in FIGS. 17a and 17b, wherein FIG. 17b shows a sectional view through the stomach shown in FIG. 17a along the line XVIIb-XVIIb. There, the volume filling device 10 is adapted to be placed inside the wall of the stomach 12, such as via a gastroscope or similar intraluminar instrument, and resting against the inside of the stomach wall 12a. The inflatable device can be kept invaginated by means of sutures or staples 14, like in the embodiment of FIGS. 2a and 2b. In this embodiment, no hole is required in the stomach wall. Instead, a method of providing the volume filling device 10 can comprise the following steps, which will be explained with reference to FIGS. 18a-i showing an invagination instrument.

The invagination instrument, generally designated 630, comprises an elongated tube member 632 similar to the elongated member 607 described above with reference to FIGS. 5a-i. Thus, it can be connected to a control unit 606, see FIG. 5a. The invagination instrument 630 further comprises a perforated suction portion 634, which preferably is elongated. The suction portion 634 exhibits a plurality of small holes 636, into which air will be sucked by providing suction in the tube member 632. This suction effect will be used to create a "pocket" or "pouch" in a part of a stomach wall, generally designated 12a.

Figure 18A:
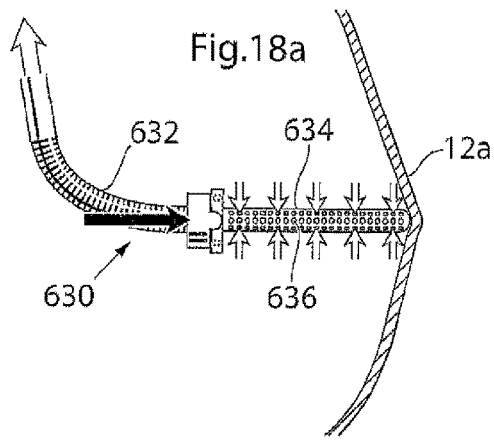
FIGS. 18a-h illustrate different steps of invaginating the inflatable device of FIG. 4a on the inside of a stomach wall of a patient.

In other words, when the tip of the suction portion 634 is pressed against the stomach wall 12a, see FIG. 18a, a small recess will be formed therein. When the suction portion 634 is further pressed against the stomach wall 12a, see FIG. 18b, a larger recess will be formed. The part of the stomach wall 12a that forms the recess will, due to the suction effect, adhere to the suction portion 634 of the invagination instrument 630. As the suction portion 634 is further pressed into the stomach wall 12a, see FIG. 18c, a deeper recess will be formed until the entire suction portion 634 is embedded in the recess, see FIG. 18d.

Figure 18E:
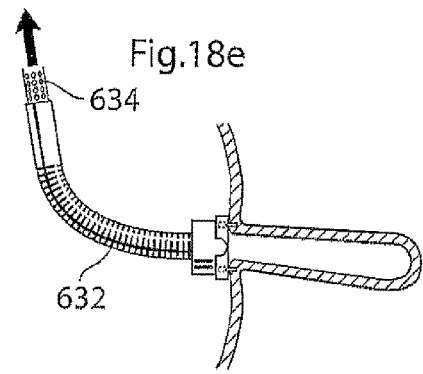
Figure 18B:
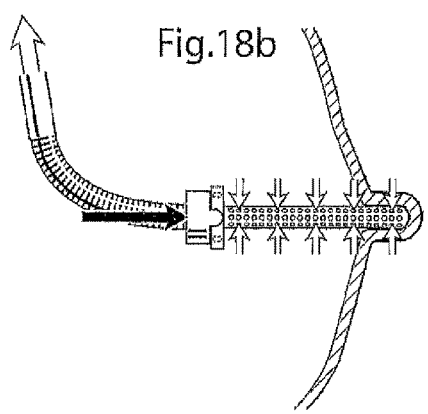
Figure 18F:
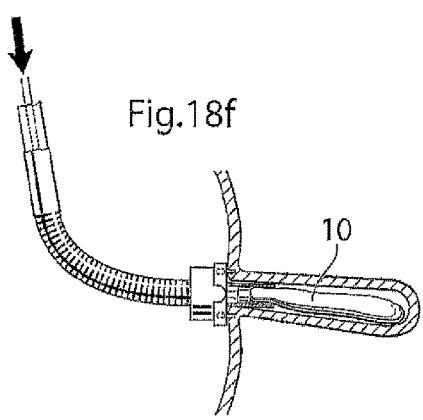
Figure 18C:
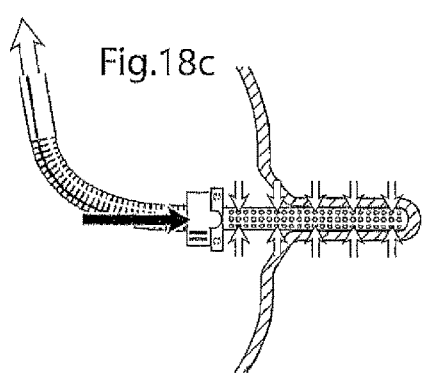
Figure 18G:
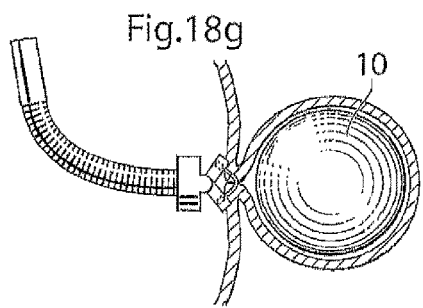
Figure 18D:
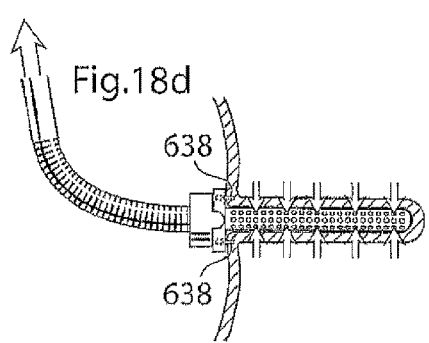
Figure 18H:
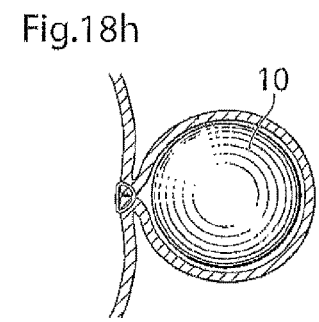

The rim of the recess will at this stage be fixated by means of fixation elements 638 and the suction portion be removed from the instrument, see FIG. 18e. A compressed elastic volume filling device 10 will subsequently be inserted into the recess, see FIG. 18f, for example in the way described above with reference to FIG. 4d. This compressed volume filling device is then expanded to its final shape, see FIG. 18g, where after the pouch is sealed by suturing or stapling by means of the fixations elements, see FIG. 18h.

All the alternatives described above with reference to FIGS. 2-16 are also applicable to the embodiment described with reference to FIGS. 17 and 18, i.e., to the embodiment where the volume filling device is invaginated on the inside of the stomach wall.

Figure 19A:
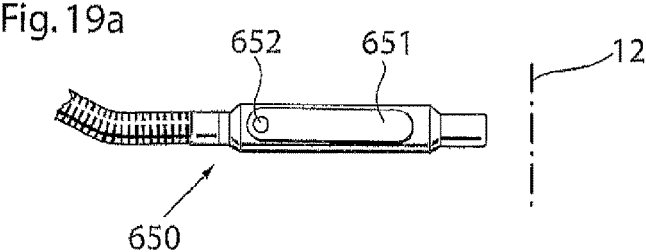
FIGS. 19a-j illustrate different steps of invaginating the inflatable device of FIG. 4a on the inside of a stomach wall of a patient.
Figure 19B:
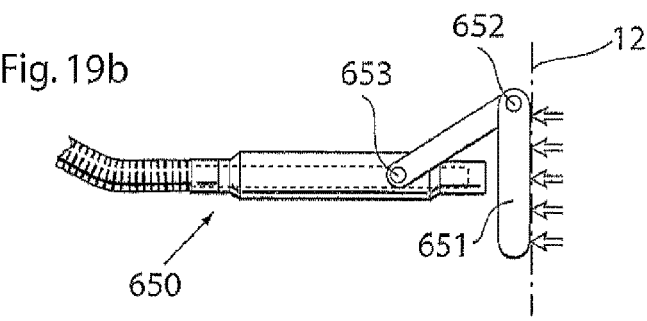
Figure 19C:
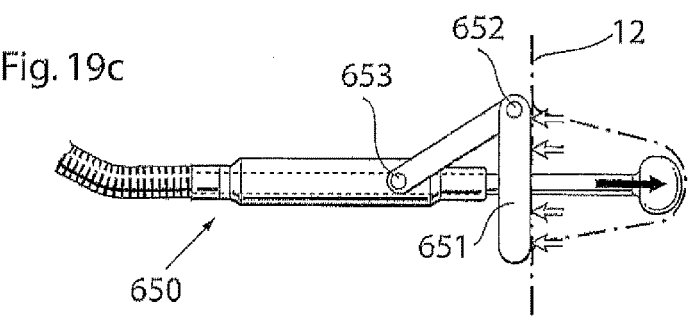
Figure 19D:
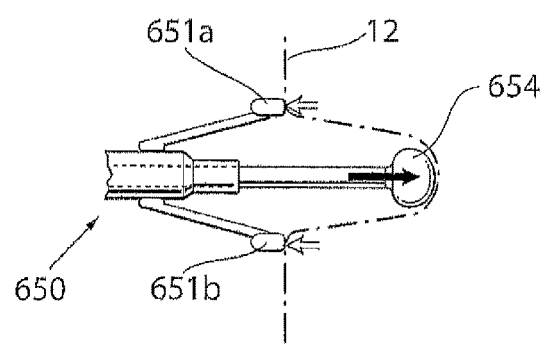
Figure 19E:
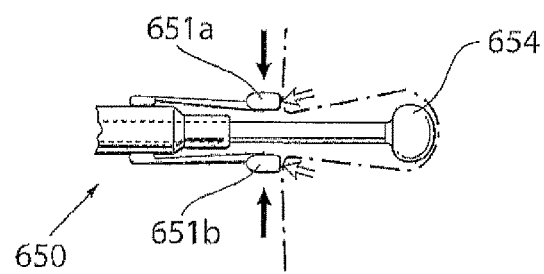

FIGS. 19a-j show an instrument for use in a method of engaging a volume filling device 10 to the stomach wall 12 of a patient. The instrument is adapted to be inserted through a narrow tube shaped object such as a gastro scope, used in an intraluminar procedure, or a laparoscopic trocar used in a laparoscopic procedure. The instrument comprises an elongated member 650 which is adapted to be flexible by means of a construction comprising multiple ring shaped members, however it is equally conceivable that said elongated member 650 is adapted to be flexible by means of said elongated member 650 being made of a flexible or adjustable material. The elongated member 650 is inserted into the body and placed in proximity to the stomach wall 12 of the patient, from the outside or inside thereof. The elongated member 650 has a special holding device 651 adapted to hold the stomach by means of mechanical grabbing members or vacuum. The special holding device 651 comprises a first joint 652 and a second joint 653, which enable the special holding device 651 be operable in relation to the elongated member 650 and thereby place the part of the holding device 651 comprising the mechanical grabbing members or vacuum elements into contact with the stomach wall 12 of the patient FIG. 19*b* shows the special holding device 651 when placed in contact with the stomach wall 12 of the human patient, after which the special holding member 651 connects to the stomach wall 12, for holding the stomach wall 12. FIG. 19*c* shows the instrument when the step of advancing a pushing rod 654 from the elongated member 650 is performed. The pushing rod 654 pushes the stomach wall 12 to create a cavity or pouch thereof. FIG. 19*d* shows the instrument turned 90° in relation to FIGS. 19*a-c*. This view shows the special holding members 651*a,b* operably attached to two sides of the elongated member 650 and being in contact with the stomach wall 12, holding the stomach wall 12 as the pushing rod 654 pushes to create a cavity or pouch. When the pushing rod 654 has pushed the stomach wall 12 to a desired position the special holding devices 651*a,b* moves towards the pushing rod 654 and thereby closes the cavity or pouch.

Figure 19F:
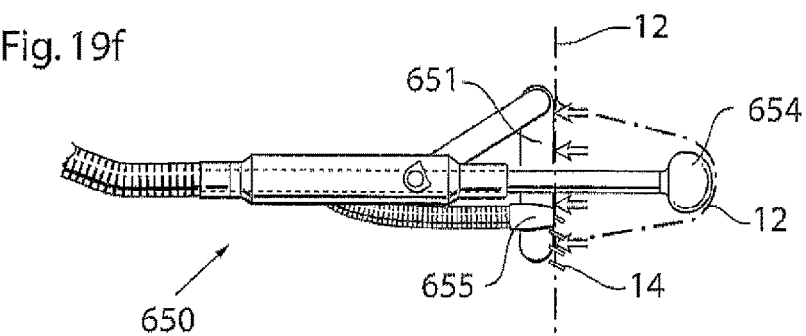
Figure 19G:
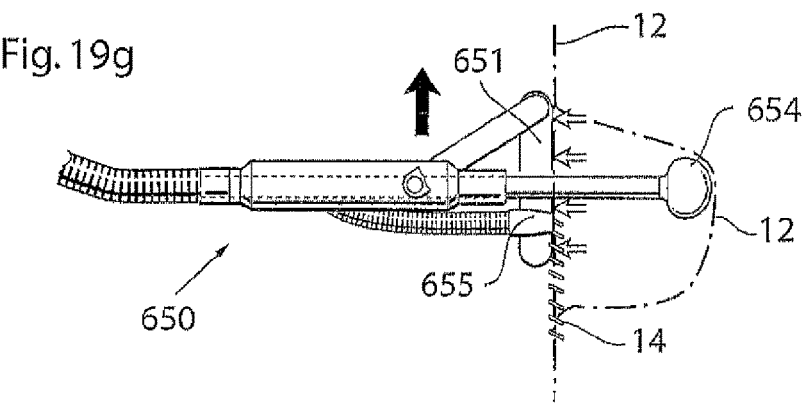
Figure 19H:
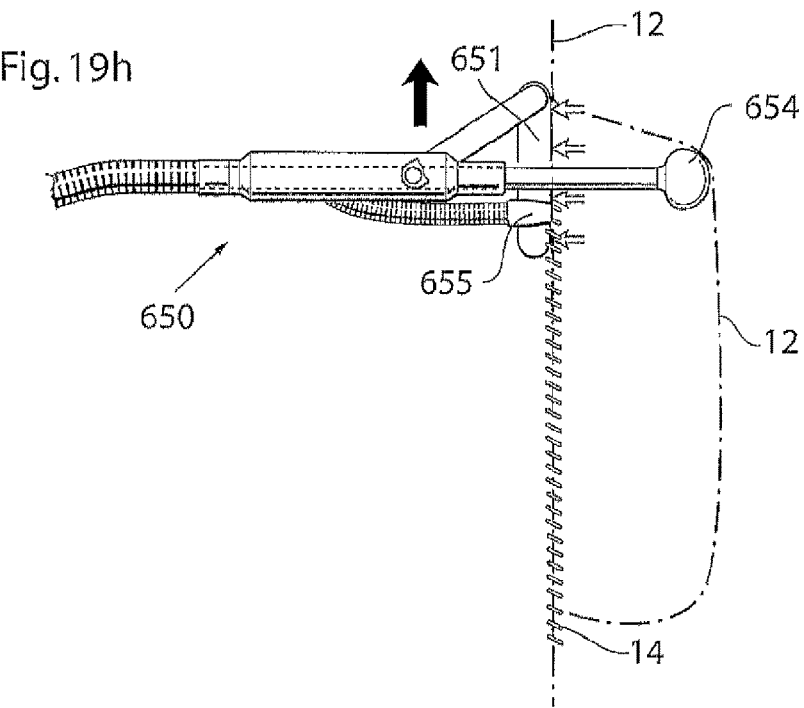
Figure 19I:
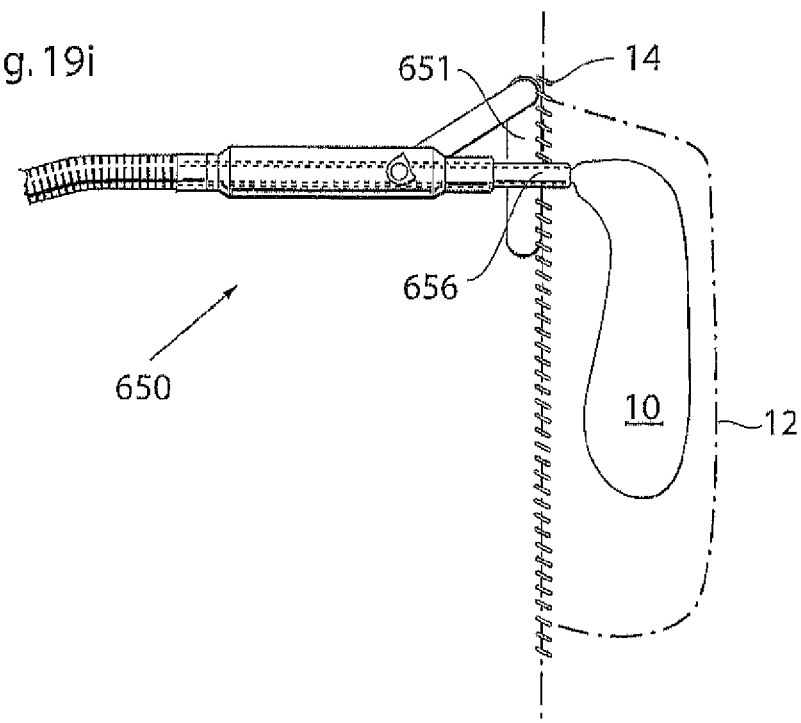
Figure 19J:
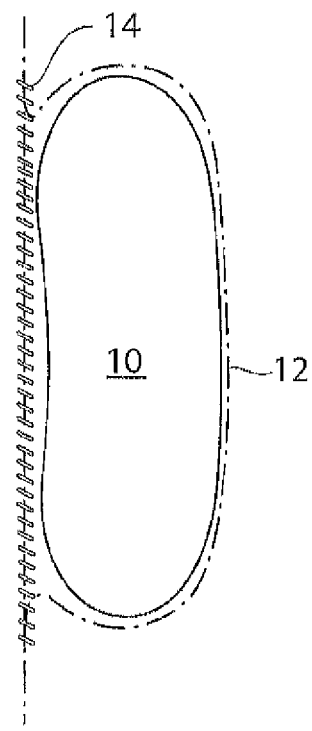

After the cavity or pouch has been created it needs to be sealed. FIG. 19*f* shows the advancement of a suturing or stapling device 655 from the elongated member 650. The suturing or stapling device 655 is positioned in connection with the stomach wall after which the suturing or stapling device commences with the suturing or stapling of the stomach wall 12, creating a seal of stomach to stomach sutures or staples 14. The instrument is moved along the stomach wall 12 of the patient and thereby a cavity or pouch is created and sealed using the instrument as shown in FIGS. 19*g* and 19*h*. When a cavity or pouch or desired size has been created and sealed an inserting member 656 is advanced from the elongated member 650. The inserting member 656 is adapted to insert a volume filling device 10 being inflatable, as described earlier in this application. After the inserting member 656 has been positioned in the cavity or pouch the volume filling device 10 is inserted through the inserting member 656 and into the cavity or pouch by means of a pressurized fluid or gas, or a mechanical advancement member pushing said inflatable volume filling device 10 into the cavity or pouch. The insertion member then inflates the inflatable volume filling device with a fluid or gas and seals of the final section of the pouch using stomach to stomach sutures or staples 14. The embodiment described explains the process of inserting an inflatable volume filling device, however it is equally conceivable that the volume filling device 10 is expandable by means of the volume filling device 10 being made of an elastic material.

Figure 20A:
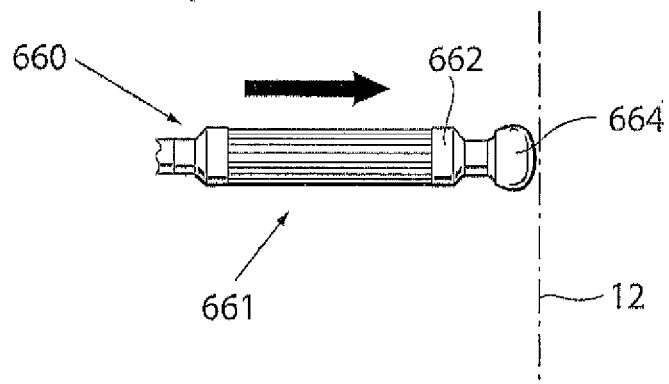
FIGS. 20a-f illustrate different steps of invaginating the inflatable device of FIG. 4a on the inside of a stomach wall of a patient.
Figure 20B:
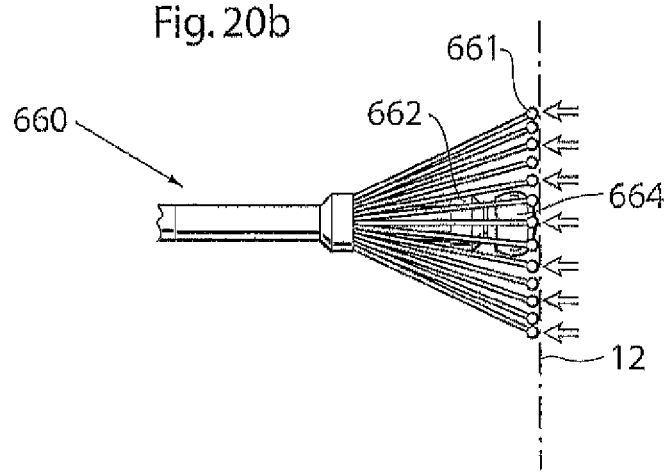
Figure 20C:
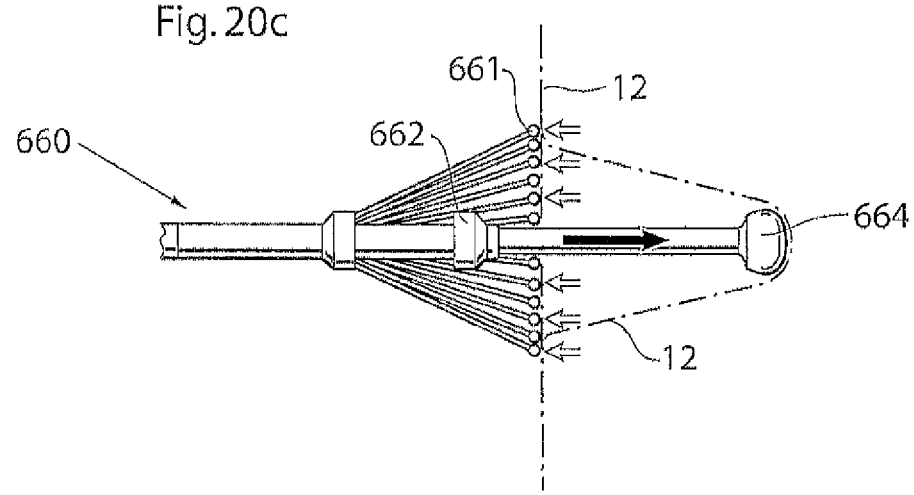

FIGS. 20*a-f* show an instrument for use in a method of engaging a volume filling device 10 to the stomach wall 12 of a patient. The instrument is adapted to be inserted through a narrow tube shaped object such as a gastro scope, used in an intraluminar procedure, or a laparoscopic trocar used in a laparoscopic procedure. The instrument comprises an elongated member 660 which is adapted to be flexible by means of a construction comprising multiple ring shaped members, however it is equally conceivable that said elongated member 660 is adapted to be flexible by means of said elongated member 660 being made of a flexible or adjustable material. The elongated member 660 is inserted into the body and placed in proximity to the stomach wall 12 of the patient, from the outside or inside thereof. The elongated member 660 has multiple special holding devices 661 adapted to hold the stomach by means of mechanical grabbing members or vacuum. The special holding devices 661 are locked in a position alongside the elongated member 660 by means of a locking ring 662. The special holding devices are made of a flexible material end pre-bent to expand into a funnel-shaped device when said locking ring 662 is removed. The special holding device in its funnel shaped expandable state is shown in FIG. 20*b*. FIG. 20*b* further shows the special holding device 661 when placed in contact with the stomach wall 12 of the human patient, after which the special holding member 661 connects to the stomach wall 12, for holding the stomach wall 12. FIG. 20*c* shows the instrument when the step of advancing a pushing rod 664 from the elongated member 660 is performed. The pushing rod 664 pushes the stomach wall 12 to create a cavity or pouch thereof. When the pushing rod 664 has pushed the stomach wall 12 to a desired position the special holding devices 661 moves towards the pushing rod 664 and thereby closes the cavity or pouch.

Figure 20D:
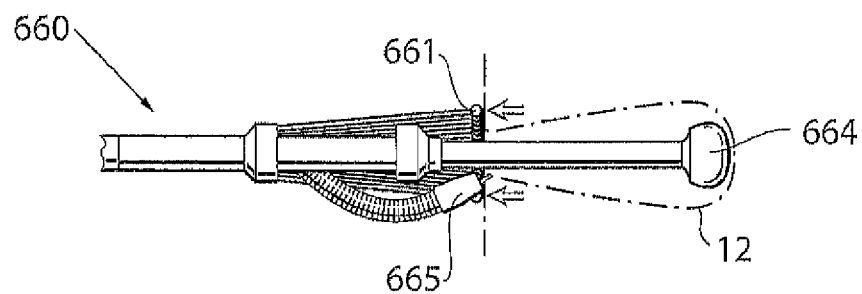
Figure 20E:
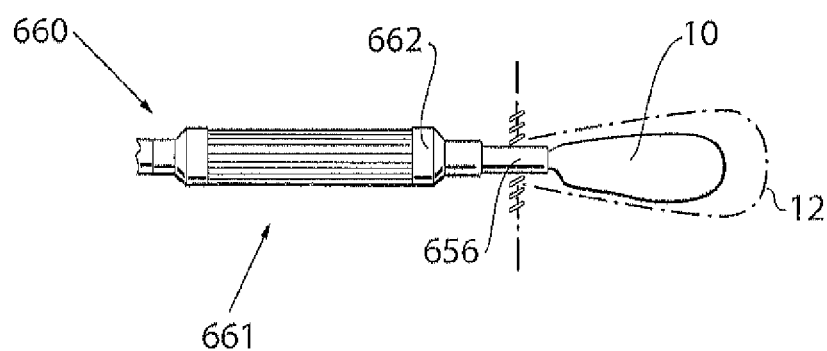
Figure 20F:
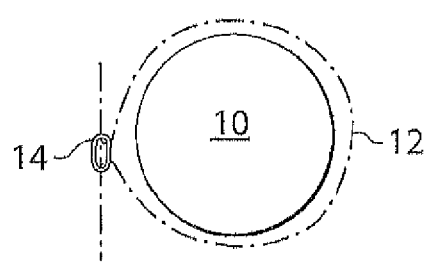

After the cavity or pouch has been created it needs to be sealed. FIG. 20*d* shows the advancement of a suturing or stapling device 665 from the elongated member 660. The suturing or stapling device 665 is positioned in connection with the stomach wall 12 after which the suturing or stapling device 665 commences with the suturing or stapling of the stomach wall 12, creating a seal of stomach to stomach sutures or staples 14. Thereafter an inserting member 666 is advanced from the elongated member 660 and the special holding devices 661 are retracted. The inserting member 666 is adapted to insert a volume filling device 10 being inflatable, as described earlier in this application. After the inserting member 666 has been positioned in the cavity or pouch the volume filling device 10 is inserted through the inserting member 666 and into the cavity or pouch by means of a pressurized fluid or gas, or a mechanical advancement member pushing said inflatable volume filling device 10 into the cavity or pouch. The insertion member 656 then inflates the inflatable volume filling device with a fluid or gas and seals of the final section of the pouch using stomach to stomach sutures or staples 14. The embodiment described explains the process of inserting an inflatable volume filling device 10, however it is equally conceivable that the volume filling device 10 is expandable by means of the volume filling device 10 being made of an elastic material. FIG. 20 *f* shows the volume filling device 10 as the volume filling device 10 is invaginated in the stomach wall 12, in a cavity or pouch sealed with stomach to stomach sutures or staples 14.

Figure 21A:
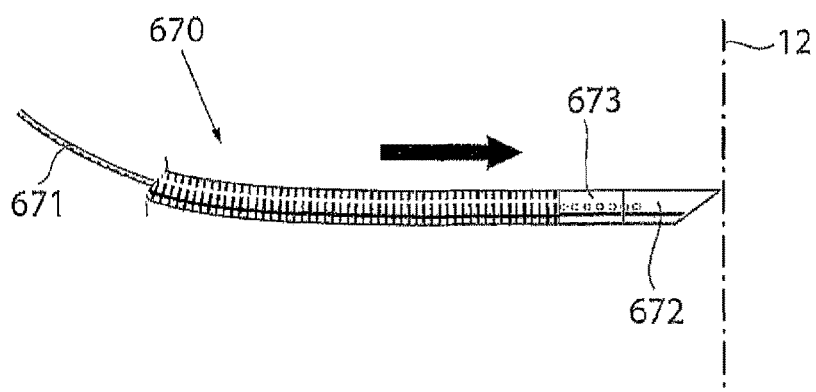
FIGS. 21a and 21b show instruments for surgically applying the implantable apparatus.

FIG. 21*a* shows an instrument used in a method of engaging the volume filling device according to any of the embodiments of the application to the stomach wall 12. The instrument comprises an elongated member 670 which is adapted to be flexible by means of a construction comprising multiple ring shaped members, however it is equally conceivable that said elongated member 670 is adapted to be flexible by means of said elongated member 670 being made of a flexible or adjustable material. The elongated member 670 is inserted into the body and placed in proximity to the stomach wall 12 of the patient, from the inside thereof. A stomach penetrating member 672 is placed in the distal end of the elongated member 670, retractably fixated to a protective sleeve 673 adapted to protect the tissue of the body from the sharp penetrating member 672 or cutter 672 after the cutting operation has been performed.

Figure 21B:
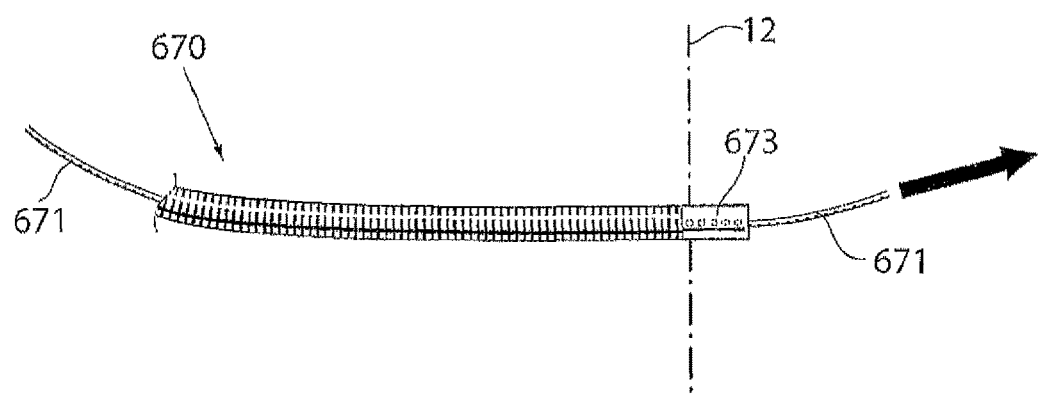

FIG. 21b shows the instrument comprising the elongated member 670 after the cutting operation has been performed and the stomach penetrating member or cutter 672 has been retracted into the protective sleeve 673. A guiding wire 671 is pushed through the elongated member 670, through the hole made in the stomach wall 12 and out through the abdomen and placed on the inside of the patients skin, which is penetrated from the outside to enable the guiding wire 671 to exit the abdomen. The guiding wire 671 can then be used to guide a conduit 18 or a lead attached to the volume filling device 10 being placed in the stomach from the inside thereof. The volume filling device 10 with the conduit 18 or electrical lead being a volume filling device 10 according to any of the embodiments of this application. The guiding of the conduit 18 or electrical lead enables the attachment of the conduit 18 or electrical lead to a control unit 42 placed subcutaneously in the patient from the outside of the abdomen.

FIG. 22 illustrates a system for treating a disease comprising an apparatus 10 comprising a volume filling device of the present invention placed in the abdomen of a patient. An implanted energy-transforming device 1002 is adapted to supply energy consuming components of the apparatus with energy via a power supply line 1003. An external energy-transmission device 1004 for non-invasively energizing the apparatus 10 transmits energy by at least one wireless energy signal. The implanted energy-transforming device 1002 transforms energy from the wireless energy signal into electric energy which is supplied via the power supply line 1003.

The implanted energy-transforming device 1002 may also comprise other components, such as: a coil for reception and/or transmission of signals and energy, an antenna for reception and/or transmission of signals, a microcontroller, a charge control unit, optionally comprising an energy storage, such as a capacitor, one or more sensors, such as temperature sensor, pressure sensor, position sensor, motion sensor etc., a transceiver, a motor, optionally including a motor controller, a pump, and other parts for controlling the operation of a medical implant.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 1004 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 1002 is provided for transforming wireless energy of a first form transmitted by the energy-transmission device 1004 into energy of a second form, which typically is different from the energy of the first form. The implanted apparatus 10 is operable in response to the energy of the second form. The energy-transforming device 1002 may directly power the apparatus with the second form energy, as the energy-transforming device 1002 transforms the first form energy transmitted by the energy-transmission device 1004 into the second form energy. The system may further include an implantable accumulator, wherein the second form energy is used at least partly to charge the accumulator.

Alternatively, the wireless energy transmitted by the energy-transmission device 1004 may be used to directly power the apparatus, as the wireless energy is being transmitted by the energy-transmission device 1004. Where the system comprises an operation device for operating the apparatus, as will be described below, the wireless energy transmitted by the energy-transmission device 1004 may be used to directly power the operation device to create kinetic energy for the operation of the apparatus.

The wireless energy of the first form may comprise sound waves and the energy-transforming device 1002 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 1004 also includes a wireless remote control having an external signal transmitter for transmitting a wireless control signal for non-invasively controlling the apparatus. The control signal is received by an implanted signal receiver which may be incorporated in the implanted energy-transforming device 1002 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 23 illustrates the system of FIG. 22 in the form of a more generalized block diagram showing the apparatus 10, the energy-transforming device 1002 powering the apparatus 10 via power supply line 1003, and the external energy-transmission device 1004. The patient's skin 1005, generally shown by a vertical line, separates the interior of the patient to the right of the line from the exterior to the left of the line.

FIG. 24 shows an embodiment of the invention identical to that of FIG. 23, except that a reversing device in the form of an electric switch 1006 operable for example by polarized energy also is implanted in the patient for reversing the apparatus 10. When the switch is operated by polarized energy the wireless remote control of the external energy-transmission device 1004 transmits a wireless signal that carries polarized energy and the implanted energy-transforming device 1002 transforms the wireless polarized energy into a polarized current for operating the electric switch 1006. When the polarity of the current is shifted by the implanted energy-transforming device 1002 the electric switch 1006 reverses the function performed by the apparatus 10.

FIG. 25 shows an embodiment of the invention identical to that of FIG. 23, except that an operation device 1007 implanted in the patient for operating the apparatus 10 is provided between the implanted energy-transforming device 1002 and the apparatus 10. This operation device can be in the form of a motor 1007, such as an electric servomotor. The motor 1007 is powered with energy from the implanted energy-transforming device 1002, as the remote control of the external energy-transmission device 1004 transmits a wireless signal to the receiver of the implanted energy-transforming device 1002.

FIG. 26 shows an embodiment of the invention identical to that of FIG. 23, except that it also comprises an operation device is in the form of an assembly 1008 including a motor/pump unit 1009 and a fluid reservoir 1010 is implanted in the patient. In this case the apparatus 10 is hydraulically operated, i.e. hydraulic fluid is pumped by the motor/pump unit 1009 from the fluid reservoir 1010 through a conduit 1011 to the apparatus 10 to operate the apparatus, and hydraulic fluid is pumped by the motor/pump unit 1009 back from the apparatus 10 to the fluid reservoir 1010 to return the apparatus to a starting position. The implanted energy-transforming device 1002 transforms wireless energy into a current, for example a polarized current, for powering the motor/pump unit 1009 via an electric power supply line 1012.

Instead of a hydraulically operated apparatus 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 1002 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 27:
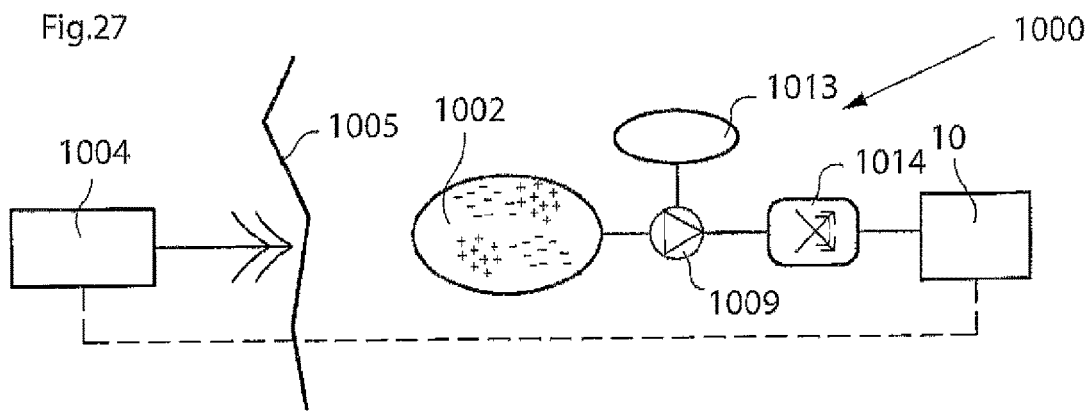

FIG. 27 shows an embodiment of the invention comprising the external energy-transmission device 1004 with its wireless remote control, the apparatus 10, in this case hydraulically operated, and the implanted energy-transforming device 1002, and further comprising a hydraulic fluid reservoir 1013, a motor/pump unit 1009 and an reversing device in the form of a hydraulic valve shifting device 1014, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 1009 is an electric motor. In response to a control signal from the wireless remote control of the external energy-transmission device 1004, the implanted energy-transforming device 1002 powers the motor/pump unit 1009 with energy from the energy carried by the control signal, whereby the motor/pump unit 1009 distributes hydraulic fluid between the hydraulic fluid reservoir 1013 and the apparatus 10. The remote control of the external energy-transmission device 1004 controls the hydraulic valve shifting device 1014 to shift the hydraulic fluid flow direction between one direction in which the fluid is pumped by the motor/pump unit 1009 from the hydraulic fluid reservoir 1013 to the apparatus 10 to operate the apparatus, and another opposite direction in which the fluid is pumped by the motor/pump unit 1009 back from the apparatus 10 to the hydraulic fluid reservoir 1013 to return the apparatus to a starting position.

Figure 28:
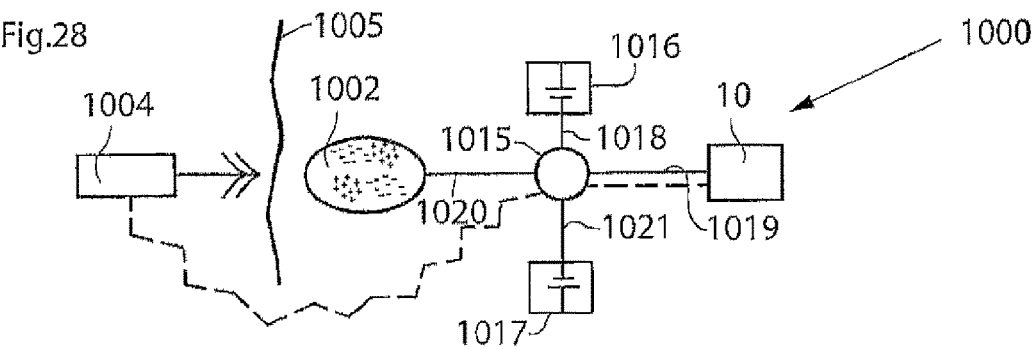

FIG. 28 shows an embodiment of the invention comprising the external energy-transmission device 1004 with its wireless remote control, the apparatus 10, the implanted energy-transforming device 1002, an implanted internal control unit 1015 controlled by the wireless remote control of the external energy transmission device 1004, an implanted accumulator 1016 and an implanted capacitor 1017. The internal control unit 1015 arranges storage of electric energy received from the implanted energy-transforming device 1002 in the accumulator 1016, which supplies energy to the apparatus 10. In response to a control signal from the wireless remote control of the external energy-transmission device 1004, the internal control unit 1015 either releases electric energy from the accumulator 1016 and transfers the released energy via power lines 1018 and 1019, or directly transfers electric energy from the implanted energy-transforming device 1002 via a power line 1020, the capacitor 1017, which stabilizes the electric current, a power line 1021 and the power line 1019, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physical parameter of the patient or any functional parameter of the system.

In accordance with an alternative, the capacitor 1017 in the embodiment of FIG. 28 10 may be omitted. In accordance with another alternative, the accumulator 1016 in this embodiment may be omitted.

Figure 29:
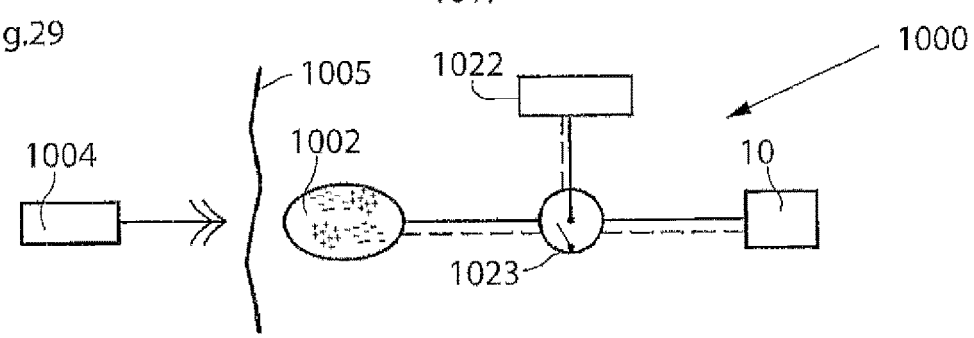

FIG. 29 shows an embodiment of the invention identical to that of FIG. 23, except that a battery 1022 for supplying energy for the operation of the apparatus 10 and an electric switch 1023 for switching the operation of the apparatus 10 also are implanted in the patient. The electric switch 1023 may be controlled by the remote control and may also be operated by the energy supplied by the implanted energy-transforming device 1002 to switch from an off mode, in which the battery 1022 is not in use, to an on mode, in which the battery 1022 supplies energy for the operation of the apparatus 10.

Figure 30:
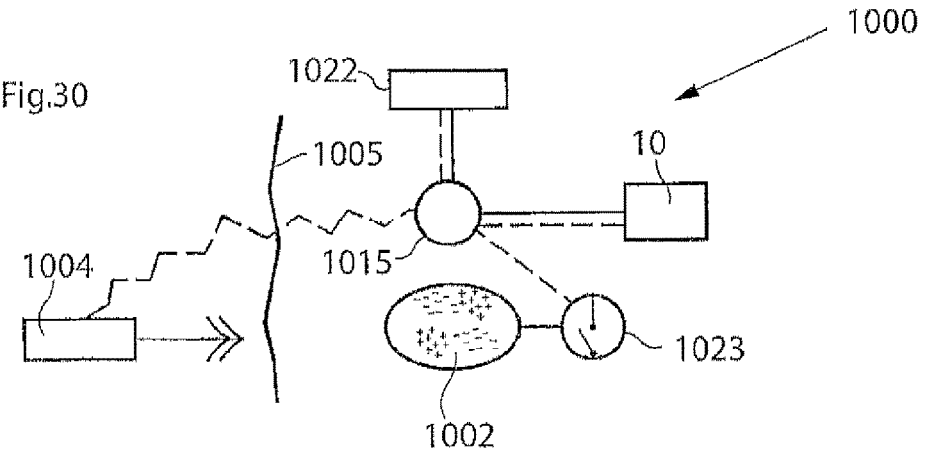

FIG. 30 shows an embodiment of the invention identical to that of FIG. 29, except that an internal control unit 1015 controllable by the wireless remote control of the external energy-transmission device 1004 also is implanted in the patient. In this case, the electric switch 1023 is operated by the energy supplied by the implanted energy-transforming device 1002 to switch from an off mode, in which the wireless remote control is prevented from controlling the internal control unit 1015 and the battery is not in use, to a standby mode, in which the remote control is permitted to control the internal control unit 1015 to release electric energy from the battery 1022 for the operation of the apparatus 10.

Figure 31:
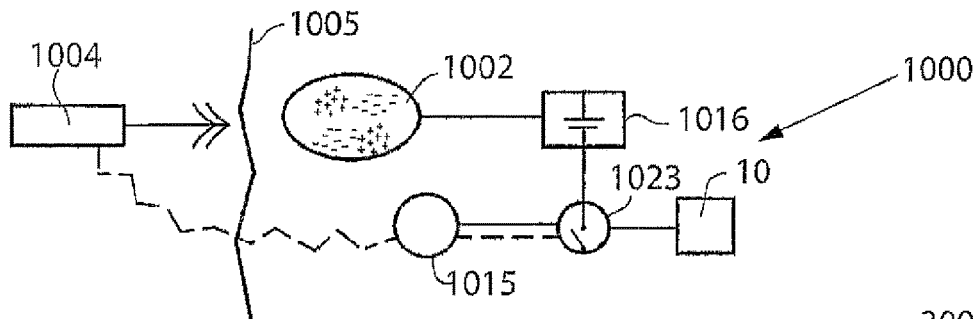

FIG. 31 shows an embodiment of the invention identical to that of FIG. 30, except that an accumulator 1016 is substituted for the battery 1022 and the implanted components are interconnected differently. In this case, the accumulator 1016 stores energy from the implanted energy-transforming device 1002. In response to a control signal from the wireless remote control of the external energy-transmission device 1004, the internal control unit 1015 controls the electric switch 1023 to switch from an off mode, in which the accumulator 1016 is not in use, to an on mode, in which the accumulator 1016 supplies energy for the operation of the apparatus 10. The accumulator may be combined with or replaced by a capacitor.

Figure 32:
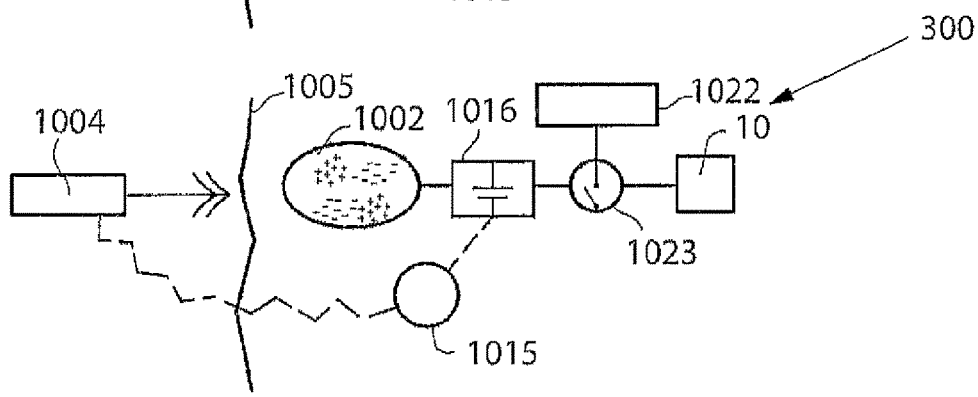

FIG. 32 shows an embodiment of the invention identical to that of FIG. 31, except that a battery 1022 also is implanted in the patient and the implanted components are interconnected differently. In response to a control signal from the wireless remote control of the external energy-transmission device 1004, the internal control unit 1015 controls the accumulator 1016 to deliver energy for operating the electric switch 1023 to switch from an off mode, in which the battery 1022 is not in use, to an on mode, in which the battery 1022 supplies electric energy for the operation of the apparatus 10.

Alternatively, the electric switch 1023 may be operated by energy supplied by the accumulator 1016 to switch from an off mode, in which the wireless remote control is prevented from controlling the battery 1022 to supply electric energy and is not in use, to a standby mode, in which the wireless remote control is permitted to control the battery 1022 to supply electric energy for the operation of the apparatus 10.

It should be understood that the switch 1023 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 33:
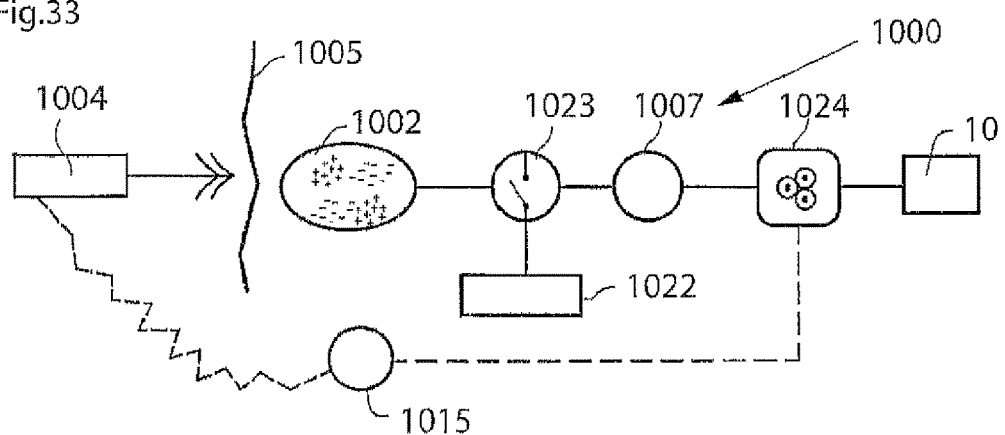

FIG. 33 shows an embodiment of the invention identical to that of FIG. 29, except that a motor 1007, a mechanical reversing device in the form of a gear box 1024, and an internal control unit 1015 for controlling the gearbox 1024 also are implanted in the patient. The internal control unit 1015 controls the gear box 1024 to reverse the function performed by the apparatus 10 (mechanically operated). Even simpler is to switch the direction of the motor electronically. The gearbox interpreted in its broadest embodiment may stand for a servo arrangement saving force for the operation device in favour of longer stroke to act.

Figure 34:
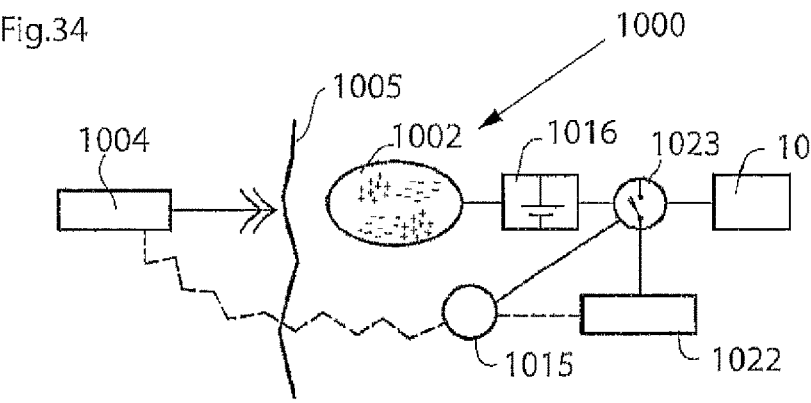
Figure 40:
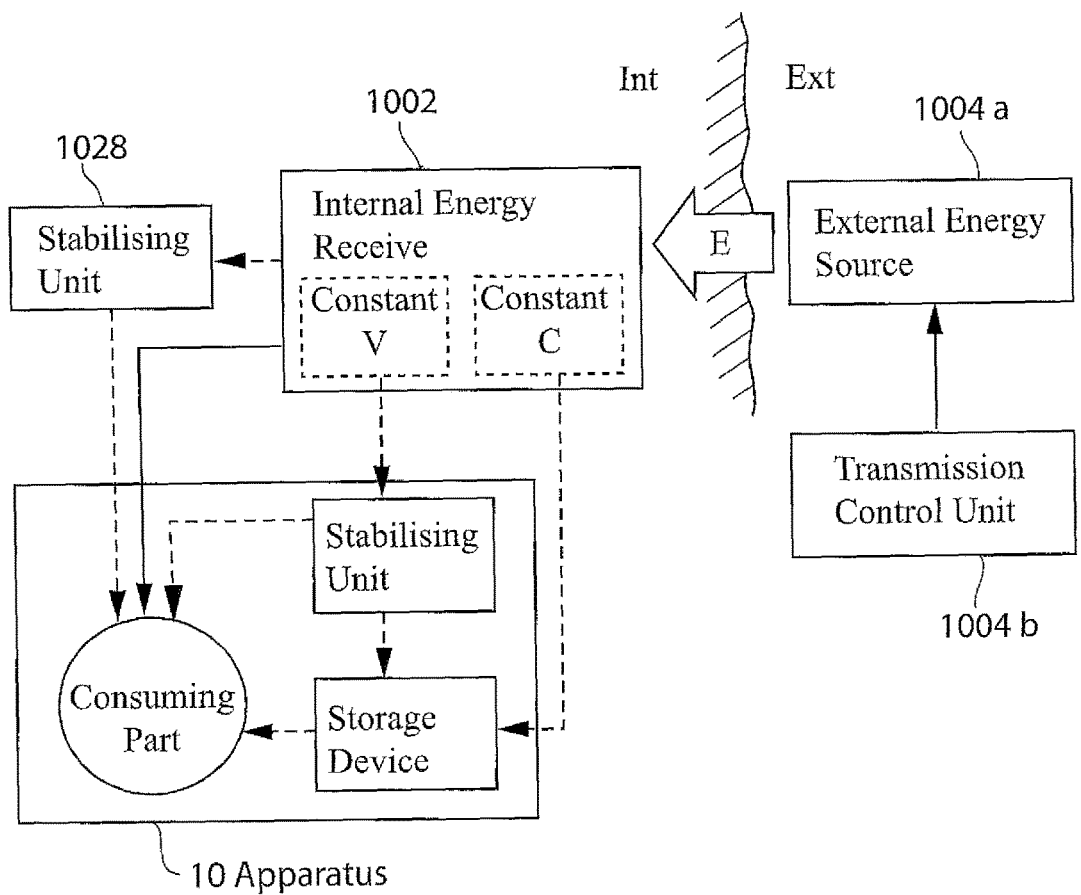

FIG. 34 shows an embodiment of the invention identical to that of FIG. 40 except that the implanted components are interconnected differently. Thus, in this case the internal control unit 1015 is powered by the battery 1022 when the accumulator 1016, suitably a capacitor, activates the electric switch 1023 to switch to an on mode. When the electric switch 1023 is in its on mode the internal control unit 1015 is permitted to control the battery 1022 to supply, or not supply, energy for the operation of the apparatus 10.

Figure 35:
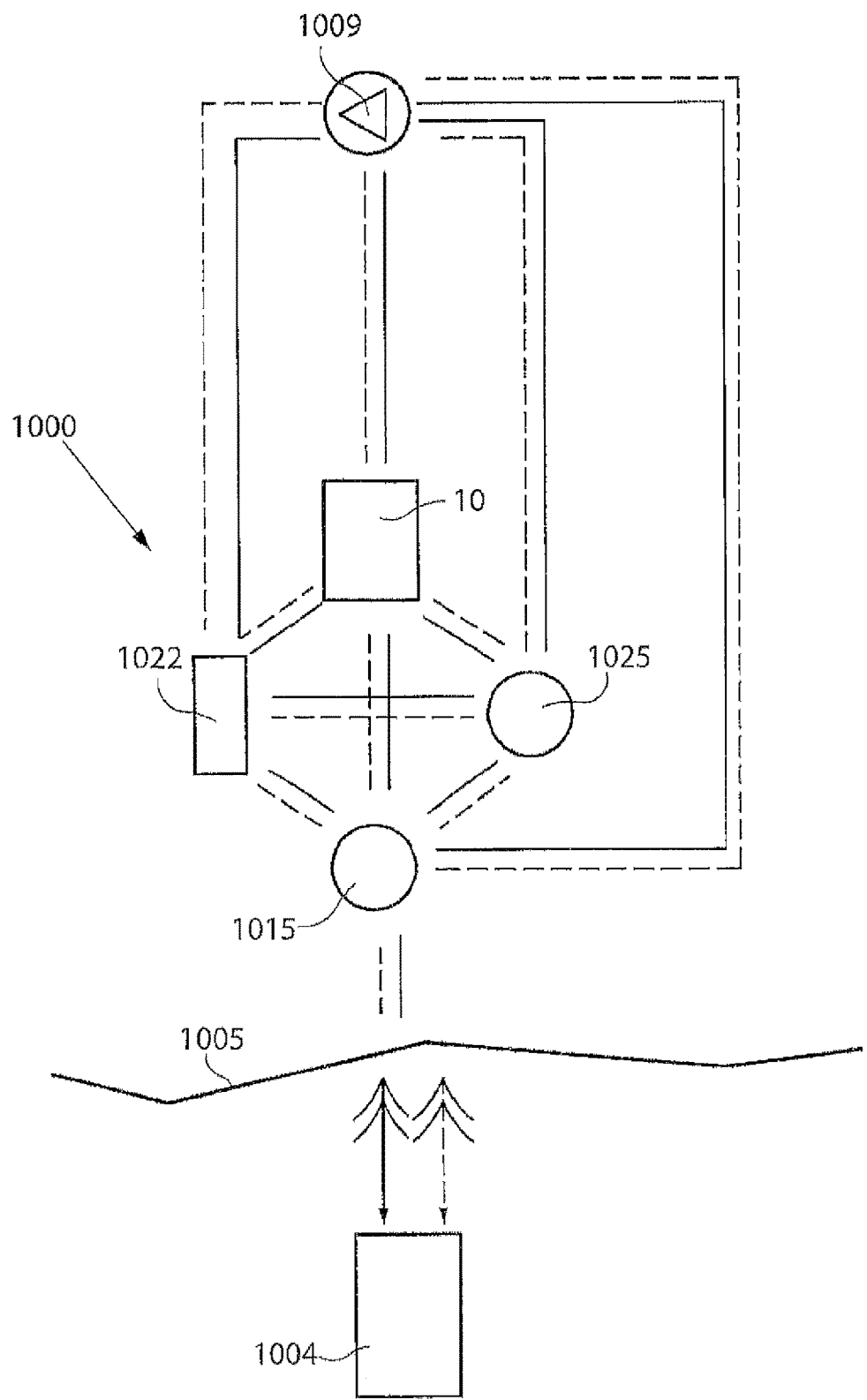

FIG. 35 schematically shows conceivable combinations of implanted components of the apparatus for achieving various communication options. Basically, there are the apparatus 10, the internal control unit 1015, motor or pump unit 1009, and the external energy-transmission device 1004 including the external wireless remote control. As already described above the wireless remote control transmits a control signal which is received by the internal control unit 1015, which in turn controls the various implanted components of the apparatus.

A feedback device, preferably comprising a sensor or measuring device 1025, may be implanted in the patient for sensing a physical parameter of the patient. The physical parameter may be at least one selected form the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 1025 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 1015, or alternatively the external wireless remote control of the external energy-transmission device 1004, may control the apparatus 10 in response to signals from the sensor 1025. A transceiver may be combined with the sensor 1025 for sending information on the sensed physical parameter to the external wireless remote control. The wireless remote control may comprise a signal transmitter or transceiver and the internal control unit 1015 may comprise a signal receiver or transceiver. Alternatively, the wireless remote control may comprise a signal receiver or transceiver and the internal control unit 1015 may comprise a signal transmitter or transceiver. The above transceivers, transmitters and receivers may be used for sending information or data related to the apparatus 10 from inside the patient's body to the outside thereof.

Where the motor/pump unit 1009 and battery 1022 for powering the motor/pump unit 1009 are implanted, information related to the charging of the battery 1022 may be fed back. To be more precise, when charging a battery or accumulator with energy feedback information related to said charging process is sent and the energy supply is changed accordingly.

Figure 36:
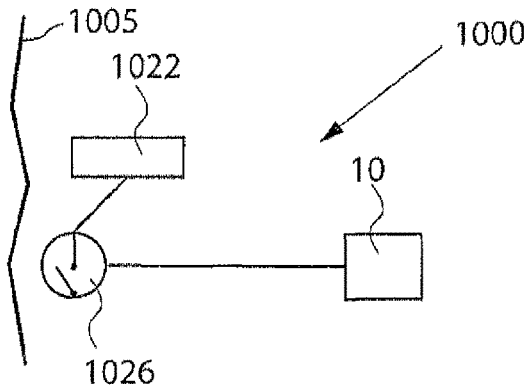

FIG. 36 shows an alternative embodiment wherein the apparatus 10 is regulated from outside the patient's body. The system 1000 comprises a battery 1022 connected to the apparatus 10 via a subcutaneous electric switch 1026. Thus, the regulation of the apparatus 10 is performed non-invasively by manually pressing the subcutaneous switch, whereby the operation of the apparatus 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 37:
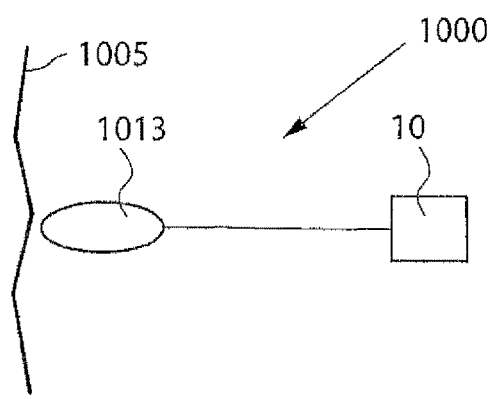

FIG. 37 shows an alternative embodiment, wherein the system 1000 comprises a hydraulic fluid reservoir 1013 hydraulically connected to the apparatus. Non-invasive regulation is performed by manually pressing the hydraulic reservoir connected to the apparatus. Alternatively, the hydraulic fluid reservoir 1013 is adapted to work with an injection port for the injection of hydraulic fluid, preferably for calibration of hydraulic fluid.

The system may include an external data communicator and an implantable internal data communicator communicating with the external data communicator. The internal communicator feeds data related to the apparatus or the patient to the external data communicator and/or the external data communicator feeds data to the internal data communicator.

Figure 38:
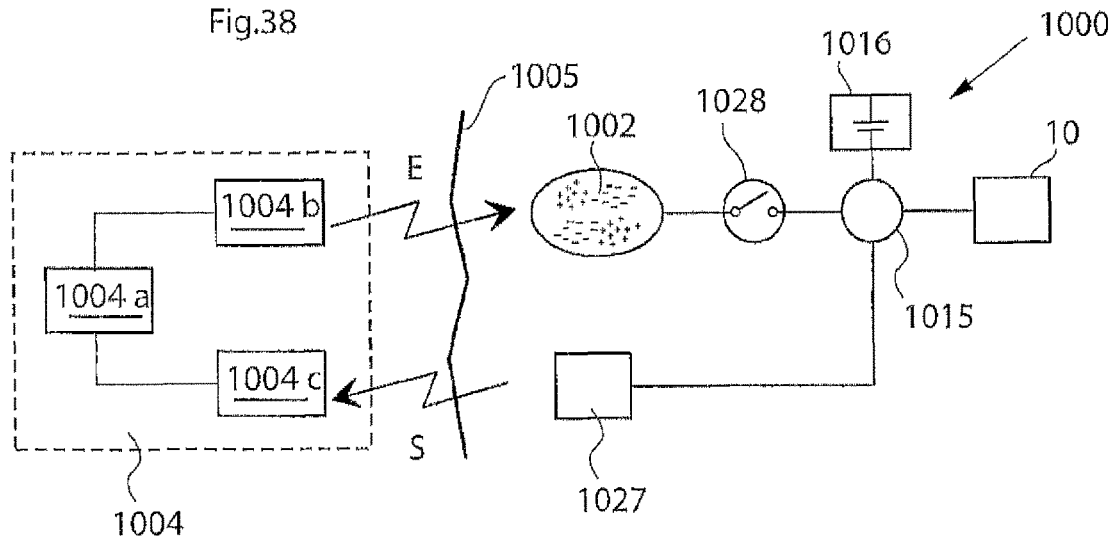

FIG. 38 schematically illustrates an arrangement of the system that is capable of sending information from inside the patient's body to the outside thereof to give feedback information related to at least one functional parameter of the apparatus or system, or related to a physical parameter of the patient, in order to supply an accurate amount of energy to an implanted internal energy receiver 1002 connected to implanted energy consuming components of the apparatus 10. Such an energy receiver 1002 may include an energy source and/or an energy-transforming device. Briefly described, wireless energy is transmitted from an external energy source 1004a located outside the patient and is received by the internal energy receiver 1002 located inside the patient. The internal energy receiver is adapted to directly or indirectly supply received energy to the energy consuming components of the apparatus 10 via a switch 1026. An energy balance is determined between the energy received by the internal energy receiver 1002 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIG. 38 the patient's skin is indicated by a vertical line 1005. Here, the energy receiver comprises an energy-transforming device 1002 located inside the patient, preferably just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from the external energy-source 1004a provided in an external energy-transmission device 1004 located outside the patients skin 1005 in the vicinity of the implanted energy-transforming device 1002.

As is well known in the art, the wireless energy E may generally be transferred by means of any suitable Transcutaneous Energy Transfer (TET) device, such as a device including a primary coil arranged in the external energy source 1004a and an adjacent secondary coil arranged in the implanted energy-transforming device 1002. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 1004b that controls the external energy source 1004a based on the determined energy balance to regulate the amount of transferred energy. In order to transfer the correct amount of energy, the energy balance and the required amount of energy is determined by means of a determination device including an implanted internal control unit 1015 connected between the switch 1026 and the apparatus 10. The internal control unit 1015 may thus be arranged to receive various measurements obtained by suitable sensors or the like, not shown, measuring certain characteristics of the apparatus 10, somehow reflecting the required amount of energy needed for proper operation of the apparatus 10. Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the control unit 1015 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the apparatus 10, or the patients or an implanted energy source if used, or any combination thereof. The internal control unit 1015 is further connected to an internal signal transmitter 1027, arranged to transmit a control signal reflecting the determined required amount of energy, to an external signal receiver 1004c connected to the external control unit 1004b. The amount of energy transmitted form the external energy source 1004a may then be regulated in response to the received control signal.

Alternatively, the determination device may include the external control unit 1004b. In this alternative, sensor measurements can be transmitted directly to the external control unit 1004b wherein the energy balance and/or the currently required amount of energy can be determined by the external control unit 1004b, thus integrating the above-described function of the internal control unit 1015 in the external control unit 1004b. In that case, the internal control unit 1015 can be omitted and the sensor measurements are supplied directly to the internal signal transmitter 1027 which sends the measurements over to the external signal receiver 1004c and the external control unit 1004b. The energy balance and the currently required amount of energy can then be determined by the external control unit 1004b based on those sensor measurements.

Hence, the present solution according to the arrangement of FIG. 38 employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 1027 and the external signal receiver 1004c may be implemented as separate units using suitable signal transfer means, such as radio, IR (Infrared) or ultrasonic signals. Alternatively, the internal signal transmitter 1027 and the external signal receiver 1004c may be integrated in the implanted energy-transforming device 1002 and the external energy source 1004a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 38, the switch 1026 is either separate and controlled by the internal control unit 1015, or integrated in the internal control unit 1015. It should be understood that the switch 1026 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 38 may operate basically in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004c. Alternatively, the energy balance can be determined by the external control unit 1004b instead depending on the implementation, as mentioned above. In that case, the control signal may carry measurement results from various sensors. The amount of energy emitted from the external energy source 1004a can then be regulated by the external control unit 1004b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 39:
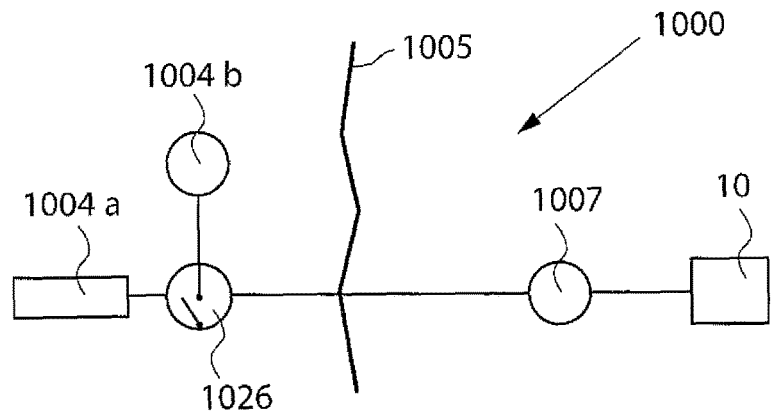

With reference to FIG. 39, although wireless transfer of energy for operating the apparatus has been described above to enable non-invasive operation, it will be appreciated that the apparatus can be operated with wire bound energy as well. Such an example is shown in FIG. 39, wherein an external switch 1026 is interconnected between the external energy source 1004a and an operation device, such as an electric motor 1007 operating the apparatus 10. An external control unit 1004b controls the operation of the external switch 1026 to effect proper operation of the apparatus 10.

FIG. 40 illustrates different embodiments for how received energy can be supplied to and used by the apparatus 10. Similar to the example of FIG. 38, an internal energy receiver 1002 receives wireless energy E from an external energy source 1004a which is controlled by a transmission control unit 1004b. The internal energy receiver 1002 may comprise a constant voltage circuit, indicated as a dashed box "constant V" in the figure, for supplying energy at constant voltage to the apparatus 10. The internal energy receiver 1002 may further comprise a constant current circuit, indicated as a dashed box "constant C" in the figure, for supplying energy at constant current to the apparatus 10.

The apparatus 10 comprises an energy consuming part, which may be a motor, pump, restriction device, or any other medical appliance that requires energy for its electrical operation. The apparatus 10 may further comprise an energy storage device for storing energy supplied from the internal energy receiver 1002. Thus, the supplied energy may be directly consumed by the energy consuming part, or stored by the energy storage device, or the supplied energy may be partly consumed and partly stored. The apparatus 10 may further comprise an energy stabilizing unit for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the apparatus 10, before being consumed and/or stored by the apparatus 10. Alternatively, the energy stabilizing unit 1028 may be integrated in the internal energy receiver 1002. In either case, the energy stabilizing unit 1028 may comprise a constant voltage circuit and/or a constant current circuit.

It should be noted that FIG. 38 and FIG. 40 illustrate some possible but non-limiting implementation options regarding how the various shown functional components and elements can be arranged and connected to each other. However, the skilled person will readily appreciate that many variations and modifications can be made within the scope of the present invention.

Figure 41:
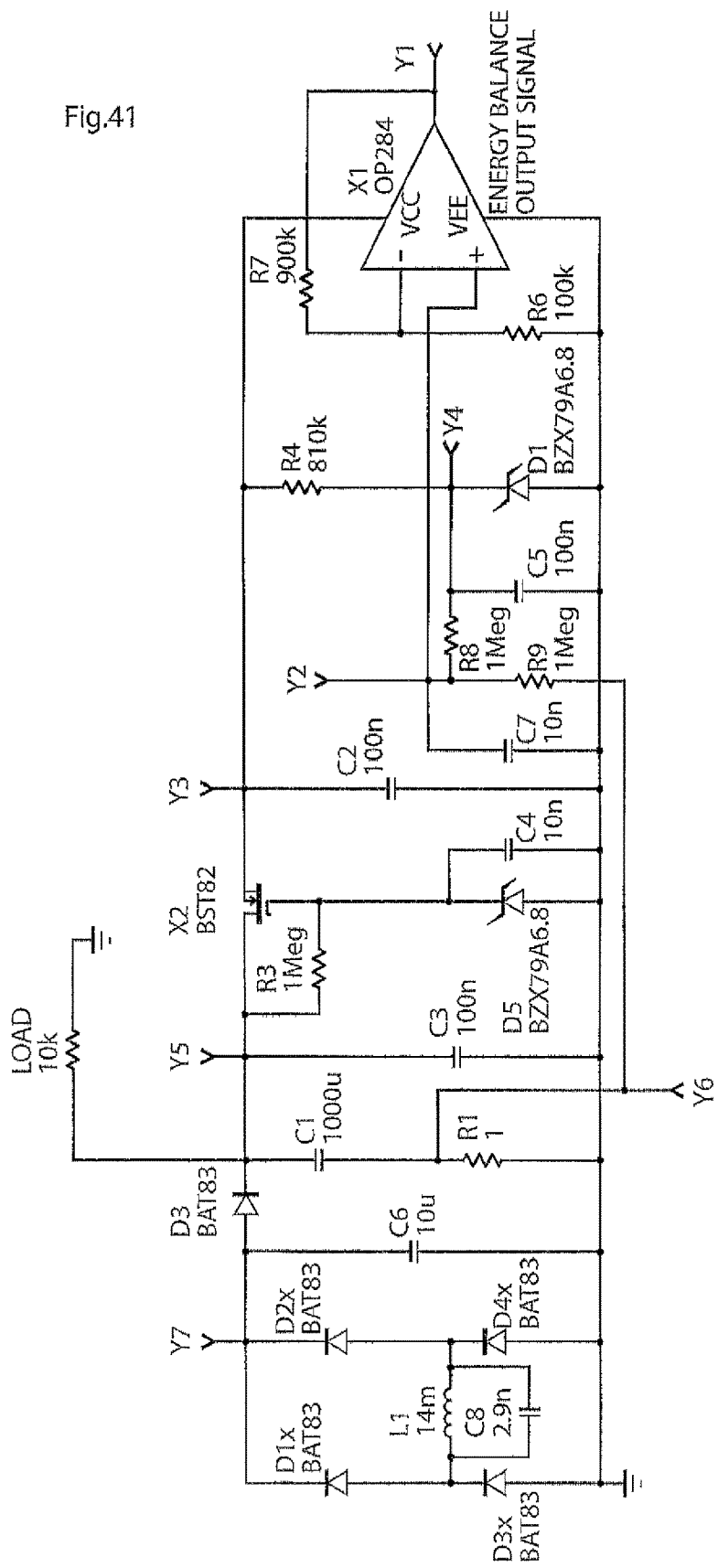

FIG. 41 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 41 shows a circuit implementation for a system that transfers energy to the implanted energy components of the apparatus of the present invention from outside of the patient's body using inductive energy transfer. An inductive energy transfer system typically uses an external transmitting coil and an internal receiving coil. The receiving coil, L1, is included in the schematic FIG. 24; the transmitting parts of the system are excluded.

The implementation of the general concept of energy balance and the way the information is transmitted to the external energy transmitter can of course be implemented in numerous different ways. The schematic FIG. 41 and the above described method of evaluating and transmitting the information should only be regarded as examples of how to implement the control system.

Circuit Details

In FIG. 41 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 1006 of FIG. 24 could be incorporated in any of the embodiments of FIGS. 27-33, the hydraulic valve shifting device 1014 of FIG. 27 could be incorporated in the embodiment of FIG. 26, and the gearbox 1024 could be incorporated in the embodiment of FIG. 25. Please observe that the switch simply could mean any electronic circuit or component.

The embodiments described in connection with FIGS. 38, 40 and 41 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

In one embodiment at least one battery may be a part of or replace the energy-transforming device 1002 to supply energy to the apparatus 10 over a power supply line. In one embodiment the battery is not rechargeable. In an alternative embodiment the battery is rechargeable. The battery supply may of course be placed both remote to and incorporated in the device.

Further, the system may comprise any of the following features:

- A primary coil in the external energy source adapted to transmit the wireless energy inductively to a secondary coil in the internal energy receiver.
- The determination device is adapted to detect a change in the energy balance, and the control device controls the transmission of wireless energy based on the detected energy balance change
- The determination device is adapted to detect a difference between energy received by the internal energy receiver and energy used for the implantable energy consuming components of the apparatus, and the control device controls the transmission of wireless energy based on the detected energy difference.
- The control device controls the external energy-transmission device to decrease the amount of transmitted wireless energy if the detected energy balance change implies that the energy balance is increasing, or vice versa, wherein the decrease/increase of energy transmission corresponds to a detected change rate.
- The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for the apparatus is consumed to operate the apparatus, and/or stored in at least one energy storage device of the apparatus.

Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a rain of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 42-45 show in more detail block diagrams of four different ways of hydraulically or pneumatically powering an implanted apparatus according to the invention.

Figure 42:
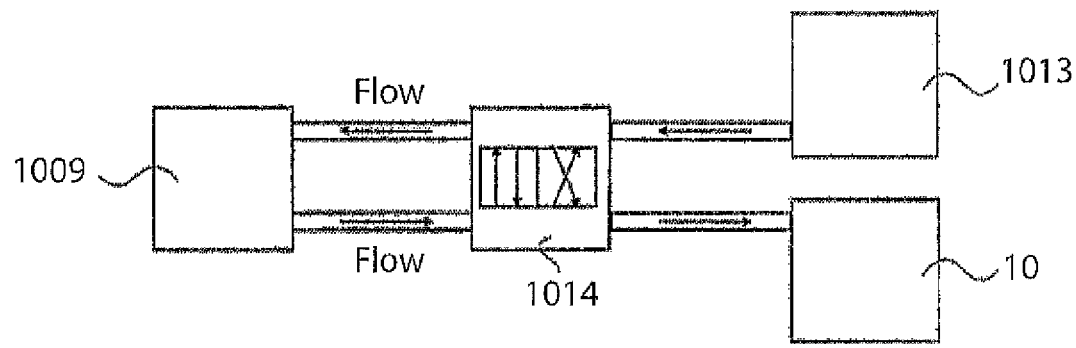
FIGS. 42-45, 46a-c, 47, and 48a-c show various ways of arranging hydraulic or pneumatic powering of an apparatus for treating obesity implanted in a human patient.

FIG. 42 shows a system as described above with. The system comprises an implanted apparatus 10 and further a separate regulation reservoir 1013, a one way pump 1009 and an alternate valve 1014.

Figure 43:

FIG. 43 shows the apparatus 10 and a fluid reservoir 1013. By moving the wall of the regulation reservoir or changing the size of the same in any other different way, the adjustment of the apparatus may be performed without any valve, just fee passage of fluid any time by moving the reservoir wall.

Figure 44:
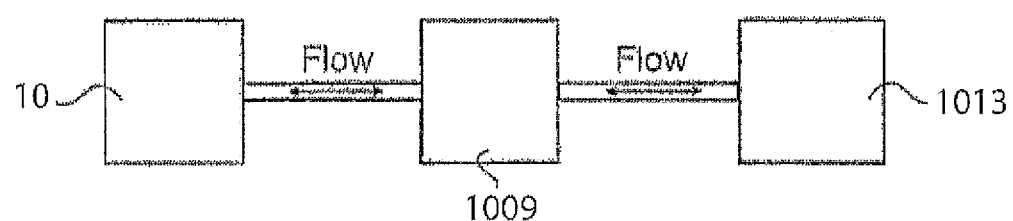

FIG. 44 shows the apparatus 10, a two way pump 1009 and the regulation reservoir 1013.

Figure 45:
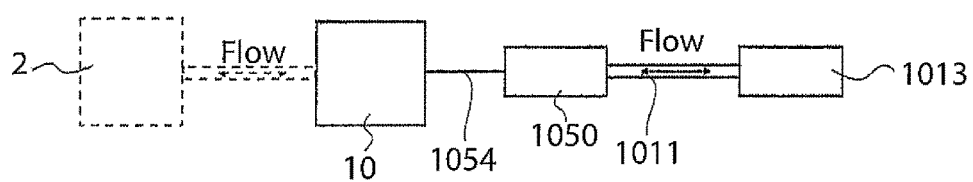

FIG. 45 shows a block diagram of a reversed servo system with a first closed system controlling a second closed system. The servo system comprises a regulation reservoir 1013 and a servo reservoir 1050. The servo reservoir 1050 mechanically controls an implanted apparatus 10 via a mechanical interconnection 1054. The apparatus has an expandable/contactable cavity. This cavity is preferably expanded or contracted by supplying hydraulic fluid from the larger adjustable reservoir 1052 in fluid connection with the apparatus 10. Alternatively, the cavity contains compressible gas, which can be compressed and expanded under the control of the servo reservoir 1050.

The servo reservoir 1050 can also be part of the apparatus itself.

Figure 46A:
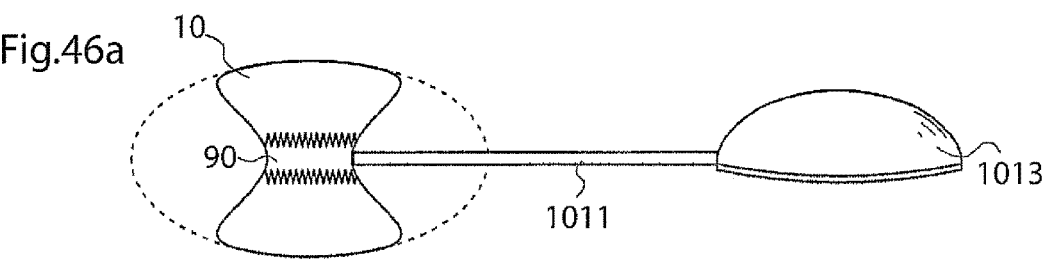
Figure 46B:
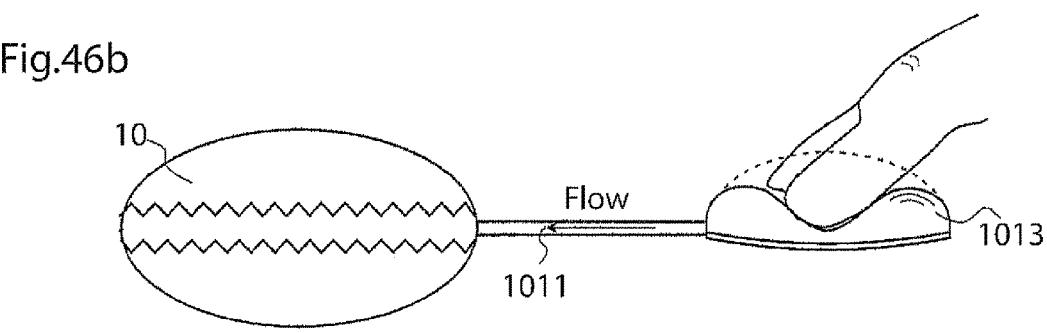
Figure 46C:
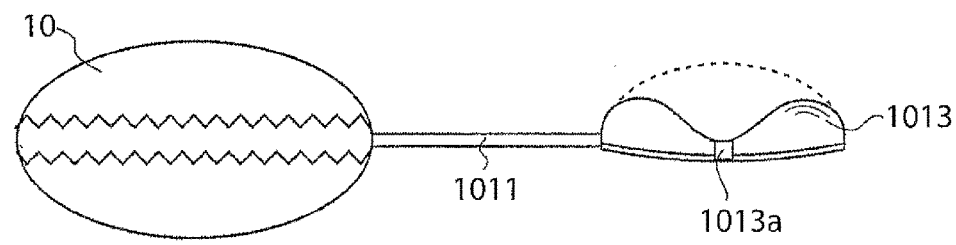
Figure 47:
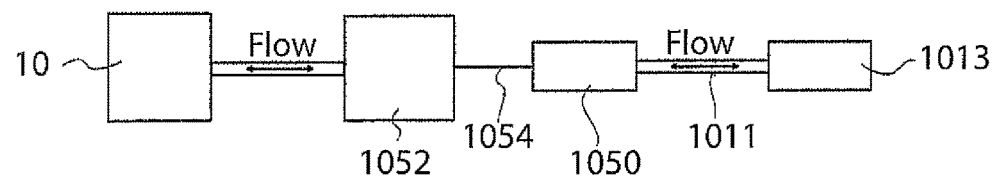

In one embodiment, the regulation reservoir is placed subcutaneous under the patient's skin and is operated by pushing the outer surface thereof by means of a finger. This system is illustrated in FIGS. 46*a-c*. In FIG. 46*a*, a flexible subcutaneous regulation reservoir 1013 is shown connected to a bulge shaped servo reservoir 1050 by means of a conduit 1011. This bellow shaped servo reservoir 1050 is comprised in a flexible apparatus 10. In the state shown in FIG. 46*a*, the servo reservoir 1050 contains a minimum of fluid and most fluid is found in the regulation reservoir 1013. Due to the mechanical interconnection between the servo reservoir 1050 and the apparatus 10, the outer shape of the apparatus 10 is contracted, i.e., it occupies less than its maximum volume. This maximum volume is shown with dashed lines in the figure.

FIG. 46*b* shows a state wherein a user, such as the patient in with the apparatus is implanted, presses the regulation reservoir 1013 so that fluid contained therein is brought to flow through the conduit 1011 and into the servo reservoir 1050, which, thanks to its bellow shape, expands longitudinally. This expansion in turn expands the apparatus 10 so that it occupies its maximum volume, thereby stretching the stomach wall (not shown), which it contacts.

The regulation reservoir 1013 is preferably provided with means 1013*a* for keeping its shape after compression. This means, which is schematically shown in the figure, will thus keep the apparatus 10 in a stretched position also when the user releases the regulation reservoir. In this way, the regulation reservoir essentially operates as an on/off switch for the system.

An alternative embodiment of hydraulic or pneumatic operation will now be described with reference to FIGS. 47 and 48*a*-*c*. The block diagram shown in FIG. 47 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted apparatus 10 having an expandable/contactable cavity is in turn controlled by the larger adjustable reservoir 1052 by supply of hydraulic fluid from the larger adjustable reservoir 1052 in fluid connection with the apparatus 10.

Figure 48A:
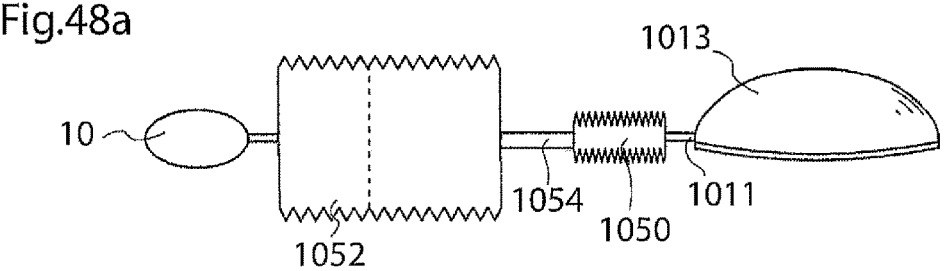
Figure 48B:
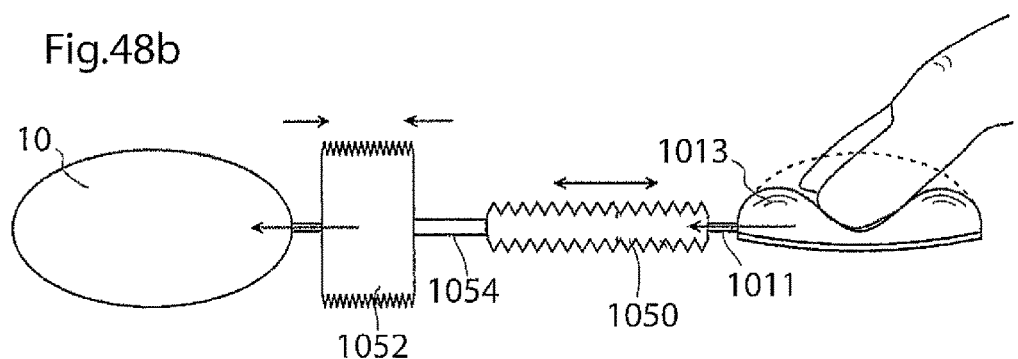
Figure 48C:
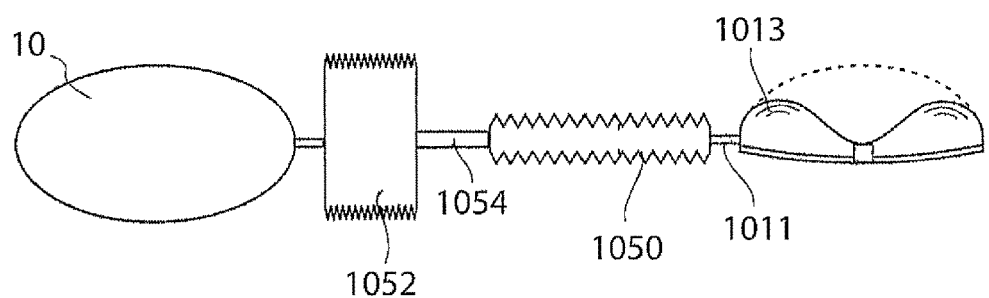

An example of this embodiment will now be described with reference to FIG. 48*a*-*c*. Like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 48*a*, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the apparatus 10. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the apparatus 10. In other words, in this reversed servo, a small volume in the regulation reservoir is compressed with a higher force and this creates a movement of a larger total area with less force per area unit.

Like in the previous embodiment described above with reference to FIGS. 46*a*-*c*, the regulation reservoir 1013 is preferably provided with means 1013*a* for keeping its shape after compression. This means, which is schematically shown in the figure, will thus keep the apparatus 10 in a stretched position also when the user releases the regulation reservoir. In this way, the regulation reservoir essentially operates as an on/off switch for the system.

Figure 49:
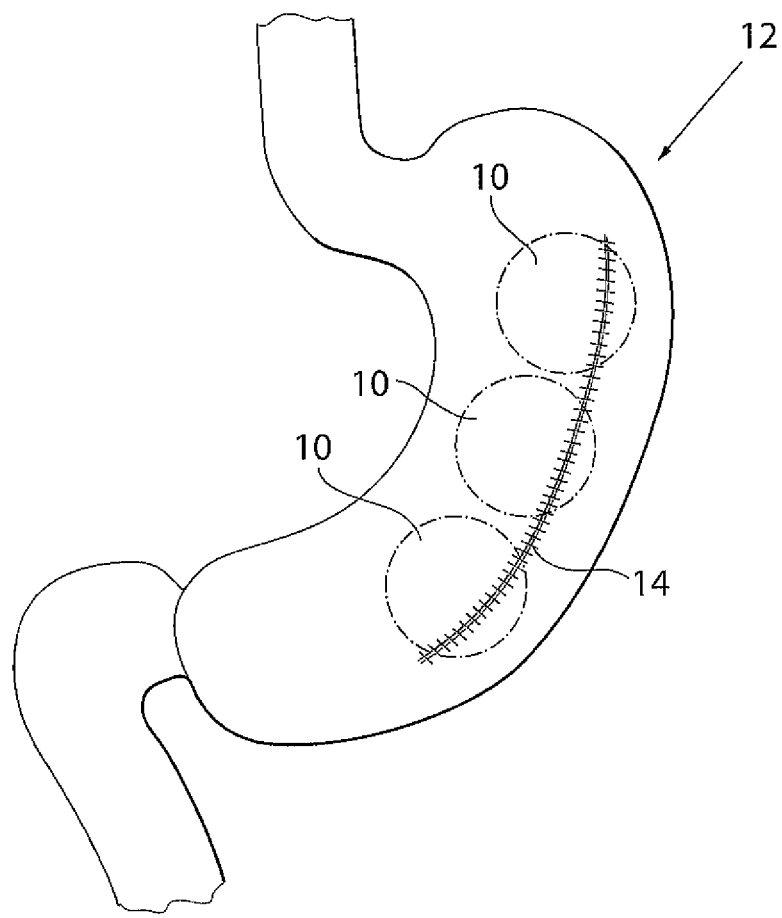
FIG. 49 illustrate the invagination of a plurality volume filling devices.

One single volume filling device has been described as invaginated in the stomach wall. Alternatively, two or more volume filling devices 10 may be invaginated to obtain the desired reduction of the food cavity. One such example is illustrated in FIG. 49, wherein three ball-shaped volume filling devices 10 are invaginated in the wall of the patient's stomach 12.

It has been described how the volume filling device 10 is invaginated in the stomach wall by means of a gastroscopic instrument. It will be appreciated that abdominal operation methods can be used as well. Such methods will now be described in detail with reference to FIGS. 50*a* and 50*b*.

Figure 50:
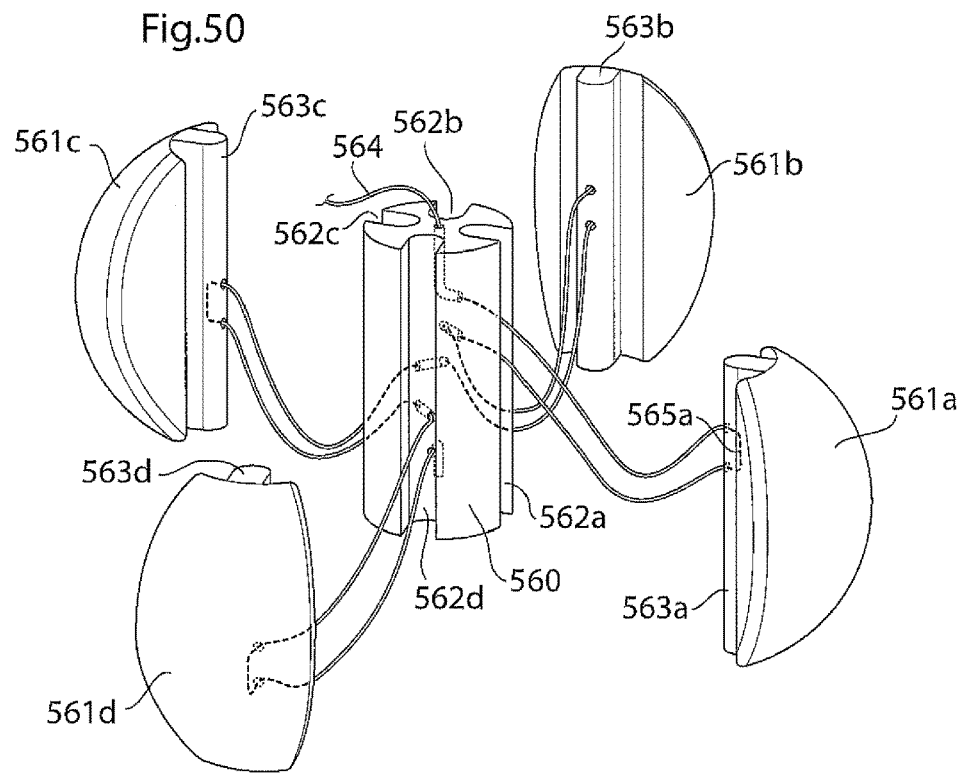
FIG. 50 shows an embodiment of the volume filling device in segments before assembly.
Figure 51:
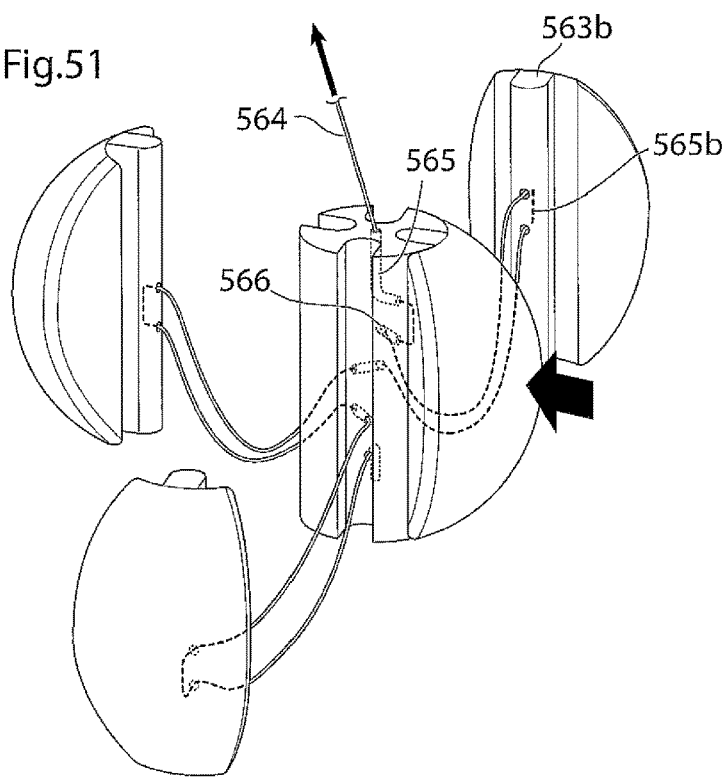
FIG. 51 shows an embodiment of the volume filling device when first part and second part are assembled.
Figure 52:
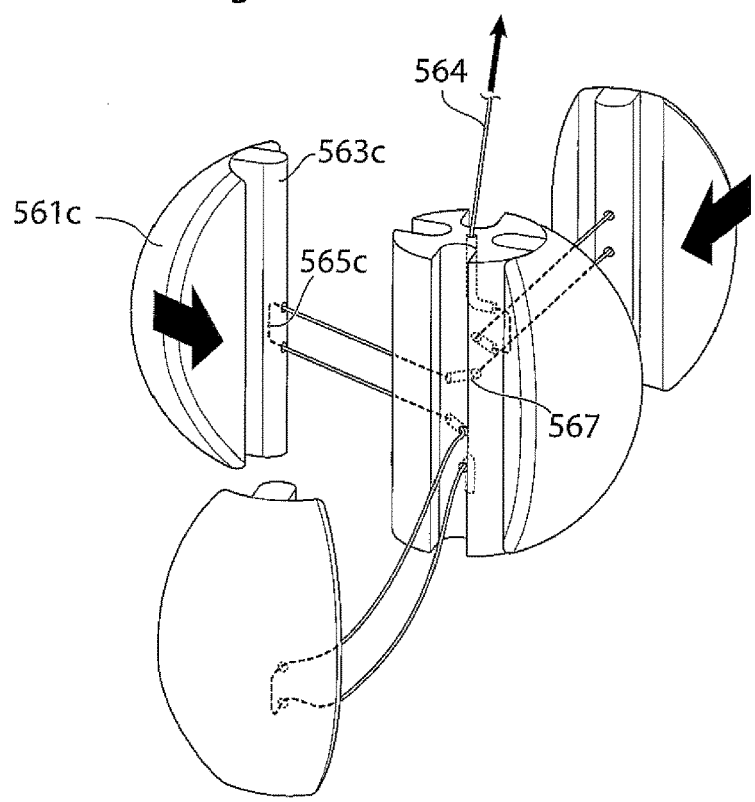
FIG. 52 shows the embodiment of FIG. 51 when a third and a fourth part are assembled.
Figure 53:
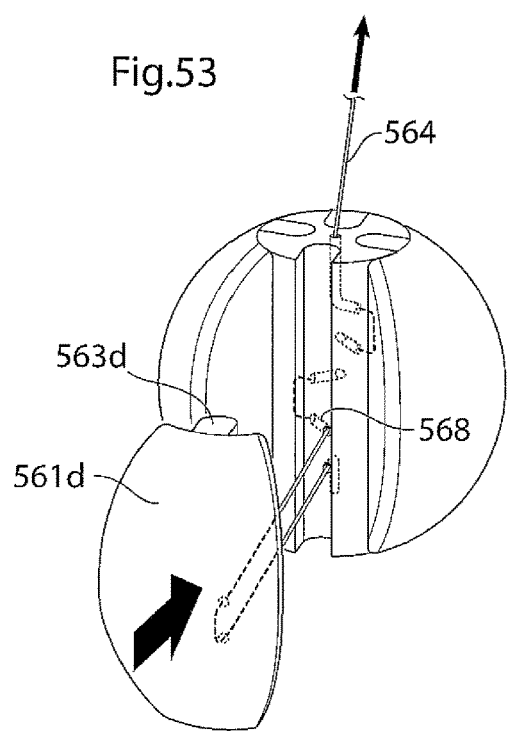
FIG. 53 shows the embodiment of FIG. 52 when assembling the final part.
Figure 54:
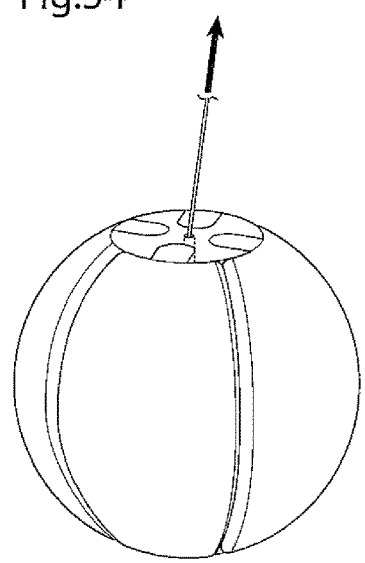
FIG. 54 shows the embodiment of FIGS. 50-53 when finally assembled.
Figure 55A:
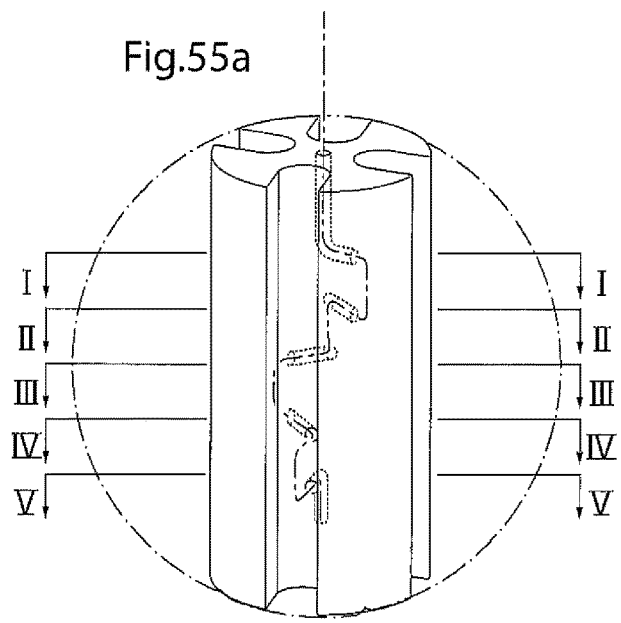
FIG. 55a shows the core part of the embodiment of FIG. 50 with the operation channels.
Figure 55B:
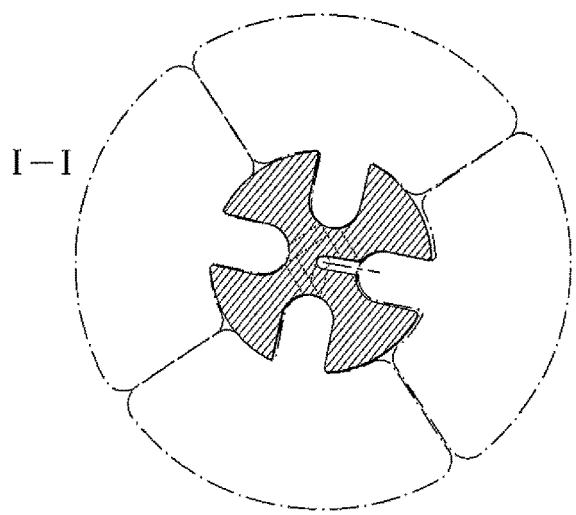
FIGS. 55b to 55f show cross sectional views of the core part of FIG. 55a according to planes I-I; II-II, III-III, IV-IV, respectively.
Figure 55C:
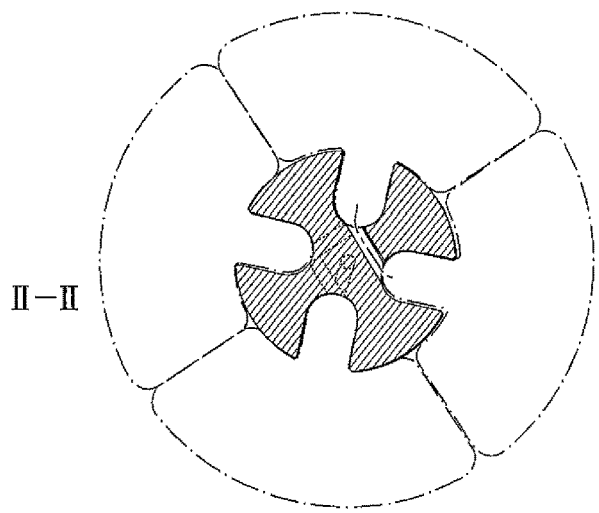
Figure 55D:
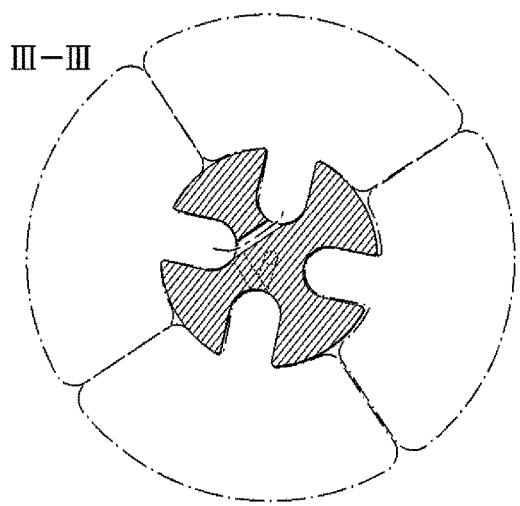
Figure 55E:
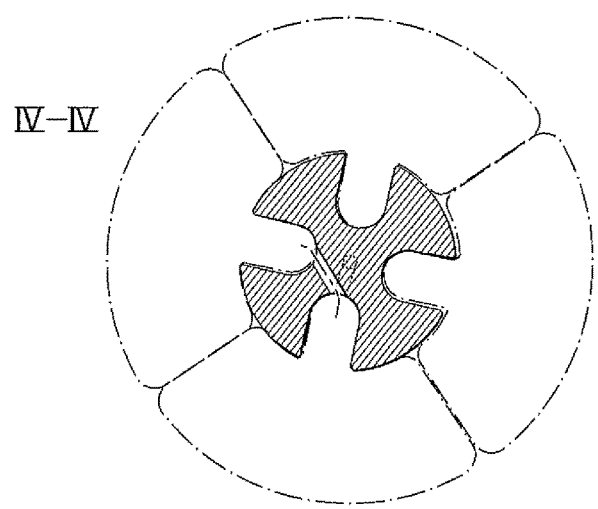
Figure 55F:
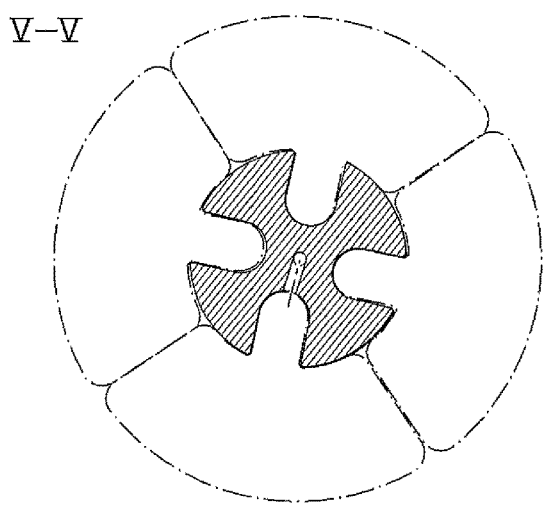

FIG. 50 shows an embodiment of an apparatus according to the invention. FIG. 50 shows the segments of a volume filling device to be assembled before implantation in a patient in the need of treatment for obesity. The volume filling device segments include a core part 560 and four outer parts 561*a*-561*d*. The generally cylindrical core part is provided with an upper part 560' and is provided with four slits 562*a*-562*d* which are symmetrically distributed end extend along the peripheral outside of the core part, The outer parts 561*a*-561*s* are shown as generally being a part of sphere having an inner and outer surface and each part is provided with a protruding flange 563*a*-563*d* extending along the inner surface. The flanges 563*a*-563*d* matches the slits 562*a*-562*d* in the depicted embodiment, but can be arranged with loose fits between flanges and slits so the assembled volume filling device sufficiently is assembled at its implanted target position above the cardia. If the volume filling device inadvertently is displaced from this position to the stomach cavity, a loose fit arrangement contributes to a more rapid disassembly its segments. The core part is connected to a guiding wire 564 which extends through first channel 565 in the core part though a corresponding channel 565*a* between two neighboring orifices in the protrusion 563*a* in the first outer part 561*a*. When operating on the guiding wire 564 by displacing it away from the core part upper surface 560' the first outer part 561*a* will be displaced towards the core part and the flange 563*a* meets the slit 562*a* so the first outer part is assembled to the core part 560. As demonstrated in FIG. 51, this performance is repeated with the second outer part, now by the guiding wire 564 through the second channel 566 connected to a corresponding channel in the flange 563*b* of second outer part 561*b*. FIG. 52 shows this performance again for assembling the third outer part 561*c* and third channel 567 connecting the guiding wire 564 to flange 563*c*. FIG. 53 shows the fourth and last outer part 561*d* being assembled through flange 563*d* and channel 568. FIG. 54 shows the finally assembled volume filling device. FIG. 55*a* is a more detailed view of the core part showing the system of channels for the guiding wire. FIGS. 55*b* to 55*d* are cross sectional views of planes I-I, II-II, III-III and IV-IV, respectively each at the level for four channels.

The guiding wire is made of a biodegradable material that is degraded so the segments readily become disassembled if the volume filling device accidently becomes displaced from its implanted position. The segments depicted are made from a biocompatible solid material and are each of size and shape so they readily pass through the gastrointestinal system if the volume filling device is disassembled. When implanting the so assembled volume filling device any of the previously described methods will be suitable.

Figure 56:
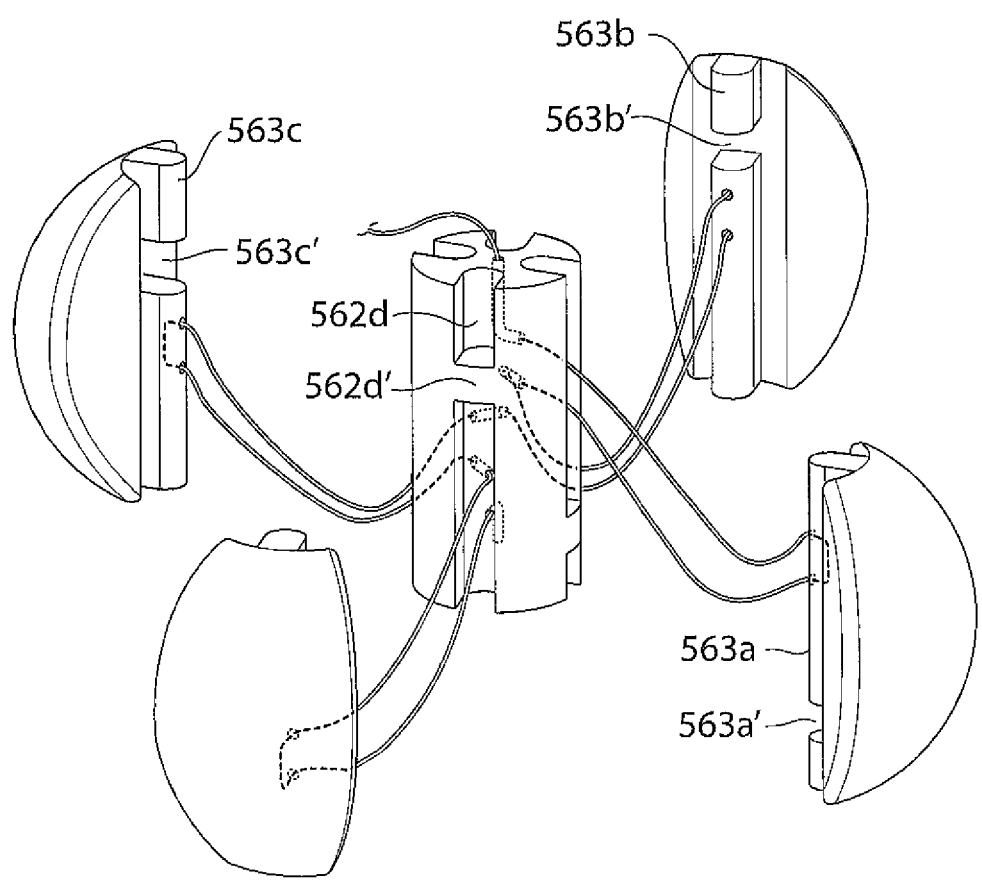
FIGS. 56 and 57 show different embodiments of the volume filling device segments.
Figure 57:
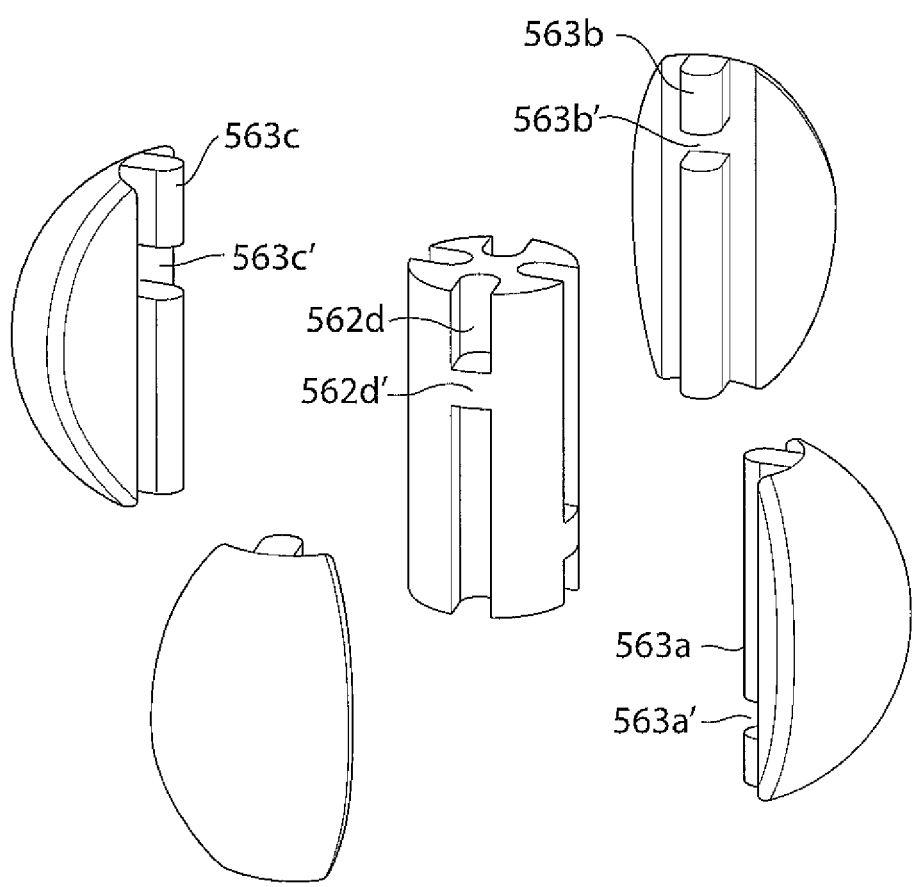

FIG. 56 shows an embodiment of the volume filling device to be assembled. The outline of the core part and the segments is identical as has been shown in FIG. 50, but the flanges 563*a*-*d* of the segments are provided with recesses 563'*a*-*d* that match protrusions 562'*a*-*d* of the slits 562*a*-*d* of the core part so the assembled movement device becomes locked along two different planes. In this embodiment, these planes are perpendicularly arranged. FIG. 57 shows another embodiment of the volume filling device according to FIG. 56 without any guiding wire and without any features for the guiding wire in the segments. This embodiment requires that matching element locking elements are adapted to assist with the disassembly if the volume filling device inadvertently becomes displaced from its implanted position.

Figure 58A:
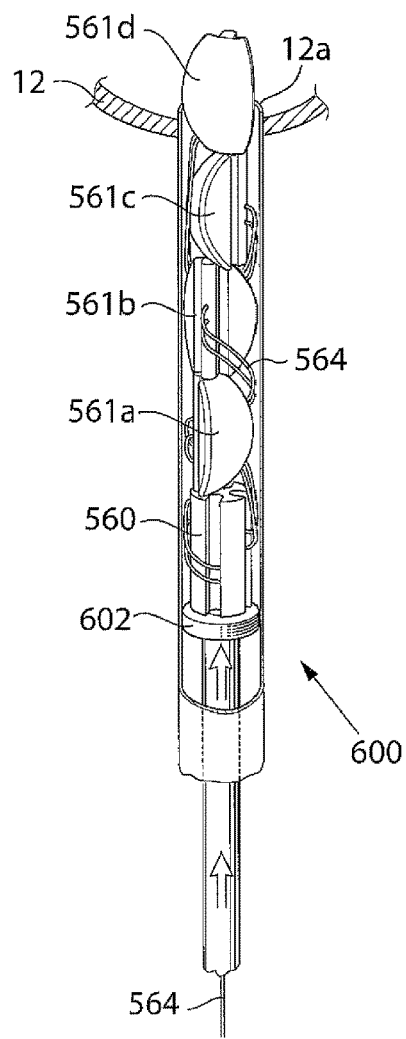
FIGS. 58a-d illustrate the insertion of the volume filling device segments shown in FIG. 56 by means of an instrument.

A method of injecting or inserting a plurality of volume filling device segments into a pouch formed by a part of a stomach wall will now be described with reference to FIGS. 58*a*-*d*. In this example, a volume filling device as described above with reference to FIG. 50 will be used. A tube-like instrument, generally designated 600, such as the one also depicted in FIG. 4*b*, comprises a sleeve 600*a* having a cross-sectional diameter and shape so as to allow the passage of the core part 560 and the four outer parts 561*a*-561*d*. A piston 602 is provided to displace the volume filling device segments through the sleeve 600*a* and into a space, wherein the volume filling device segments are to be assembled into or form a volume filling device. As shown in FIG. 58*a*, in this example the instrument 600 is used to insert or inject the volume filling device segments through a hole 12a in a stomach wall portion 12 of a patient.

Figure 58B:
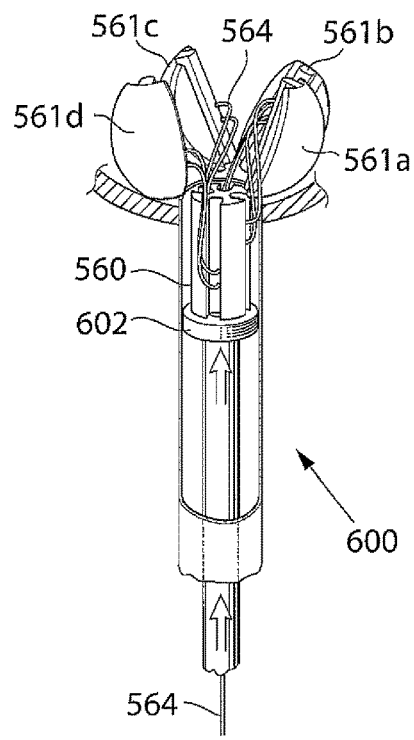

As shown in FIG. 58b, the guiding wire 564 forces the outer parts 561a-d to take a respective position like petals to allow the core part 560 to take a position allowing the outer parts 561a-d and the core part 560 to assemble into an essentially spherical volume filling device 10. By pulling the guiding wire 564, see FIG. 58c, the outer parts 561a-d are moved into engagement with the core part 560, being kept in position by means of the interlocking flanges 563a-d.

Figure 58D:
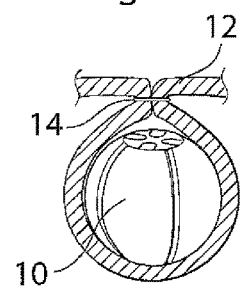
Figure 58C:
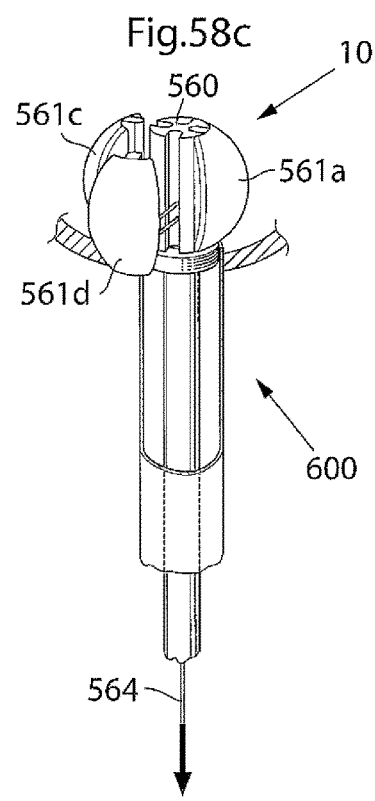
Figure 61A:
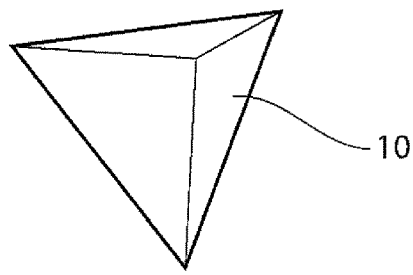
FIGS. 61a-e illustrate different shapes of volume filling devices when using a plurality of volume filling device segments to form a volume filling device.
Figure 61B:
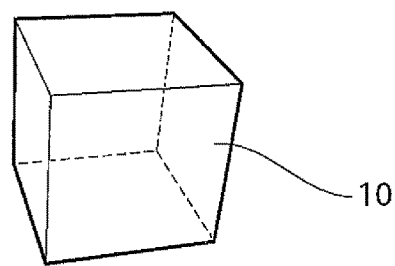
Figure 61C:
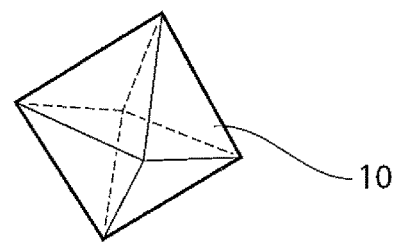
Figure 61D:
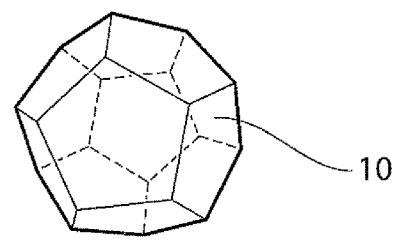
Figure 61E:
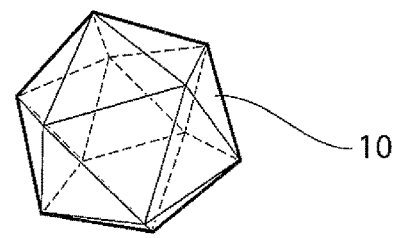

After being fully assembled, see FIG. 58d, the essentially spherical volume filling device 10 is invaginated in part of the stomach wall 12 by means of sutures or staples 14. The limited space of the pouch formed by the stomach wall prevents the volume filling device 10 from falling apart, even after the biodegradable guiding wire 564 has been degraded. However, in the event that volume filling device 10 comes loose, such as by the sutures or staples 14 breaking, the volume filling device 10 falls apart so that the different segments, each being smaller than the assembled volume filling device 10, can pass through the gastrointestinal system.

It is evident from the general description and the appended claims that many of other ways designing the volume filling device is possible without departing from this concept. One such way is to let a plurality of relatively small volume filling device segments form a volume filling device, which will now be described with reference to FIGS. 59a-c.

This method of injecting or inserting volume filling device segments into a pouch is similar to the one described above with reference to FIGS. 4a-d, after a pouch has been created in the stomach wall. Thus, FIG. 59a illustrates a stomach wall portion 12a after sutures or staples 14 have been applied to create a pouch in the stomach wall. The pouch can be provided by using the method described above with reference to FIGS. 5a-i.

Volume filling device segments 10 are inserted or injected into the pouch by means of a gastroscopic or laparoscopic, tube-like instrument 600, such as the one also depicted in FIG. 4b. The instrument comprises an outer sleeve and an inner sleeve, see FIG. 4b, which can be displaced longitudinally relatively to the outer sleeve. The inner sleeve is provided with a cutter in the form of a cutting edge 615 at the distal end thereof. This cutting edge can be used for cutting a hole in the stomach wall, as will be explained in detail in the following.

When the instrument reaches a stomach wall, the inner sleeve is brought forward from its position in the outer sleeve and into contact with the stomach wall 12a. The cutting edge 615 of the inner sleeve then cuts a hole in the stomach wall so as to allow subsequent insertion of the volume filling devices 10 into and through this hole, see FIG. 59b. In order to push the volume filling device through the hole, a piston 602 may be provided in the instrument. Thus, the instrument further comprises a piston 602 adapted for pushing a plurality of volume filling devices 10 out from a position in the inner sleeve, this position being shown in FIG. 59a, to a position outside of the inner sleeve, this being shown in FIG. 59b.

In order to protect the deflated volume filling device 10 from the cutting edge 615 of the inner sleeve, a further protective sleeve (not shown) can be provided around the volume filling device.

The tube-like instrument 600 is in the shown embodiment provided with a cup-shaped extension keeping the pouch in place during the insertion of the volume filling device segments 10 into the pouch. By gradually withdrawing the tube-like instrument 600 during this process, see FIG. 59b, the pouch can be filled with volume filling device segments 10 in a controlled way.

After the pouch has been filled with volume filling device segments to a desired degree, see FIG. 59c, the hole 12b cut in the stomach wall 12a by means of the tube-shaped instrument 600 is permanently closed by means of suturing or stapling, for example.

In the embodiment shown in FIGS. 59a-c, the tube-like instrument 600 comprises a piston 602 adapted to push or displace the volume filling device segments 10 along the sleeve 600b. Alternatively, as shown in FIG. 59, pressure exerted by fluid can be used to push or displace the volume filling device segments 10.

The volume filling device segments 10 can take many different shapes. In the embodiments shown in FIGS. 58a-c and 59, they are essentially spherical. However, in alternative embodiments, they exhibit one or a plurality of flat or essentially flat surfaces. Preferably, they then take the shape of polyhedrons, such as tetrahedrons, hexahedrons, octahedrons, dodecahedrons or icosahedrons, i.e., regular polyhedrons with four, six, eight, twelve, and twenty flat surfaces, respectively. These examples of volume filling device segments are shown in FIGS. 61a-e.

The volume filling devices can additionally be kept in their mutual relationship by means of additional measures. For example, the surfaces of the volume filling device segments can be provided with friction enhancing agent or material to minimize slipping of the volume filling device segments. The friction enhancing agent can be some kind of glue or the like. Alternatively or additionally, the surface or surfaces of the volume filling device segments can be given a rugged texture to increase the friction between adjacent volume filling device segments.

Figure 62:
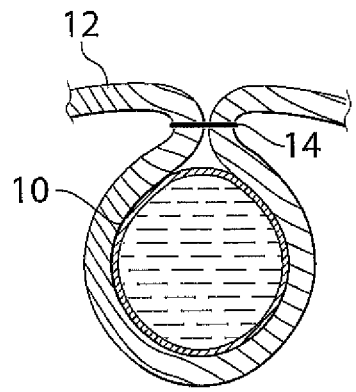
FIG. 62 is a sectional view of a volume filling device comprising fluid.

As mentioned above, the volume filling device 10 may be inflated with a gel or fluid supplied into a chamber defined by the volume filling device 10, see FIG. 62.

Insertion or injection of a plurality of volume filling device segments 10 into a natural pouch provided by a stomach wall portion 12 has been described above with reference to FIGS. 59a-d. However, in an alternative embodiment of an apparatus for treating obesity, the volume filling device segments can also comprise a volume filling device segment for collecting two or more other volume filling device segments, which are of a different kind. Thus, the apparatus comprises an expandable second volume filling device segment 10' for collecting two or more first volume filling device segments 10 different from the second volume filling device segment, wherein the second volume filling device segment and the first volume filling device segments together form the volume filling device. It is preferred that the second volume filling device segment is flexible or stretchable.

Figure 64:
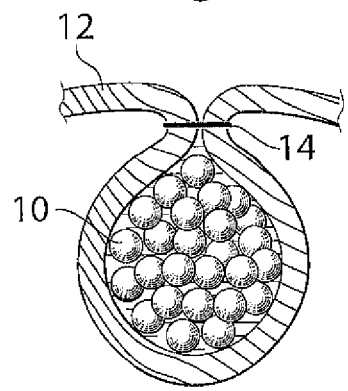
FIG. 64 is a view of a volume filling device comprising a plurality of volume filling device segments contained in a fluid.
Figure 65:
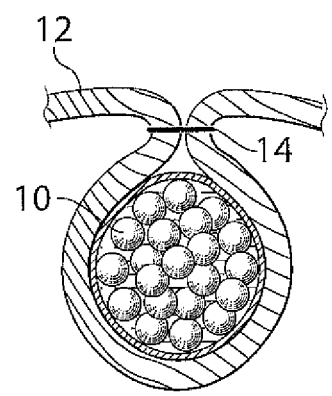
FIG. 65 is a sectional view of a volume filling device defining a plurality of volume filling device segments contained in a fluid.

In an alternative embodiment, to allow reshaping of the volume filling device, there may be a friction reducing fluid to reduce the friction between adjacent volume filling device segments. In FIG. 64, it is shown how a plurality of volume filling device segments 10 are provided in a pouch created by part of a stomach wall 12 and a fluid has been injected into this pouch, which allows mutual movement between adjacent first volume filling device segments so that the shape of the volume filling device adapts to stomach wall movements, when said volume filling device is invaginated in a stomach wall.

Figure 63:
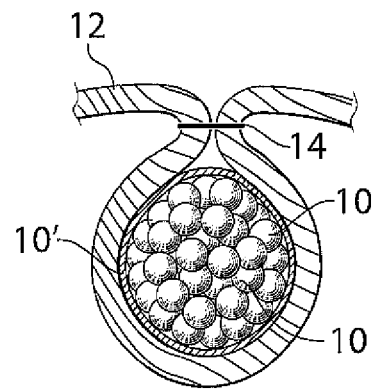
FIG. 63 is a sectional view of a volume filling device defining a plurality of volume filling device segments.

The embodiments of FIG. 63 and FIG. 64 may be combined, so that an outer volume filling device segment 10' encloses both a plurality of different, in this case spherical, volume filling device segments 10 as well as a fluid, which reduces the friction between the different volume filling device segments.

The fluid described above may, instead of reducing the friction between adjacent volume filling device segments, enhance the friction between adjacent volume filling device segments, thus making the volume filling device more stable. The friction enhancing material may also be a glue or an adhesive, i.e., a solidifying liquid.

Volume filling device segments adapted to be used in a plurality to form a volume filling device have been described above with reference to FIGS. 59a-c and 59a-e. It will be appreciated that these volume filling device segments can be given the same properties as the volume filling devices described earlier regarding materials, properties etc.

In a first alternative embodiment, the volume filling device is implanted using a laparoscopic method instead of the intraluminar method described above. According to this embodiment, a needle or a tube-like instrument is inserted into the abdomen of the patient's body, and said needle or tube-like instrument is then used to fill the patient's abdomen with gas. Subsequently, at least two laparoscopic trocars are inserted into the patient's body; and a camera is inserted through one of said at least two laparoscopic trocars. Then, at least one dissecting tool through one of said at least two laparoscopic trocars, and an area of the stomach is dissected. The volume filling device is then introduced into the abdominal cavity, and placed on the outside of the stomach wall. A pouch in the stomach wall for the device is created, and the device invaginated in said pouch by providing sutures or staples to the stomach wall, thereby positioning the volume filling device so that the volume of the food cavity is reduced in size by a volume substantially exceeding the volume of the volume filling device.

The above first alternative preferably further comprises affixing the device to the stomach wall by providing sutures or staples.

The above embodiment preferably further comprises providing an apparatus for regulating the obesity treatment device from the outside of the patient's body; and operating said apparatus to regulate the obesity treatment device. Further, regulation of the obesity treatment device includes changing the volume of a filling body of the volume filling device when implanted.

The above embodiment preferably further comprises providing an injection type syringe comprising a fluid for injection into an implanted filling body; and injecting volume of fluid into said filling body.

According to an embodiment, the device is enclosed in the pouch or partially enclosed in that the pouch is left at least partly open. Further, the pouch can be designed to exhibit only one opening. Alternatively the pouch is designed to exhibit two openings and to extend non-circumferentially around the stomach.

Preferably the pouch has a volume of more than 15 milliliters.

In a second alternative, also using a laparoscopic method instead of the intraluminar method, the initial steps are the same as described in the first alternative, but following dissection of the stomach, a hole is created in the stomach wall and a volume filling device introduced into the abdominal cavity and through said hole into the stomach. The device is placed on the inside of the stomach wall, and a pouch is created on the outside of the stomach cavity for the device placed on the inside of the stomach wall, and the device is invaginated in the pouch by providing sutures or staples to the stomach wall, thereby positioning the volume filling device so that the volume of the food cavity is reduced in size by a volume substantially exceeding the volume of the volume filling device.

The above embodiment preferably further comprises affixing the device to the stomach wall by providing sutures or staples. According to one embodiment, the stomach wall is affixed to the lower part of the patient's esophagus by providing sutures or staples.

The above second alternative preferably further comprises providing an apparatus for regulating the obesity treatment device from the outside of the patients body; and operating said apparatus to regulate the obesity treatment device. Further, regulation of the obesity treatment device includes changing the volume of a filling body of the volume filling device when implanted.

The above embodiment preferably further comprises providing an injection type syringe comprising a fluid for injection into an implanted filling body; and injecting volume of fluid into said filling body.

According to an embodiment, the device is enclosed in the pouch or partially enclosed in that the pouch is left at least partly open. Further, the pouch can be designed to exhibit only one opening. Alternatively the pouch is designed to exhibit two openings and to extend non-circumferentially around the stomach.

Preferably the pouch has a volume of more than 15 milliliters.

A third alternative involves a surgical incision instead of the either the intraluminar or the laparoscopic method. Here, an opening in the patient's abdominal wall is made by surgical incision, and an area of the patient's stomach is dissected. The volume filling device is introduced through said abdominal incision, and attached to the stomach wall, thereby positioning the volume filling device so that the volume of the food cavity is reduced in size by a volume substantially exceeding the volume of the volume filling device.

In an alternative embodiment of the above, third alternative, the initial steps are the same including the dissection of an area of the stomach. Following this, a pouch in the stomach wall is created for the device, and the device invaginated in the pouch by providing sutures or staples to the stomach wall, thereby positioning the volume filling device so that the volume of the food cavity is reduced in size by a volume substantially exceeding the volume of the volume filling device.

In yet another alternative embodiment of the above, third alternative, the initial steps are the same including the dissection of an area of the stomach. Following this, a hole in the stomach wall is created and the volume filling device introduced through the hole and into the stomach. The device is then placed on the inside of the stomach wall, and a pouch on the stomach wall created for the device. The device is then invaginated in the pouch by providing sutures or staples to the stomach wall, thereby positioning the volume filling device so that the volume of the food cavity is reduced in size by a volume substantially exceeding the volume of the volume filling device.

The above embodiments of the third alternative further comprise affixing the device to the stomach wall by providing sutures or staples.

The above embodiment preferably further comprises providing an apparatus for regulating the obesity treatment device from the outside of the patients body; and operating said apparatus to regulate the obesity treatment device.

Further, regulation of the obesity treatment device includes changing the volume of a filling body of the volume filling device when implanted.

The above embodiment preferably further comprises providing an injection type syringe comprising a fluid for injection into an implanted filling body; and injecting volume of fluid into said filling body.

According to an embodiments the device is enclosed in the pouch or partially enclosed in that the pouch is left at least partly open. Further, the pouch can be designed to exhibit only one opening. Alternatively the pouch is designed to exhibit two openings and to extend noncircumferentially around the stomach.

Preferably the pouch has a volume of more than 15 milliliters.

A fourth alternative embodiment is a method comprising the steps of inserting a needle or a tube-like instrument into the abdomen of the patient's body; using said needle or tube-like instrument to fill the patient's abdomen with gas; placing at least two laparoscopic trocars in the patients body; inserting a camera through one of said at least two laparoscopic trocars into the patient's abdomen; inserting at least one dissecting tool through one of said at least two laparoscopic trocars; dissecting an area of the stomach; creating a pouch from the stomach wall for the device; closing the pouch by providing sutures and staples; introducing a injecting member comprising an injectable filling material; and injecting the filling material into the pouch, thereby creating a filling body that fills a volume in the patient's stomach, reducing the food cavity in size by a volume substantially exceeding the volume of the volume filling device.

Instead of the above disclosed laparoscopic method, a surgical incision or opening is cut in the skin to enter the patient's abdomen; an area of the stomach dissected; a pouch created from the stomach wall for the device; and said pouch closed by providing sutures and staples. An injecting member comprising an injectable filling material is then introduced; and the filling material injected into the pouch, thereby creating a filling body that reduces the food cavity in size by a volume substantially exceeding the volume of the volume filling device.

According to an alternative embodiment of the above, the pouch is created on the outside of the stomach wall, with the filling body placed against the inside of the stomach wall.

The method according to either of the two previous embodiments comprises creating a hole in the stomach wall wherein the pouch is created on the inside of the stomach wall, with the filling body placed against the outside of the stomach wall.

The method according to either of the two previous embodiments may further comprise affixing the stomach wall to the lower part of the patient's esophagus by providing sutures or staples or affixing the stomach wall to the patient's diaphragm muscle or other muscle tissue.

Preferably the pouch has a volume of more than 15 milliliters.

In a method according to either of the two previous embodiments the filling material is preferably capable of undergoing a curing process from a fluid state to a semi-solid or solid state. Preferably said curing process is triggered by an increase in temperature from ambient temperature to body temperature.

The invention also makes available a method of treating obesity in a patient by implanting a volume filling device that, when implanted in a patient, reduces the food cavity in size by a volume substantially exceeding the volume of the volume filling device, the method comprising the steps of: inserting a needle or a tube-like instrument into the abdomen of the patient's body; using said needle or tube-like instrument to fill the patient's abdomen with gas; placing at least two laparoscopic trocars in the patient's body; inserting a camera through one of said at least two laparoscopic trocars into the patient's abdomen; inserting at least one dissecting tool through one of said at least two laparoscopic trocars; dissecting an area of the stomach; creating a hole in the stomach wall; introducing a device into the abdominal cavity; introducing the device through the hole and into the stomach; placing the device on the outside of the stomach wall; fixating the device placed on the outside of the stomach wall, and thereby creating a filling body that reduces the food cavity in size by a volume substantially exceeding the volume of the volume filling device.

In the above method, the device is preferably affixed to the stomach wall by providing sutures or staples.

The invention also comprises a laparoscopic instrument for providing a volume filling device to be invaginated in the stomach wall of a human patient to treat obesity, suitable for use with any of the laparoscopic methods described above, the instrument comprising: an elongated member having a proximal end and a distal end, the elongated member having a diameter less than that of a laparoscopic trocar to be introduced into the patients abdomen during a laparoscopic operation; a stomach pushing device for pushing the stomach wall to create a tube-like shaped portion of the stomach wall protruding into the normal stomach cavity, said pushing device comprising the volume filling device to be invaginated by the stomach wall in the tube-like shaped portion thereof; wherein the pushing device comprises a vacuum device to suck the stomach fundus to assist the instrument in forming the tube-like shaped portion of the stomach wall together with the pushing device, and wherein the vacuum device comprises a vacuum passageway leading from the proximal to the distal end of the instrument and at the end portion of the instrument which includes the pushing device, said vacuum passageway is divided up in multiple small openings adapted to suck the stomach wall portion to become adherent to the pushing device to further form the tube-like stomach wall portion; and wherein the instrument comprises an insertion device adapted to introduce the volume filling device into the tube-like shaped stomach portion.

This instrument preferably comprises at least one clamping device for holding the opening of the tube-like portion substantially closed by clamping together stomach to stomach in said opening, wherein the instrument is adapted to place the at least one clamping device at the opening in such a way that it allows later suturing of the opening.

Further, the instrument preferably comprises an inflation device for inflating the volume filling device before or after the suturing. Further still, the instrument preferably comprises a suturing device adapted to suture the opening of the tube-like portion with stomach to stomach sutures for creating at least partly a closed space enclosing the volume filling device, wherein the instrument is adapted to be withdrawn leaving the volume filling device at least partly invaginated in the stomach wall.

Said suturing device preferably comprises a first and second suture positioning member provided on the elongated member situated in the stomach at the distal end thereof, and wherein the instrument further comprises an operation device adapted to adjust the first and second suturing member in a position in which the first and second suture positioning members are in front of each other with the stomach wall on both sides of the open end of the cup like portion, and adapted to suture the open end of the cup like portion of the wall with a row of stomach to stomach sutures.

Preferably said suturing device comprises an operable re-loadable multi-suturing device, which is reloadable with sutures from outside of the patient's body and which is adapted to suture the open end of the cup like portion of the wall with said row of stomach to stomach sutures, wherein the row of sutures comprises two or more sutures or staples to be sutured simultaneously.

More preferably, said suturing device comprises multiple sutures for suturing two or more sutures simultaneously.

A method or part of method to be used in any combination and using any apparatus or part of apparatus or any feature in any combination where the following method steps is applicable, wherein said method may comprise one or more of the following operational method steps:

introducing said instrument into the throat,
passing down the esophagus,
placing an anvil or unit for delivery of fixating members in the esophagus between the cardia and the diaphragm level, for engaging in the fixation of the esophagus to the stomach tissue,
passing down the esophagus and additionally further down into the stomach,
filling the stomach with gas to expand the stomach,
sucking fluid from the stomach,
looking at a guiding vision when said instrument comprising a camera,
engaging the instrument with the stomach,
creating and suturing at least one pouch of the stomach wall,
filling said at least one pouch with a fluid and/or volume filling device or two or more volume filling devices,
deliver a plurality of volume filling devices into said pouch created in the stomach tissue through a tubular member,
passing through the stomach wall with said instrument
passing through the stomach wall with said instrument for the placement of a volume filling device on the outside of the stomach wall,
passing through the stomach wall with said instrument for the placement of a tube allowing placement of a subcutaneous injection port,
placing an subcutaneous injection port,
suturing or stapling the stomach wall from the inside thereof to the esophagus,
suturing or stapling the stomach wall to stomach wall from the inside of the stomach,
engaging the instrument with the esophagus,
suturing or stapling one layer of stomach tissue to one layer of esophageal tissue,
suturing or stapling two layers of stomach tissue to one layer of esophageal tissue,
suturing or stapling three layers of stomach tissue to one layer of esophageal tissue,
suturing or stapling four layers of stomach tissue to one layer of esophageal tissue,
suturing or stapling one or more layers of stomach tissue to two or more positions on the esophageal tissue, the esophagus having an esophagus center axis, the esophagus further having an inner and outer substantially cylindrical surface extending radially in relation to the esophagus center axis and wherein the stomach tissue is attached to esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis,
delivering fixating members by a unit placed on said instrument,
penetrating at least one layer of stomach tissue and one layer of esophagus tissue with said fixating members,
placing said fixating members above the gastro-esophageal junction for creating a tunnel between the esophagus and stomach above said junction,
placing an esophagus part in the esophagus and a stomach part in the stomach,
placing the fixating member substantially between the stomach and esophagus part,
inserting said instrument into the main stomach cavity through the cardia and adapted to direct the instrument in cranial direction to reach a position of said unit above said junction,
allowing the tunnel a substantially unrestricted contraction and release of the cardia closing sphincter muscle placed in said junction, when such a tunnel has been created.

A method or part of method to be used in any combination and using any apparatus or part of apparatus or any feature in any combination where the following method steps is applicable, wherein said method comprises one or more of the following operational method steps:

cutting the skin of a patient
creating an opening in the abdominal wall of the patient
Introducing said instrument into the abdominal cavity through said opening in the abdominal wall,
engaging the instrument with the stomach,
pulling down into the stomach wall for creating at least one pre-shaped pouch of the stomach wall,
clamping the stomach wall for creating at least one pre-shaped pouch of the stomach wall,
suturing or stapling at least one pouch in the stomach wall,
filling said at least one pouch with a fluid and/or volume filling device or two or more volume filling devices,
deliver a plurality of volume filling devices into said pouch created in the stomach tissue through a tubular member,
passing through the stomach wall into the stomach with said instrument,
passing through the stomach wall with said instrument for the placement of a volume filling device on the inside of the stomach wall,
passing through the stomach wall with said instrument for suturing the stomach wall to the esophagus wall,
placing a volume filling device on the outside of the stomach wall,
invaginating said volume filling device in the stomach wall
placing a subcutaneous injection port,
suturing or stapling the stomach wall to stomach wall from the outside of the stomach,
suturing or stapling the stomach wall to stomach wall from the outside of the stomach without penetrating the mucosa,
suturing or stapling two layers of stomach wall to one or two layers of stomach wall,
engaging the instrument with the esophagus,
clamping the on both sides of the esophagus for fixating one layer of esophageal wall to stomach tissue, clamping the on both sides of the esophagus and the stomach fundus wall for fixating one layer of esophageal wall to one or two layers of stomach tissue, introducing a tube or a gastroscopic instrument into the esophagus comprising an anvil member or a fixating delivery member involving in the fixation of the esophagus to the stomach, coordinating the position of the anvil member or a fixating delivery member inside the esophagus to said instrument clamping around the esophagus, suturing or stapling one layer of stomach tissue to one layer of esophageal tissue, suturing or stapling two layers of stomach tissue to one layer of esophageal tissue, suturing or stapling three layers of stomach tissue to one layer of esophageal tissue, suturing or stapling four layers of stomach tissue to one layer of esophageal tissue, stapling using staplers of different stapling depths at different positions in a stapler row, stapling stomach to esophagus with one first stapler depth and stapling stomach to stomach with a second smaller stapler depth, stapling a pouch with stomach to stomach sutures in a stapler row, further comprising stapling the esophagus with staplers of a larger depth included as a part of said stapler row, suturing or stapling one or more layers of stomach tissue to two or more positions on the esophageal tissue, the esophagus having an esophagus center axis, the esophagus further having an inner and outer substantially cylindrical surface extending radially in relation to the esophagus center axis and wherein the stomach tissue is attached to esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis, delivering fixating members by a unit placed on said instrument, penetrating at least one layer of stomach tissue and one layer of esophagus tissue with said fixating members, placing said fixating members above the gastro-esophageal junction for creating a tunnel between the esophagus and stomach above said junction, allowing the tunnel a substantially unrestricted contraction and release of the cardia closing sphincter muscle placed in said junction, when such a tunnel has been created, placing an esophagus part in the esophagus and a stomach part in the stomach via an introduction into the stomach cavity, placing the fixating member substantially between the stomach and esophagus part, inserting said instrument into the main stomach cavity below said junction and adapted to direct the instrument in cranial direction to reach a position of said unit above said junction, operating a joint comprised in said instrument, for enabling said instrument to be inserted into the main stomach cavity bending said joint in a direction to reach a position of said part of the unit in the esophagus above said junction.

A method or part of method to be used in any combination and using any apparatus or part of apparatus or any feature in any combination where the following method steps is applicable, wherein said method comprises one or more of the following laparoscopic operational method steps:

cutting the skin of a patient introducing a tube through the abdominal wall, filling a fluid or gas into the abdominal cavity, introducing two or more trocars into the abdominal cavity, introducing a camera into the abdominal cavity through one of the trocars, introducing said instrument into the abdominal cavity through a trocar, engaging the instrument with the stomach, pulling down into the stomach wall for creating at least one pre-shaped pouch of the stomach wall, clamping the stomach wall for creating at least one pre-shaped pouch of the stomach wall, suturing or stapling at least one pouch in the stomach wall, filling said at least one pouch with a fluid and/or a volume filling device or two or more volume filling devices, deliver a plurality of volume filling devices into said pouch created in the stomach tissue through a tubular member, passing through the stomach wall into the stomach with said instrument, passing through the stomach wall with said instrument for the placement of a volume filling device on the inside of the stomach wall, passing through the stomach wall with said instrument for suturing the stomach wall to the esophagus wall, placing a volume filling device on the outside of the stomach wall, invaginating said volume filling device in the stomach wall placing a subcutaneous injection port, suturing or stapling the stomach wall to stomach wall from the outside of the stomach, suturing or stapling two layers of stomach wall to one or two layers of stomach wall, suturing or stapling the stomach wall to stomach wall from the outside of the stomach without penetrating the mucosa, engaging the instrument with the esophagus, clamping the on both sides of the esophagus for fixating one layer of esophageal wall to stomach tissue, clamping the on both sides of the esophagus and the stomach fundus wall for fixating one layer of esophageal wall to one or two layers of stomach tissue, introducing a tube or a gastroscopic instrument into the esophagus comprising an anvil member or a fixating delivery member involving in the fixation of the esophagus to the stomach, coordinating the position of the anvil member or a fixating delivery member inside the esophagus to said instrument clamping around the esophagus, suturing or stapling one layer of stomach tissue to one layer of esophageal tissue, suturing or stapling two layers of stomach tissue to one layer of esophageal tissue, suturing or stapling three layers of stomach tissue to one layer of esophageal tissue, suturing or stapling four layers of stomach tissue to one layer of esophageal tissue, stapling using staplers of different stapling depths at different positions in a stapler row, stapling stomach to esophagus with one first stapler depth and stapling stomach to stomach with a second smaller stapler depth, stapling a pouch with stomach to stomach sutures in a stapler row, further comprising stapling the esophagus with staplers of a larger depth included as a part of said stapler row, suturing or stapling one or more layers of stomach tissue to two or more positions on the esophageal tissue, the esophagus having an esophagus center axis, the esophagus further having an inner and outer substantially cylindrical surface extending radially in relation to the esophagus center axis and wherein the stomach tissue is attached to esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis, delivering fixating members by a unit placed on said instrument, penetrating at least one layer of stomach tissue and one layer of esophagus tissue with said fixating members, placing said fixating members above the gastro-esophageal junction for creating a tunnel between the esophagus and stomach above said junction, allowing the tunnel a substantially unrestricted contraction and release of the cardia closing sphincter muscle placed in said junction, when such a tunnel has been created, placing an esophagus part in the esophagus and a stomach part in the stomach via an introduction into the stomach cavity, placing the fixating member substantially between the stomach and esophagus part, inserting said instrument into the main stomach cavity below said junction and adapted to direct the instrument in cranial direction to reach a position of said unit above said junction, operating a joint comprised in said instrument, for enabling said instrument to be inserted into the main stomach cavity bending said joint in a direction to reach a position of said part of the unit in the esophagus above said junction.

Please note that any embodiment or part of embodiment as well as any method or part of method or any apparatus or part of apparatus or any feature or part of feature or any system or part of system could be combined in any applicable way. All examples herein should be seen as part of the general description and therefore possible to combine in any way in general terms.

It is understood that a skilled person is in the position of combining steps, changing the order of steps, and combining elements of the different embodiments of the invention without inventive effort, and without departing from the scope of the invention as defined in the description and claims.

Please note that all the embodiments or features of an embodiment as well as any method or step of a method could be combined in any way if such combination is not clearly contradictory. Please also note that the description in general should be seen as describing both an apparatus and a device adapted to perform a method as well as this method in itself.

While specific embodiments of the invention have been illustrated and described herein, it is realized that numerous other embodiments may be envisaged and that numerous additional advantages, modifications and changes will readily occur to those skilled in the art without departing from the spirit and scope of the invention. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents. It is therefore to be understood that the appended claims are intended to cover all such modifications and changes as fall within a true spirit and scope of the invention. Numerous other embodiments may be envisaged without departing from the spirit and scope of the invention.

The invention claimed is:

1. An apparatus for treating obesity in a human or animal mammal patient, the apparatus comprising:
   two or more volume filling device segments configured to assemble to an implantable ball-shaped volume filling device configured to be invaginated in a stomach wall of the patient, such that a volume of the food cavity is reduced in size by a volume substantially exceeding the volume of the volume filling device, wherein at least two of said two or more volume filling device segments comprises:
   a connecting portion comprising at least one flat surface for connecting to another volume filling device segments, and
   a rounded outer surface portion configured to become part of an outer surface of the assembled ball-shaped volume filling device, wherein
   said assembled volume filling device is configures to dissembled into its volume filling device segments if the volume filling device leaves its invaginated stomach position, and wherein said volume filling device segments are adapted to separately pass through the food passageway, thereby reducing risk for causing obstruction/ileus in the patient's intestine.

2. The apparatus according to claim 1, wherein the volume filling device has a minimum circumference of at least 15 millimeters.

3. The apparatus according to claim 1, wherein the volume filling device segments has at least a part of an outer surface including a biocompatible material.

4. The apparatus according to claim 1, wherein the volume filling device segments are adapted to pass through a trocar, for assembly and implantation of said volume filling device into the abdominal cavity.

5. The apparatus according to claim 4, the volume filling device segments have a flexible outer shape adapted to pass through a trocar.

6. The apparatus according to claim 1, wherein the volume filling device segments are adapted to have a shape allowing them to be assembled into said volume filling device, when implanted.

7. The apparatus according to claim 1, wherein the volume filling device segments are hollow with a flexible outer surface.

8. The apparatus according to claim 7, wherein the volume filling device segments are adapted to be filled with at least one of a fluid, a foam, a gel or a fluid that hardens to a solid material.

9. The apparatus according to claim 1, wherein the volume filling device segments are solid.

10. The apparatus according to claim 1, wherein the volume filling device segments are adapted to temporarily holding their assembled position.

11. The apparatus according to claim 10, wherein the volume filling device segments are adapted to permanently hold their assembled position by the invaginated stomach wall.

12. The apparatus according to claim 11, wherein the volume filling device segments are adapted to temporarily holding their assembled position by an adhesive.

13. The apparatus according to claim 1, wherein the segments are of size that admits free passage through the gastrointestinal system.

14. The apparatus according claim 1, wherein that each segment is provided with at least one assembly element that sufficiently fits with at least one assembly element of another segment, so the segments by fitting assembly elements can be assembled into the implantable volume filling device.

15. The apparatus according to claim 14, wherein the segments comprise a core part and a plurality of outer parts.

16. The apparatus according to claim 15, wherein the core part is adapted to receive and assemble the outer the outer parts into an implantable volume filling device.

17. The apparatus according to claim 16, wherein the core part has assembly slits adapted to receive corresponding assembly flanges of the outer parts when assembling the volume filling device.

18. The apparatus according to claim 17, wherein the slits are distributed around an outer peripheral area of the core part.

19. The apparatus according to claim 14, wherein the assembly element is selected among sufficiently fitting flanges and slits.

20. The apparatus according to claim 1, wherein the apparatus further comprises a guiding device, operable for assembling the volume filling device segments to an implantable volume filling device.

21. A method of using an apparatus according to claim 1, wherein said method comprises one or more of the following operational method steps:
introducing an instrument into the throat,
passing down the esophagus,
creating and suturing at least one sealed pouch of the stomach wall, and
filling said at least one pouch with at least two volume filling device segments adapted to assemble into a volume filling device.

22. The method according to claim 21, wherein said method further comprises one or more of the following operational method steps:
placing an anvil or unit for delivery if fixating members in the esophagus
between the cardia and the diagram level, for engaging in the fixation of the esophagus to the stomach tissue,
passing down the esophagus and additionally further down into the stomach,
filling the stomach with gas to expand the stomach,
sucking fluid from the stomach,
looking at a guiding vision when said instrument comprising a camera,
engaging the instrument with the stomach,
passing through the stomach wall with said instrument,
passing through the stomach wall with said instrument for the placement of a volume filling device on the outside of the stomach wall,
passing through the stomach wall with said instrument for the placement of tube allowing placement of a subcutaneous infection port,
placing an subcutaneous injection port,
suturing or stapling the stomach wall from the inside thereof to the esophagus,
suturing or stapling the stomach wall to stomach wall from the inside of the stomach,
engaging the instrument with the esophagus,
suturing or stapling one or two or three or four layer of stomach tissue to one layer of esophageal tissue,
suturing or stapling one or more layers of stomach tissue to two or more positions on the esophageal tissue, the esophagus having an esophagus center axis, the esophagus further having an inner and outer substantially cylindrical surface extending radially in relation to the esophagus center axis and wherein the stomach tissue is attached to esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis, delivering fixating members by a unit placed on said instrument,
penetrating at least one layer of stomach tissue and one layer of esophagus tissue with said fixating members,
placing said fixating members above the gastro-esophageal junction for creating a tunnel between the esophagus and stomach above said junction,
placing an esophagus part in the esophagus and a stomach part in the stomach,
placing the fixating member substantially between the stomach and esophagus part,
inserting said instrument into the main stomach cavity through the cardia and adapted to direct the instrument in cranial direction to reach a position of said unit above said junction,
allowing the tunnel a substantially unrestricted contraction and release of the cardia closing sphincter muscle placed in said junction, when such a tunnel has been created.

23. A method of using an apparatus according to claim 1, wherein said method comprises one or more of the following laparoscopic operational method steps:
cutting the skin of a patient,
introducing a tube through the abdominal wall,
filling a fluid or gas into the abdominal cavity,
introducing two or more trocars into the abdominal cavity,
introducing a camera into the abdominal cavity through one of the trocars,
creating and suturing at least one sealed pouch of the stomach wall, and
filling said at least one pouch with at least two volume filling device segments adapted to assemble into a volume filling device,
passing down the esophagus and additionally further down into the stomach,
filling the stomach with gas to expand the stomach,
sucking fluid from the stomach,
looking at a guiding vision when an instrument comprising a camera,
engaging the instrument with the stomach,
passing through the stomach wall with said instrument, passing through the stomach wall with said instrument for the placement of a volume filling device on the outside of the stomach wall,
passing through the stomach wall with said instrument for the placement of a tube allowing placement of a subcutaneous injection port,
placing an subcutaneous injection port,
suturing or stapling the stomach wall from the inside thereof to the esophagus,
suturing or stapling the stomach wall to stomach from the inside of the stomach,
engaging the instrument with the esophagus,
suturing or stapling one or two or three or four layers of stomach tissue to one layer of esophageal tissue,
suturing stapling one or more layers of stomach tissue to two or more positions on the esophageal tissue, the esophagus having an esophagus center axis, the esophagus further having an inner and outer substantially cylindrical surface extending relation to the esophagus center axis and wherein the stomach tissue attached to a esophageal tissue both at a first point along a first esophagus surface length axis, substantially parallel to said esophagus center axis and at a second point along a second esophagus surface length axis, substantially parallel to said esophagus center axis, at a distance from said first esophagus surface length axis, radially in relation to said esophagus center axis, delivering fixating members by a unit placed on said instrument,
penetrating at least layer of stomach tissue and one esophagus tissue with said fixating member,
placing said fixating members above the gastro-esophageal junction tor creating a tunnel between the esophagus and stomach above said junction,
placing an esophagus part in the esophagus and a stomach part in the stomach,
placing the fixating member substantially between the stomach and esophagus part,
inserting said instrument into the main stomach cavity through the cardia and adapted to direct the instrument cranial direction to reach at position of said unit above said junction,
allowing the tunnel a substantially unrestricted contraction and release of the cardia closing sphincter muscle placed in said junction, when such a tunnel has been created.

24. The method according to claim 23, wherein said method further comprises one or more of the following operational method steps:
introducing said instrument into the abdominal cavity through a trocar,
engaging the instrument with the stomach,
pulling down into the stomach wall for creating at least one pre-shaped pouch of the stomach wall,
damping the stomach wall for creating at least one pre-shaped pouch of the stomach wall,
suturing or stapling at least one pouch in the stomach wall,
filling said at least one pouch with a fluid and/or a volume filling device or two or more volume filling devices,
delivering a plurality of volume filling devices into said pouch created in the stomach tissue through a tubular member,
passing through the stomach wall into the stomach with said instrument,
passing through the stomach wall with said instrument for the placement of a volume filling device on the inside of the stomach wall,
passing through the stomach wall with said instrument for suturing the stomach wall to the esophagus wall,
placing a volume filling device on the outside of the stomach wall,
invaginating said volume filling device in the stomach wall,
placing a subcutaneous injection port,
suturing or stapling the stomach wall to stomach wall from the outside of the stomach,
suturing or stapling two layers of stomach wall to one or two layers of stomach wall,
suturing or stapling the stomach wall to stomach wall from the outside of the stomach without penetrating the mucosa,
engaging the instrument with the esophagus,
clamping the on both sides of the esophagus for fixating one layer of esophageal wall to stomach tissue,
clamping on both sides of the esophagus and the stomach fundus wall for fixating one layer of esophageal wall to one or two layers of stomach tissue,
introducing a tube or a gastroscopic instrument into the esophagus comprising an anvil member or a fixating delivery member involving in the fixation of the esophagus to the stomach,
coordinating the position of the anvil member or a fixating delivery member inside the esophagus to said instrument damping around the esophagus,
suturing or stapling one or two or three or four layers of stomach tissue to one layer of esophageal tissue,
stapling using staplers of different stapling depths at different positions in a stapler row,
stapling stomach to esophagus with first stapler depth and stapling stomach to stomach with a second smaller stapler depth,
stapling a pouch with stomach to stomach suture in a stapler row, further comprising stapling the esophagus with staplers of a larger depth included as a part of said stapler row,
suturing or stapling one or more layers of stomach tissue to two or positions on the esophageal tissue, the esophagus having an esophagus center axis, the esophagus further having an inner and outer substantially cylindrical surface extending radially a relation to the esophagus center axis and wherein the stomach tissue is attached to esophageal tissue both at a first point along a first esophagus surface length axis, substantially parallel to said esophagus center axis and a second point along a second esophagus surface length axis, substantially parallel to said esophagus center axis, at a distance from said first esophagus surface length axis, radially in relation to said esophagus center axis,
delivering fixating members by a unit placed on said instrument,
penetrating at least one layer of stomach tissue and one layer of esophagus tissue with said fixating members,
placing said fixating member above the gastro-esophageal junction for creating a tunnel between the esophagus and stomach above said junction,
allowing the tunnel a substantially unrestricted contraction and release of the cardia closing sphincter muscle placed in said junction, when such a tunnel has been created, placing an esophagus part in the esophagus and a stomach part in the stomach via an introduction into the stomach cavity, placing the fixating member substantially between stomach and esophagus part, inserting said instrument into the main stomach cavity below said junction and adapted to direct the instrument in cranial direction position of said unit above said junction, operating a joint comprised in said instrument, for enabling said instrument to be inserted into the main stomach cavity bending said joint in a direction to reach a position of said part of the unit in the esophagus above said junction.

\* \* \* \* \*